(12) United States Patent
Chisaka et al.

(10) Patent No.: US 10,689,514 B2
(45) Date of Patent: *Jun. 23, 2020

(54) SILICON-CONTAINING RESIN COMPOSITION

(71) Applicant: TOKYO OHKA KOGYO CO., LTD., Kawasaki-shi (JP)

(72) Inventors: Hiroki Chisaka, Kawasaki (JP); Mayumi Kuroko, Kawasaki (JP); Kunihiro Noda, Kawasaki (JP); Dai Shiota, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 27 days.

This patent is subject to a terminal disclaimer.

(21) Appl. No.: 15/740,227

(22) PCT Filed: Jul. 8, 2016

(86) PCT No.: PCT/JP2016/070239
§ 371 (c)(1),
(2) Date: Dec. 27, 2017

(87) PCT Pub. No.: WO2017/007010
PCT Pub. Date: Jan. 12, 2017

(65) Prior Publication Data
US 2018/0187010 A1    Jul. 5, 2018

(30) Foreign Application Priority Data

Jul. 9, 2015 (JP) ................................ 2015-138064
Dec. 18, 2015 (JP) ................................ 2015-247917

(51) Int. Cl.
*C08L 83/04* (2006.01)
*C08L 83/16* (2006.01)
*C09D 183/04* (2006.01)
*C09D 183/16* (2006.01)
*C09D 7/40* (2018.01)
*C08G 77/60* (2006.01)
*C07C 69/14* (2006.01)
*C08J 5/18* (2006.01)

(52) U.S. Cl.
CPC .............. *C08L 83/04* (2013.01); *C07C 69/14* (2013.01); *C08G 77/60* (2013.01); *C08J 5/18* (2013.01); *C08L 83/16* (2013.01); *C09D 7/40* (2018.01); *C09D 183/04* (2013.01); *C09D 183/16* (2013.01); *C08J 2383/04* (2013.01); *C08J 2383/16* (2013.01)

(58) Field of Classification Search
CPC ................................ C08L 83/02; C08L 83/04
See application file for complete search history.

(56) References Cited

U.S. PATENT DOCUMENTS

| | | | |
|---|---|---|---|
| 7,939,590 B2 | 5/2011 | Iida et al. | |
| 8,404,786 B2 | 3/2013 | Akiyama et al. | |
| 2007/0178319 A1 | 8/2007 | Hamada et al. | |
| 2007/0185262 A1 | 8/2007 | Sakamoto | |
| 2008/0114115 A1 | 5/2008 | Iida et al. | |
| 2009/0018247 A1 | 1/2009 | Iida et al. | |
| 2009/0251652 A1 | 10/2009 | Kojima et al. | |
| 2011/0117746 A1* | 5/2011 | Maruyama | C08L 83/04 438/703 |
| 2013/0130179 A1 | 5/2013 | Anno et al. | |
| 2013/0287959 A1 | 10/2013 | Fish et al. | |
| 2016/0096977 A1 | 4/2016 | Tachibana et al. | |

FOREIGN PATENT DOCUMENTS

| | | |
|---|---|---|
| CN | 1950473 A | 4/2007 |
| CN | 101551589 A | 10/2009 |
| CN | 104245846 A | 12/2014 |
| EP | 1650276 A1 | 4/2006 |
| EP | 2256541 A1 | 12/2010 |
| JP | H08-269399 A | 10/1996 |
| JP | H09-031202 A | 2/1997 |
| JP | 2005-072615 A | 3/2005 |
| JP | 2006-291106 A | 10/2006 |
| JP | 2007-211062 A | 8/2007 |
| JP | 2008-120911 A | 5/2008 |
| JP | 2009-053273 A | 3/2009 |
| JP | 2009-211033 A | 9/2009 |
| JP | 2015-108087 A | 6/2015 |
| JP | 2016-074772 A | 5/2016 |

OTHER PUBLICATIONS

Machine translation of JP 2009/053273. (Year: 2009).*
Office Action issued in European Patent Application No. 16821478.1, dated Jun. 25, 2018.
Supplementary European search report issued in European Patent Application No. 16821478.1, dated Jun. 11, 2018.
Office Action issued in U.S. Appl. No. 15/855,291, dated Mar. 15, 2019.
Office Action issued in Taiwanese Patent Application No. 105121813, dated Aug. 13, 2019.

(Continued)

*Primary Examiner* — Wenwen Cai
(74) *Attorney, Agent, or Firm* — Knobbe, Martens, Olson & Bear LLP

(57) ABSTRACT

A silicon-containing resin composition with which it is possible to form a silica-based coating film in which generation of cracks is minimized, a method for forming a silica-based coating film using the silicon-containing resin composition, and a crack-free silica-based coating film formed using the silicon-containing resin composition. The silicon-containing resin composition includes a silicon-containing resin and a solvent, in which one or more of siloxane resins and polysilanes is used as the silicon-containing resin, and the solvent contains a cycloalkyl acetate having a specific structure.

7 Claims, No Drawings

(56) References Cited

OTHER PUBLICATIONS

Office Action issued in U.S. Appl. No. 15/855,291, dated Sep. 30, 2019.
Office Action issued in U.S. Appl. No. 15/855,291, dated on Jan. 16, 2020.
Office Action issued in Chinese Patent Application No. 201680035786.8, mailed on Feb. 3, 2020.

* cited by examiner

SILICON-CONTAINING RESIN COMPOSITION

This application is the U.S. National Phase under 35 U.S.C. § 371 of International Application PCT/JP2016/070239, filed Jul. 8, 2016, designating the U.S., and published in Japanese as WO 2017/007010 on Jan. 12, 2017 which claims priority to Japanese Patent Application No. 2015-138064, filed Jul. 9, 2015; and Japanese Patent Application No. 2015-247917, filed Dec. 18, 2015, the entire contents of which are incorporated herein by reference.

TECHNICAL FIELD

The present invention relates to a silicon-containing resin composition, a method for forming a silica-based coating film using the silicon-containing resin composition, and a crack-free silica-based coating film formed using the silicon-containing resin composition.

BACKGROUND ART

Silica-based coating films are used in various applications, for example, interlayer insulating films in various elements, sealing materials in light-emitting devices such as LED devices and organic EL devices, coating films capable of diffusing impurity across semiconductor substrates, and gap-filling material for semiconductor processing. Such silica-based coating films are typically formed by applying a liquid composition containing a silicon-containing resin, such as a siloxane resin, to a substrate to form a coating film and then baking the resulting coating film.

As a coating-film-forming material for use to obtain silica-based coating films, a liquid composition containing a siloxane resin with a particular structure, silica with an average particle diameter ranging from 10 nm to 50 nm, and an organic solvent is known, for example (Patent Document 1).

Patent Document 1: Japanese Unexamined Patent Application, Publication No. 2015-108087

DISCLOSURE OF THE INVENTION

Problems to be Solved by the Invention

In Patent Document 1, microsilica is used in an amount of at least 20% by mass relative to the total amount of the microsilica and a polysiloxane resin combined. Therefore, the skeleton of the siloxane resin is limited for the sake of ensuring compatibility. In addition, a silica-based coating film with a film thickness of about 5.0 μm formed by using the liquid composition described in Patent Document 1 has insufficient crack resistance.

The present invention has been made in view of the problems described above. An object of the present invention is to provide a silicon-containing resin composition capable of forming a silica-based coating film with inhibited crack formation, a method for forming a silica-based coating film using the silicon-containing resin composition, and a crack-free silica-based coating film formed using the silicon-containing resin composition.

Means for Solving the Problems

The inventors of the present invention have found that the problems described above can be solved by using a silicon-containing resin composition comprising (A) a silicon-containing resin and (S) a solvent, in which the (A) silicon-containing resin is one or more selected from the group consisting of a siloxane resin and a polysilane, and the (S) solvent contains a cycloalkyl acetate with a particular structure. Thus, the present invention has now been completed. More specifically, the present invention provides the following.

A first aspect of the present invention is a silicon-containing resin composition comprising (A) a silicon-containing resin and (S) a solvent, the (A) silicon-containing resin being one or more selected from the group consisting of a siloxane resin and a polysilane, the (S) solvent containing a cycloalkyl acetate represented by the following formula (S1):

[Chem. 1]

(in the formula (S1), $R^{s1}$ represents an alkyl group having 1 to 3 carbon atoms; p is an integer of 1 to 6; and q is an integer of 0 to (p+1)).

A second aspect of the present invention is a method for forming a silica-based coating film, comprising:

applying the silicon-containing resin composition described in the first aspect to a substrate to form a coating film; and baking the coating film.

Effects of the Invention

The present invention can provide a silicon-containing resin composition capable of forming a silica-based coating film with inhibited crack formation, a method for forming a silica-based coating film using the silicon-containing resin composition, and a crack-free silica-based coating film formed using the silicon-containing resin composition.

PREFERRED MODE FOR CARRYING OUT THE INVENTION

<Silicon-Containing Resin Composition>

A silicon-containing resin composition according to the present invention comprises (A) a silicon-containing resin and (S) a solvent. As the (A) silicon-containing resin, one or more selected from a siloxane resin and a polysilane is used. The (S) solvent contains a cycloalkyl acetate represented by the following formula (S1).

[Chem. 2]

(In the formula (S1), $R^{s1}$ represents an alkyl group having 1 to 3 carbon atoms; p is an integer of 1 to 6; and q is an integer of 0 to (p+1).)

When the silicon-containing resin composition comprises the solvent (S) that contains a cycloalkyl acetate with a predetermined structure, crack formation in a silica-based coating film that is formed by using the silicon-containing resin composition tends to be inhibited. Particularly when the film thickness of a silica-based coating film formed by using a silicon-containing resin composition is as great as about 2.0 to 20 μm (particularly about 5.0 to 20 μm), cracks tend to form. By using the silicon-containing resin composition according to the present invention, crack formation tends to be inhibited even when the film thickness of the resulting silica-based coating film is as great as about 2.0 to 20 μm (particularly about 5.0 to 20 μm).

Next, essential or optional components of the silicon-containing resin composition will be described.

[(A) Silicon-Containing Resin]

As the (A) silicon-containing resin, one or more selected from a siloxane resin and a polysilane is used. By baking a film containing the (A) silicon-containing resin, a silica-based film is obtained. Next, the siloxane resin and the polysilane are described.

(Siloxane Resin)

The siloxane resin is not particularly limited as far as it is a type of resin that is soluble in the (S) solvent containing a cycloalkyl acetate with a structure described below. As the siloxane resin, a siloxane resin that is obtained by hydrolysis and condensation of at least one type selected from a silane compound represented by the following formula (A1) is suitably used, for example.

   (A1)

In the formula (A1), R represents a hydrogen atom, an alkyl group, an aryl group, or an aralkyl group, R' represents an alkyl group or a phenyl group, and n represents an integer of 2 to 4. When a plurality of Rs are bonded to Si, the plurality of Rs may be the same or different from each other. A plurality of (OR') groups bonded to Si may also be the same or different from each other.

The alkyl group as R is preferably a straight chain or branched alkyl group having 1 to 20 carbon atoms, more preferably a straight chain or branched alkyl group having 1 to 4 carbon atoms.

When R is an aryl group or an aralkyl group, the aryl groups contained in these groups are not particularly limited as far as objects of the present invention are not inhibited. Examples of a suitable aryl group include the following groups.

[Chem. 3]

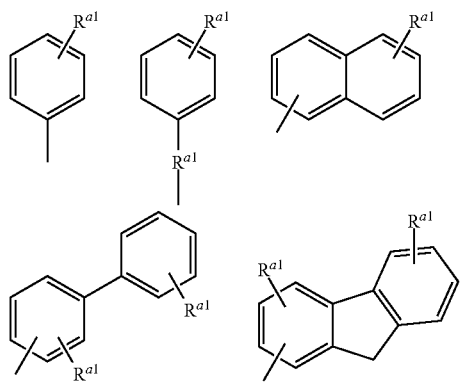

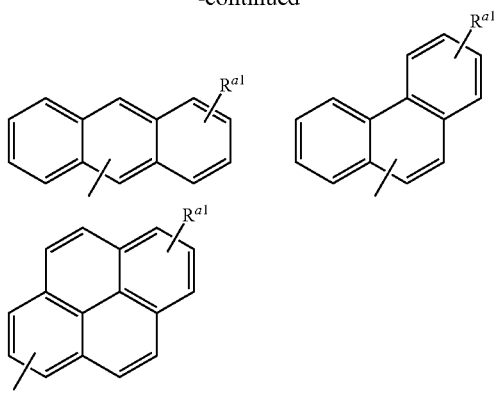

Among the groups represented by the above formulas, groups represented by the following formulas are preferable.

[Chem. 4]

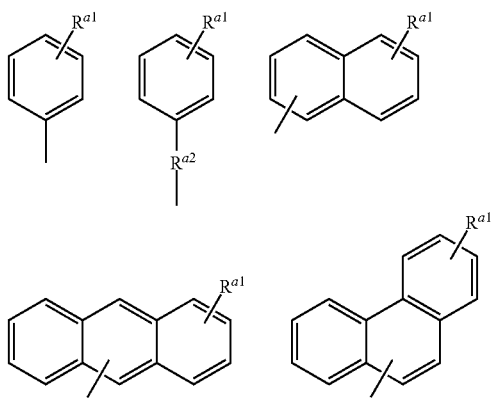

In the above formulas, $R^{a1}$ represents a hydrogen atom; a hydroxy group; an alkoxy group such as a methoxy group, an ethoxy group, a butoxy group, or a propoxy group; or a hydrocarbon group such as a methyl group, an ethyl group, a butyl group, or a propyl group. In the above formulas, $R^{a2}$ represents an alkylene group such as a methylene group, an ethylene group, a propylene group, or a butylene group.

When R is an aryl group or an aralkyl group, specific and suitable examples include a benzyl group, a phenethyl group, a phenyl group, a naphthyl group, an anthracenyl group, a phenanthryl group, a biphenylyl group, a fluorenyl group, and a pyrenyl group.

The number of benzene rings in the aryl group or the aralkyl group is preferably 1 to 3. When the number of benzene rings is 1 to 3, production of the siloxane resin proceeds well, the resulting high degree of polymerization of the siloxane resin inhibits volatilization during baking, and thereby the silica-based coating film is easily formed. The aryl group or the aralkyl group may contain a hydroxy group as a substituent.

The alkyl group as R' is preferably a straight chain or branched alkyl group having 1 to 5 carbon atoms. The number of carbon atoms in the alkyl group as R' is preferably 1 or 2 particularly in terms of the hydrolysis rate. When n is 4 in the formula (A1), the resulting silane compound (i) is represented by the following formula (A2).

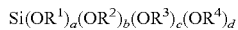   (A2)

In the formula (A2), $R^1$, $R^2$, $R^3$, and $R^4$ each independently represent the same alkyl group or the same phenyl group as in R' above.

a, b, c, and d are integers that satisfy $0 \leq a \leq 4$, $0 \leq b \leq 4$, $0 \leq c \leq 4$, $0 \leq d \leq 4$, and $a+b+c+d=4$.

When n is 3 in the formula (A1), the resulting silane compound (ii) is represented by the following formula (A3).

$$R^5Si(OR^6)_e(OR^7)_f(OR^8)_g \quad (A3)$$

In the formula (A3), $R^5$ represents a hydrogen atom or the same alkyl group, the same aryl group, or the same aralkyl group as in R above; and
$R^6$, $R^7$, and $R^8$ each independently represent the same alkyl group or the same phenyl group as in R' above.

e, f, and g are integers that satisfy $0 \leq e \leq 3$, $0 \leq f \leq 3$, $0 \leq g \leq 3$, and $e+f+g=3$.

When n is 2 in the formula (A1), the resulting silane compound (iii) is represented by the following formula (A4).

$$R^9R^{10}Si(OR^{11})_h(OR^{12})_i \quad (A4)$$

In the formula (A4), $R^9$ and $R^{10}$ represent a hydrogen atom or the same alkyl group, the same aryl group, or the same aralkyl group as in R above; and
$R^{11}$ and $R^{12}$ each independently represent the same alkyl group or the same phenyl group as in R' above.

h and i are integers that satisfy $0 \leq h \leq 2$, $0 \leq i \leq 2$, and $h+i=2$.

Specific examples of the silane compound (i) include tetraalkoxysilanes such as tetramethoxysilane, tetraethoxysilane, tetrapropoxysilane, tetrabutoxysilane, tetrapentyloxysilane, tetraphenyloxysilane, trimethoxymonoethoxysilane, dimethoxydiethoxysilane, triethoxymonomethoxysilane, trimethoxymonopropoxysilane, monomethoxytributoxysilane, monomethoxytripentyloxysilane, monomethoxytriphenyloxysilane, dimethoxydipropoxysilane, tripropoxymonomethoxysilane, trimethoxymonobutoxysilane, dimethoxydibutoxysilane, triethoxymonopropoxysilane, diethoxydipropoxysilane, tributoxymonopropoxysilane, dimethoxymonoethoxymonobutoxysilane, diethoxymonomethoxymonobutoxysilane, diethoxymonopropoxymonobutoxysilane, dipropoxymonomethoxymonoethoxysilane, dipropoxymonomethoxymonobutoxysilane, dipropoxymonoethoxymonobutoxysilane, dibutoxymonomethoxymonoethoxysilane, dibutoxymonoethoxymonopropoxysilane, and monomethoxymonoethoxymonopropoxymonobutoxysilane. Among these, tetramethoxysilane and tetraethoxysilane are preferable.

Specific examples of the silane compound (ii) include hydrosilane compounds such as trimethoxysilane, triethoxysilane, tripropoxysilane, tripentyloxysilane, triphenyloxysilane, dimethoxymonoethoxysilane, diethoxymonomethoxysilane, dipropoxymonomethoxysilane, dipropoxymonoethoxysilane, dipentyloxylmonomethoxysilane, dipentyloxymonoethoxysilane, dipentyloxymonopropoxysilane, diphenyloxylmonomethoxysilane, diphenyloxymonoethoxysilane, diphenyloxymonopropoxysilane, methoxyethoxypropoxysilane, monopropoxydimethoxysilane, monopropoxydiethoxysilane, monobutoxydimethoxysilane, monopentyloxydiethoxysilane, and monophenyloxydiethoxysilane; methylsilane compounds such as methyltrimethoxysilane, methyltriethoxysilane, methyltripropoxysilane, methyltripentyloxysilane, methyltriphenyloxysilane, methylmonomethoxydiethoxysilane, methylmonomethoxydipropoxysilane, methylmonomethoxydipentyloxysilane, methylmonomethoxydiphenyloxysilane, methylmethoxyethoxypropoxysilane, and methylmonomethoxymonoethoxymonobutoxysilane; ethylsilane compounds such as ethyltrimethoxysilane, ethyltriethoxysilane, ethyltripropoxysilane, ethyltripentyloxysilane, ethyltriphenyloxysilane, ethylmonomethoxydiethoxysilane, ethylmonomethoxydipropoxysilane, ethylmonomethoxydipentyloxysilane, ethylmonomethoxydiphenyloxysilane, ethylmethoxyethoxypropoxysilane, and ethylmonomethoxymonoethoxymonobutoxysilane; propylsilane compounds such as propyltrimethoxysilane, propyltriethoxysilane, propyltripropoxysilane, propyltripentyloxysilane, and propyltriphenyloxysilane, propylmonomethoxydiethoxysilane, propylmonomethoxydipropoxysilane, propylmonomethoxydipentyloxysilane, propylmonomethoxydiphenyloxysilane, propylmethoxyethoxypropoxysilane, and propylmonomethoxymonoethoxymonobutoxysilane; butylsilane compounds such as butyltrimethoxysilane, butyltriethoxysilane, butyltripropoxysilane, butyltripentyloxysilane, butyltriphenyloxysilane, butylmonomethoxydiethoxysilane, butylmonomethoxydipropoxysilane, butylmonomethoxydipentyloxysilane, butylmonomethoxydiphenyloxysilane, butylmethoxyethoxypropoxysilane, and butylmonomethoxymonoethoxymonobutoxysilane; phenylsilane compounds such as phenyltrimethoxysilane, phenyltriethoxysilane, phenyltripropoxysilane, phenyltripentyloxysilane, phenyltriphenyloxysilane, phenylmonomethoxydiethoxysilane, phenylmonomethoxydipropoxysilane, phenylmonomethoxydipentyloxysilane, phenylmonomethoxydiphenyloxysilane, phenylmethoxyethoxypropoxysilane, and phenylmonomethoxymonoethoxymonobutoxysilane; hydroxyphenylsilane compounds such as hydroxyphenyltrimethoxysilane, hydroxyphenyltriethoxysilane, hydroxyphenyltripropoxysilane, hydroxyphenyltripentyloxysilane, hydroxyphenyltriphenyloxysilane, hydroxyphenylmonomethoxydiethoxysilane, hydroxyphenylmonomethoxydipropoxysilane, hydroxyphenylmonomethoxydipentyloxysilane, hydroxyphenylmonomethoxydiphenyloxysilane, hydroxyphenylmethoxyethoxypropoxysilane, and hydroxyphenylmonomethoxymonoethoxymonobutoxysilane; naphthylsilane compounds such as naphthyltrimethoxysilane, naphthyltriethoxysilane, naphthyltripropoxysilane, naphthyltripentyloxysilane, naphthyltriphenyloxysilane, naphthylmonomethoxydiethoxysilane, naphthylmonomethoxydipropoxysilane, naphthylmonomethoxydipentyloxysilane, naphthylmonomethoxydiphenyloxysilane, naphthylmethoxyethoxypropoxysilane, and naphthylmonomethoxymonoethoxymonobutoxysilane; benzylsilane compounds such as benzyltrimethoxysilane, benzyltriethoxysilane, benzyltripropoxysilane, benzyltripentyloxysilane, benzyltriphenyloxysilane, benzylmonomethoxydiethoxysilane, benzylmonomethoxydipropoxysilane, benzylmonomethoxydipentyloxysilane, benzylmonomethoxydiphenyloxysilane, benzylmethoxyethoxypropoxysilane, and benzylmonomethoxymonoethoxymonobutoxysilane; and
hydroxybenzylsilane compounds such as hydroxybenzyltrimethoxysilane, hydroxybenzyltriethoxysilane, hydroxybenzyltripropoxysilane, hydroxybenzyltripentyloxysilane, hydroxybenzyltriphenyloxysilane, hydroxybenzylmonomethoxydiethoxysilane, hydroxybenzylmonomethoxydipropoxysilane, hydroxybenzylmonomethoxydipentyloxysilane, hydroxybenzylmonomethoxydiphenyloxysilane, hydroxybenzylmethoxyethoxypropoxysilane, and hydroxybenzylmonomethoxymonoethoxymonobutoxysilane.

Specific examples of the silane compound (iii) include hydrosilane compounds such as dimethoxysilane, diethoxysilane, dipropoxysilane, dipentyloxysilane, diphenyloxysilane, methoxyethoxysilane, methoxypropoxysilane, methoxypentyloxysilane, methoxyphenyloxysilane, ethoxypropoxysilane, ethoxypentyloxysilane, and ethoxyphenyloxysilane;

methylhydrosilane compounds such as methyldimethoxysilane, methylmethoxyethoxysilane, methyldiethoxysilane, methylmethoxypropoxysilane, methylmethoxypentyloxysilane, methylethoxypropoxysilane, methyldipropoxysilane, methyldipentyloxysilane, methyldiphenyloxysilane, and methylmethoxyphenyloxysilane;

ethylhydrosilane compounds such as ethyldimethoxysilane, ethylmethoxyethoxysilane, ethyldiethoxysilane, ethylmethoxypropoxysilane, ethylmethoxypentyloxysilane, ethylethoxypropoxysilane, ethyldipropoxysilane, ethyldipentyloxysilane, ethyldiphenyloxysilane, and ethylmethoxyphenyloxysilane;

propylhydrosilane compounds such as propyldimethoxysilane, propylmethoxyethoxysilane, propyldiethoxysilane, propylmethoxypropoxysilane, propylmethoxypentyloxysilane, propylethoxypropoxysilane, propyldipropoxysilane, propyldipentyloxysilane, propyldiphenyloxysilane, and propylmethoxyphenyloxysilane;

butylhydrosilane compounds such as butyldimethoxysilane, butylmethoxyethoxysilane, butyldiethoxysilane, butylmethoxypropoxysilane, butylmethoxypentyloxysilane, butylethoxypropoxysilane, butyldipropoxysilane, butyldipentyloxysilane, butyldiphenyloxysilane, and butylmethoxyphenyloxysilane;

phenylhydrosilane compounds such as phenyldimethoxysilane, phenylmethoxyethoxysilane, phenyldiethoxysilane, phenylmethoxypropoxysilane, phenylmethoxypentyloxysilane, phenylethoxypropoxysilane, phenyldipropoxysilane, phenyldipentyloxysilane, phenyldiphenyloxysilane, and phenylmethoxyphenyloxysilane;

hydroxyphenylhydrosilane compounds such as hydroxyphenyldimethoxysilane, hydroxyphenylmethoxyethoxysilane, hydroxyphenyldiethoxysilane, hydroxyphenylmethoxypropoxysilane, hydroxyphenylmethoxypentyloxysilane, hydroxyphenylethoxypropoxysilane, hydroxyphenyldipropoxysilane, hydroxyphenyldipentyloxysilane, hydroxyphenyldiphenyloxysilane, and hydroxyphenylmethoxyphenyloxysilane;

naphthylhydrosilane compounds such as naphthyldimethoxysilane, naphthylmethoxyethoxysilane, naphthyldiethoxysilane, naphthylmethoxypropoxysilane, naphthylmethoxypentyloxysilane, naphthylethoxypropoxysilane, naphthyldipropoxysilane, naphthyldipentyloxysilane, naphthyldiphenyloxysilane, and naphthylmethoxyphenyloxysilane;

benzylhydrosilane compounds such as benzyldimethoxysilane, benzylmethoxyethoxysilane, benzyldiethoxysilane, benzylmethoxypropoxysilane, benzylmethoxypentyloxysilane, benzylethoxypropoxysilane, benzyldipropoxysilane, benzyldipentyloxysilane, benzyldiphenyloxysilane, and benzylmethoxyphenyloxysilane;

hydroxybenzylhydrosilane compounds such as hydroxybenzyldimethoxysilane, hydroxybenzylmethoxyethoxysilane, hydroxybenzyldiethoxysilane, hydroxybenzylmethoxypropoxysilane, hydroxybenzylmethoxypentyloxysilane, hydroxybenzylethoxypropoxysilane, hydroxybenzyldipropoxysilane, hydroxybenzyldipentyloxysilane, hydroxybenzyldiphenyloxysilane, and hydroxybenzylmethoxyphenyloxysilane;

dimethylsilane compounds such as dimethyldimethoxysilane, dimethylmethoxyethoxysilane, dimethylmethoxypropoxysilane, dimethyldiethoxysilane, dimethyldipentyloxysilane, dimethyldiphenyloxysilane, dimethylethoxypropoxysilane, and dimethyldipropoxysilane;

diethylsilane compounds such as diethyldimethoxysilane, diethylmethoxyethoxysilane, diethylmethoxypropoxysilane, diethyldiethoxysilane, diethyldipentyloxysilane, diethyldiphenyloxysilane, diethylethoxypropoxysilane, and diethyldipropoxysilane;

dipropoxysilane compounds such as dipropyldimethoxysilane, dipropylmethoxyethoxysilane, dipropylmethoxypropoxysilane, dipropyldiethoxysilane, dipropyldipentyloxysilane, dipropyldiphenyloxysilane, dipropylethoxypropoxysilane, and dipropyldipropoxysilane;

dibutylsilane compounds such as dibutyldimethoxysilane, dibutylmethoxyethoxysilane, dibutylmethoxypropoxysilane, dibutyldiethoxysilane, dibutyldipentyloxysilane, dibutyldiphenyloxysilane, dibutylethoxypropoxysilane, and dibutyldipropoxysilane;

diphenylsilane compounds such as diphenyldimethoxysilane, diphenylmethoxyethoxysilane, diphenylmethoxypropoxysilane, diphenyldiethoxysilane, diphenyldipentyloxysilane, diphenyldiphenyloxysilane, diphenylethoxypropoxysilane, and diphenyldipropoxysilane;

di(hydroxyphenyl)silane compounds such as di(hydroxyphenyl)dimethoxysilane, di(hydroxyphenyl)methoxyethoxysilane, di(hydroxyphenyl)methoxypropoxysilane, di(hydroxyphenyl)diethoxysilane, di(hydroxyphenyl)dipentyloxysilane, di(hydroxyphenyl)diphenyloxysilane, di(hydroxyphenyl)ethoxypropoxysilane, and di(hydroxyphenyl)dipropoxysilane;

dinaphthylsilane compounds such as dinaphthyldimethoxysilane, dinaphthylmethoxyethoxysilane, dinaphthylmethoxypropoxysilane, dinaphthyldiethoxysilane, dinaphthyldipentyloxysilane, dinaphthyldiphenyloxysilane, dinaphthylethoxypropoxysilane, and dinaphthyldipropoxysilane;

dibenzylsilane compounds such as dibenzyldimethoxysilane, dibenzylmethoxyethoxysilane, dibenzylmethoxypropoxysilane, dibenzyldiethoxysilane, dibenzyldipentyloxysilane, dibenzyldiphenyloxysilane, dibenzylethoxypropoxysilane, and dibenzyldipropoxysilane;

di(hydroxybenzyl)silane compounds such as di(hydroxybenzyl)dimethoxysilane, di(hydroxybenzyl)methoxyethoxysilane, di(hydroxybenzyl)methoxypropoxysilane, di(hydroxybenzyl)diethoxysilane, di(hydroxybenzyl)dipentyloxysilane, di(hydroxybenzyl)diphenyloxysilane, di(hydroxybenzyl)ethoxypropoxysilane, and di(hydroxybenzyl)dipropoxysilane;

methylethylsilane compounds such as methylethyldimethoxysilane, methylethylmethoxyethoxysilane, methylethylmethoxypropoxysilane, methylethyldiethoxysilane, methylethyldipentyloxysilane, methylethyldiphenyloxysilane, methylethylethoxypropoxysilane, and methylethyldipropoxysilane;

methylpropylsilane compounds such as methylpropyldimethoxysilane, methylpropylmethoxyethoxysilane, methylpropylmethoxypropoxysilane, methylpropyldiethoxysilane, methylpropyldipentyloxysilane, methylpropyldiphenyloxysilane, methylpropylethoxypropoxysilane, and methylpropyldipropoxysilane;

methylbutylsilane compounds such as methylbutyldimethoxysilane, methylbutylmethoxyethoxysilane, methylbutylmethoxypropoxysilane, methylbutyldiethoxysilane, methylbutyldipentyloxysilane, methylbutyldiphenyloxysilane, methylbutylethoxypropoxysilane, and methylbutyldipropoxysilane;

methyl(phenyl)silane compounds such as methyl(phenyl)dimethoxysilane, methyl(phenyl)methoxyethoxysilane, methyl(phenyl)methoxypropoxysilane, methyl(phenyl)diethoxysilane, methyl(phenyl)dipentyloxysilane, methyl(phenyl)diphenyloxysilane, methyl(phenyl)ethoxypropoxysilane, and methyl(phenyl)dipropoxysilane;

methyl(hydroxyphenyl)silane compounds such as methyl(hydroxyphenyl)dimethoxysilane, methyl(hydroxyphenyl)methoxyethoxysilane, methyl(hydroxyphenyl)methoxypropoxysilane, methyl(hydroxyphenyl)diethoxysilane, methyl(hydroxyphenyl)dipentyloxysilane, methyl(hydroxyphenyl)diphenyloxysilane, methyl(hydroxyphenyl)ethoxypropoxysilane, and methyl(hydroxyphenyl)dipropoxysilane;

methyl(naphthyl)silane compounds such as methyl(naphthyl)dimethoxysilane, methyl(naphthyl)methoxyethoxysilane, methyl(naphthyl)methoxypropoxysilane, methyl(naphthyl)diethoxysilane, methyl(naphthyl)dipentyloxysilane, methyl(naphthyl)diphenyloxysilane, methyl(naphthyl)ethoxypropoxysilane, and methyl(naphthyl)dipropoxysilane;

methyl(benzyl)silane compounds such as methyl(benzyl)dimethoxysilane, methyl(benzyl)methoxyethoxysilane, methyl(benzyl)methoxypropoxysilane, methyl(benzyl)diethoxysilane, methyl(benzyl)dipentyloxysilane, methyl(benzyl)diphenyloxysilane, methyl(benzyl)ethoxypropoxysilane, and methyl(benzyl)dipropoxysilane;

methyl(hydroxybenzyl)silane compounds such as methyl(hydroxybenzyl)dimethoxysilane, methyl(hydroxybenzyl)methoxyethoxysilane, methyl(hydroxybenzyl)methoxypropoxysilane, methyl(hydroxybenzyl)diethoxysilane, methyl(hydroxybenzyl)dipentyloxysilane, methyl(hydroxybenzyl)diphenyloxysilane, methyl(hydroxybenzyl)ethoxypropoxysilane, and methyl(hydroxybenzyl)dipropoxysilane;

ethylpropylsilane compounds such as ethylpropyldimethoxysilane, ethylpropylmethoxyethoxysilane, ethylpropylmethoxypropoxysilane, ethylpropyldiethoxysilane, ethylpropyldipentyloxysilane, ethylpropyldiphenyloxysilane, ethylpropylethoxypropoxysilane, and ethylpropyldipropoxysilane;

ethylbutylsilane compounds such as ethylbutyldimethoxysilane, ethylbutylmethoxyethoxysilane, ethylbutylmethoxypropoxysilane, ethylbutyldiethoxysilane, ethylbutyldipentyloxysilane, ethylbutyldiphenyloxysilane, ethylbutylethoxypropoxysilane, and ethylbutyldipropoxysilane;

ethyl(phenyl)silane compounds such as ethyl(phenyl)dimethoxysilane, ethyl(phenyl)methoxyethoxysilane, ethyl(phenyl)methoxypropoxysilane, ethyl(phenyl)diethoxysilane, ethyl(phenyl)dipentyloxysilane, ethyl(phenyl)diphenyloxysilane, ethyl(phenyl)ethoxypropoxysilane, and ethyl(phenyl)dipropoxysilane;

ethyl(hydroxyphenyl)silane compounds such as ethyl(hydroxyphenyl)dimethoxysilane, ethyl(hydroxyphenyl)methoxyethoxysilane, ethyl(hydroxyphenyl)methoxypropoxysilane, ethyl(hydroxyphenyl)diethoxysilane, ethyl(hydroxyphenyl)dipentyloxysilane, ethyl(hydroxyphenyl)diphenyloxysilane, ethyl(hydroxyphenyl)ethoxypropoxysilane, and ethyl(hydroxyphenyl)dipropoxysilane;

ethyl(naphthyl)silane compounds such as ethyl(naphthyl)dimethoxysilane, ethyl(naphthyl)methoxyethoxysilane, ethyl(naphthyl)methoxypropoxysilane, ethyl(naphthyl)diethoxysilane, ethyl(naphthyl)dipentyloxysilane, ethyl(naphthyl)diphenyloxysilane, ethyl(naphthyl)ethoxypropoxysilane, and ethyl(naphthyl)dipropoxysilane;

ethyl(benzyl)silane compounds such as ethyl(benzyl)dimethoxysilane, ethyl(benzyl)methoxyethoxysilane, ethyl(benzyl)methoxypropoxysilane, ethyl(benzyl)diethoxysilane, ethyl(benzyl)dipentyloxysilane, ethyl(benzyl)diphenyloxysilane, ethyl(benzyl)ethoxypropoxysilane, and ethyl(benzyl)dipropoxysilane;

ethyl(hydroxybenzyl)silane compounds such as ethyl(hydroxybenzyl)dimethoxysilane, ethyl(hydroxybenzyl)methoxyethoxysilane, ethyl(hydroxybenzyl)methoxypropoxysilane, ethyl(hydroxybenzyl)diethoxysilane, ethyl(hydroxybenzyl)dipentyloxysilane, ethyl(hydroxybenzyl)diphenyloxysilane, ethyl(hydroxybenzyl)ethoxypropoxysilane, and ethyl(hydroxybenzyl)dipropoxysilane;

propylbutylsilane compounds such as propylbutyldimethoxysilane, propylbutylmethoxyethoxysilane, propylbutylmethoxypropoxysilane, propylbutyldiethoxysilane, propylbutyldipentyloxysilane, propylbutyldiphenyloxysilane, propylbutylethoxypropoxysilane, and propylbutyldipropoxysilane;

propyl(phenyl)silane compounds such as propyl(phenyl)dimethoxysilane, propyl(phenyl)methoxyethoxysilane, propyl(phenyl)methoxypropoxysilane, propyl(phenyl)diethoxysilane, propyl(phenyl)dipentyloxysilane, propyl(phenyl)diphenyloxysilane, propyl(phenyl)ethoxypropoxysilane, and propyl(phenyl)dipropoxysilane; propyl(hydroxyphenyl)silane compounds such as propyl(hydroxyphenyl)dimethoxysilane, propyl(hydroxyphenyl)methoxyethoxysilane, propyl(hydroxyphenyl)methoxypropoxysilane, propyl(hydroxyphenyl)diethoxysilane, propyl(hydroxyphenyl)dipentyloxysilane, propyl(hydroxyphenyl)diphenyloxysilane, propyl(hydroxyphenyl)ethoxypropoxysilane, and propyl(hydroxyphenyl)dipropoxysilane;

propyl(naphthyl)silane compounds such as propyl(naphthyl)dimethoxysilane, propyl(naphthyl)methoxyethoxysilane, propyl(naphthyl)methoxypropoxysilane, propyl(naphthyl)diethoxysilane, propyl(naphthyl)dipentyloxysilane, propyl(naphthyl)diphenyloxysilane, propyl(naphthyl)ethoxypropoxysilane, and propyl(naphthyl)dipropoxysilane;

propyl(benzyl)silane compounds such as propyl(benzyl)dimethoxysilane, propyl(benzyl)methoxyethoxysilane, propyl(benzyl)methoxypropoxysilane, propyl(benzyl)diethoxysilane, propyl(benzyl)dipentyloxysilane, propyl(benzyl)diphenyloxysilane, propyl(benzyl)ethoxypropoxysilane, and propyl(benzyl)dipropoxysilane; and propyl(hydroxybenzyl)silane compounds such as propyl(hydroxybenzyl)dimethoxysilane, propyl(hydroxybenzyl)methoxyethoxysilane, propyl(hydroxybenzyl)methoxypropoxysilane, propyl(hydroxybenzyl)diethoxysilane, propyl(hydroxybenzyl)dipentyloxysilane, propyl(hydroxybenzyl)diphenyloxysilane, propyl(hydroxybenzyl)ethoxypropoxysilane, and propyl(hydroxybenzyl)dipropoxysilane.

By subjecting the silane compound described above to hydrolysis and condensation by a conventional procedure, the siloxane resin is obtained. The mass average molecular weight of the siloxane resin is preferably 300 to 30000, more preferably 500 to 10000. Two or more siloxane resins having different mass average molecular weights may be mixed together. When the mass average molecular weight of the siloxane resin is within the above range, a silicon-containing resin composition having excellent film-forming properties and capable of forming a flat silica-based coating film tends to be obtained.

Examples of a suitable siloxane resin obtained by hydrolysis and condensation of the silane compound described above include a siloxane resin having a structural unit represented by the following formula (a-1). In the siloxane resin, the number of carbon atoms per one silicon atom is two or more.

[Chem. 5]

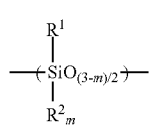

(a-1)

(In the formula (a-1), $R^1$ represents an alkyl group, an aryl group, or an aralkyl group; $R^2$ represents hydrogen, an alkyl group, an aryl group, or an aralkyl group; and m is 0 or 1.)

The alkyl group, the aryl group, or the aralkyl group in each of $R^1$ and $R^2$ is the same as the alkyl group, the aryl group, or the aralkyl group in the above formula (A1). By using the siloxane resin having an alkyl group, an aryl group, or an aralkyl group described above, the resulting silicon-containing resin composition tends to be capable of forming a silica-based coating film with excellent durability and be easily filled into a very small space.

The alkyl group is preferably an alkyl group having 1 to 5 carbon atoms, and examples thereof include a methyl group, an ethyl group, an n-propyl group, an i-propyl group, an n-butyl group, and a tert-butyl group. When an alkyl group having 1 to 5 carbon atoms is contained, a silica-based coating film with excellent heat resistance tends to be formed. Examples of the aryl group and the aralkyl group include a benzyl group, a phenethyl group, a phenyl group, a naphthyl group, an anthracenyl group, a phenanthryl group, a biphenyl group, a fluorenyl group, and a pyrenyl group.

Specific and preferable examples of the aryl group and the aralkyl group include those having the following structure.

[Chem. 6]

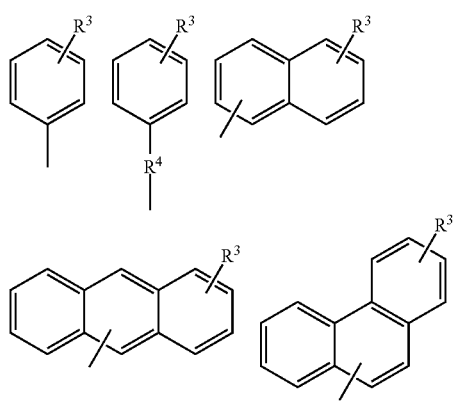

In the above formula, $R^3$ represents a hydrogen atom; a hydroxy group; an alkoxy group such as a methoxy group, an ethoxy group, a butoxy group, or a propoxy group; or a hydrocarbon group such as a methyl group, an ethyl group, a butyl group, or a propyl group, and $R^4$ represents an alkylene group such as a methylene group, an ethylene group, a propylene group, or a butylene group. The aromatic hydrocarbon group needs to have $R^3$ described above on at least one aromatic ring in the aromatic hydrocarbon group, and may have a plurality of $R^3$s. When a plurality of $R^3$s are contained, these $R^3$s may be the same or different from each other.

A group that is particularly preferable as $R^1$ is preferably a group having the following structure ($R^1$-a) or ($R^1$-b), particularly preferably ($R^1$-b).

[Chem. 7]

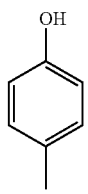

($R^1$-a)

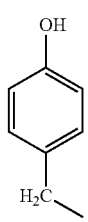

($R^1$-b)

In the formula (a-1), m is preferably 0. In this case, the siloxane resin has a silsesquioxane skeleton. The siloxane resin is more preferably a ladder-type silsesquioxane.

The structural unit (unit skeleton) represented by the formula (a-1) preferably has 2 or more and 15 or less carbon atoms per one silicon atom.

The siloxane resin may have two or more structural units (a-1). The siloxane resin may also have a combination of siloxane resins represented by different structural units (a-1). Specific examples of the siloxane resin having two or more structural units (a-1) include siloxane resins represented by the following structural formulas (A-1-1) to (A-1-3).

[Chem. 8]

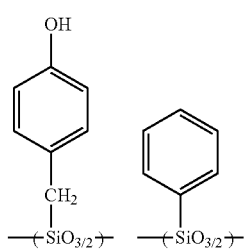

(A-1-1)

[Chem. 9]

(A-1-2)

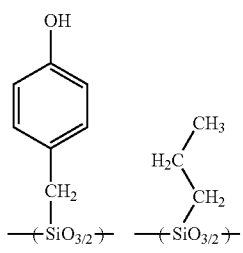

[Chem. 10]

(A-1-3)

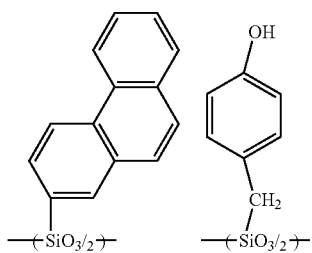

The siloxane resin may have, for example, a constituting unit represented by the following formula (A-1-4).

[Chem. 11]

(A-1-4)

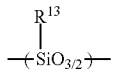

In the formula (A-1-4), $R^{13}$ represents an organic group having at least one group selected from the group consisting of a (meth)acrylic group, a vinyl group, and an epoxy group in the structure. The at least one group selected from the group consisting of a (meth)acrylic group, a vinyl group, and an epoxy group may be bonded to an Si atom directly or via a linking group. The linking group may be, for example, a straight chain or branched chain alkylene group having 1 to 10 carbon atoms, a straight chain or branched chain arylene group having 1 to 10 carbon atoms, or a divalent group in which these groups are combined. The linking group may have an ether bond, an amino bond, or an amide bond.

Examples of a constituting unit represented by (A-1-4) include, but are not limited to, the following ones.

[Chem. 12]

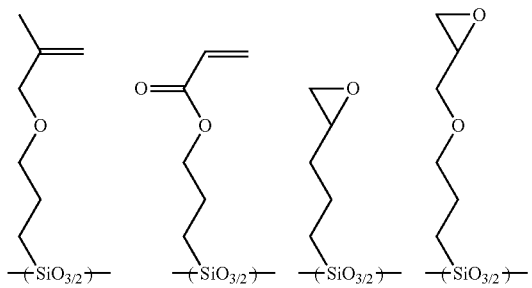

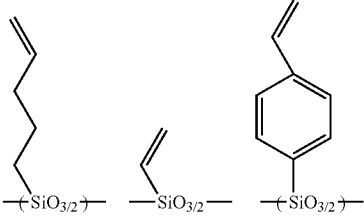

When $R^{13}$ has an epoxy group, examples of suitable $R^{13}$ include a 2-(3,4-epoxycyclohexyl)ethyl group and a 2-(3,4-epoxycyclohexyl) propyl group.

The siloxane resin may have, for example, a constituting unit represented by the following formula (A-1-5).

[Chem. 13]

(A-1-5)

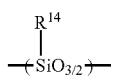

In the formula (A-1-5), $R^{14}$ represents an organic group having at least one carboxy group in the structure. The carboxy group is preferably bonded to an Si atom via a linking group, and the linking group is, for example, a straight chain or branched chain alkylene group having 1 to 10 carbon atoms, a straight chain or branched chain cycloalkylene group having 1 to 10 carbon atoms, a straight chain or branched chain arylene group having 1 to 10 carbon atoms, or a divalent group in which these groups are combined. The linking group may have an ether bond, an amino bond, an amide bond, or a vinyl bond, preferably an amide bond. Examples of $R^{14}$ include, but are not limited to, the following ones. In the following formulas, * represents the position where $R^{14}$ is bonded to Si in the formula (A-1-5).

[Chem. 14]

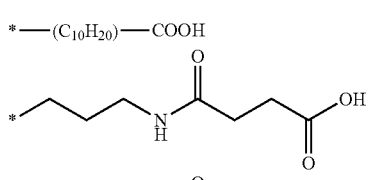
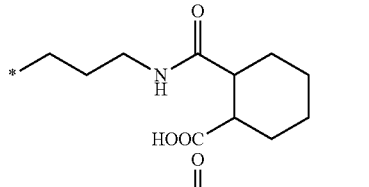
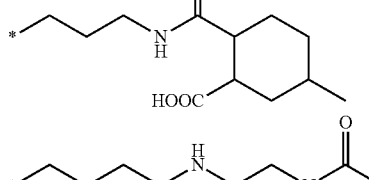
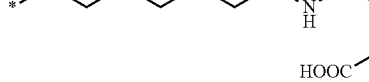

-continued

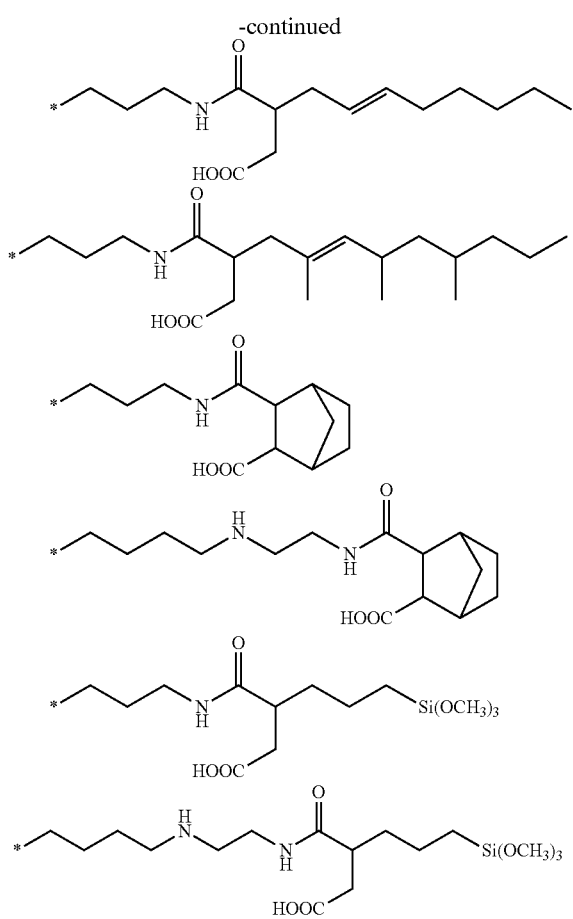

The silicon-containing resin composition may comprise (B) a curing agent. When the silicon-containing resin composition comprises the (B) curing agent and (i) when the (B) curing agent contains a curing agent that generates a base component by the action of light or heat, (ii) when the silicon-containing resin composition contains at least one selected from the group consisting of a photopolymerization initiator, an acid generator, and a base generator described below as other components, or (iii) when a method for film formation described below comprises an exposure step, the siloxane resin preferably has a constituting unit represented by (A-1-4). Similarly, in a case (iv) in which at least one (but except those corresponding to the (B) curing agent) selected from the group consisting of a photopolymerization initiator, an acid generator, and a base generator described below as other components is contained, the siloxane resin preferably has a constituting unit represented by (A-1-4). The proportion of a constituting unit represented by (A-1-4) in the siloxane resin is 10 to 80 mol %, for example. The siloxane resin may further have a structural unit represented by the formula (a-1) and/or a constituting unit represented by (A-1-5) as additional constituting units. The siloxane resin may have two or more types of a constituting unit represented by each formula.

When the method for film formation described below comprises a development step, the siloxane resin preferably has one or more constituting units selected from the group consisting of a constituting unit represented by (A-1-5), a constituting unit having a structure ($R^1$-a), and a constituting unit having a structure ($R^1$-b). The proportion of the constituting unit selected from the group consisting of a constituting unit represented by (A-1-5), a constituting unit having a structure ($R^1$-a), and a constituting unit having a structure ($R^1$-b) in the siloxane resin is 20 to 90 mol %, for example. In this case, the siloxane resin may further have a structural unit represented by the formula (a-1) and/or a constituting unit represented by (A-1-4) as additional constituting units, and the siloxane resin is preferably a siloxane resin having a constituting unit represented by (A-1-4) and a constituting unit represented by (A-1-5). The siloxane resin may have two or more types of a constituting unit represented by each formula.

(Polysilane)

The polysilane is not particularly limited as far as it is capable of forming a silica-based coating film when baked. The structure of the polysilane is not particularly limited. The polysilane may have any of a straight chain structure, a branched chain structure, a mesh structure, and a cyclic structure, and preferably has a chain structure, namely, a straight chain structure or a branched chain structure. The polysilane may have a silanol group and/or an alkoxy group. Examples of a suitable polysilane include a polysilane essentially having at least one of the units represented by the following formulas (A5) and (A6) and optionally having at least one unit selected from units represented by the following formulas (A7), (A8), and (A9). The polysilane may have a silanol group or an alkoxy group bonded to a silicon atom.

[Chem. 15]

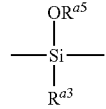
(A5)

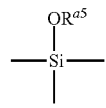
(A6)

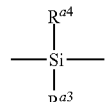
(A7)

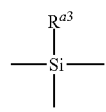
(A8)

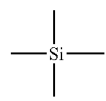
(A9)

(In the formulas (A5), (A7), and (A8), $R^{a3}$ and $R^{a4}$ each represent a hydrogen atom, an organic group, or a silyl group;
$R^{a5}$ represents a hydrogen atom or an alkyl group; and when $R^{a5}$ is an alkyl group, the alkyl group is preferably an alkyl group having 1 to 4 carbon atoms, more preferably a methyl group or an ethyl group.)

Examples of the organic group as $R^{a3}$ and $R^{a4}$ include hydrocarbon groups such as alkyl groups, alkenyl groups, cycloalkyl groups, cycloalkenyl groups, aryl groups, and aralkyl groups, alkoxy groups, alkenyloxy groups, cycloalkoxy groups, cycloalkenyloxy groups, aryloxy groups, and aralkyloxy groups. Among these groups, alkyl groups, aryl groups, and aralkyl groups are preferable. Examples of suitable alkyl groups, aryl groups, and aralkyl groups are the same as the alkyl groups, the aryl groups, and the aralkyl groups as R in the above formula (A1).

When each of $R^{a3}$ and $R^{a4}$ is a silyl group, examples of the silyl group include a silyl group and $Si_{1-10}$ silanyl groups (such as $Si_{1-6}$ silanyl groups) such as a disilanyl group and a trisilanyl group. The polysilane preferably has a unit of the following (A10) to (A13).

[Chem. 16]

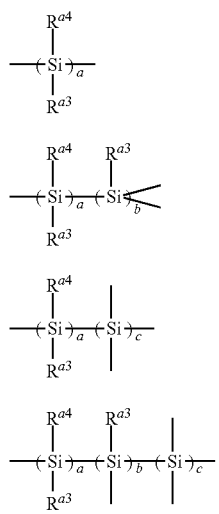

In (A10) to (A13), $R^{a3}$ and $R^{a4}$ are the same as $R^{a3}$ and $R^{a4}$ in the formulas (A5), (A7), and (A8). Each of a, b, and c is an integer of 2 to 1000. Each of a, b, and c is preferably 10 to 500, more preferably 10 to 100. The constituting unit in each unit may be present in the unit either in a random manner or as a block.

Among the polysilanes described above, a polysilane in which an alkyl group is bonded to a silicon atom and an aryl group or an aralkyl group is also bonded to a silicon atom or a polysilane in which an alkyl group alone is bonded to a silicon atom is preferable. More specifically, a polysilane in which a methyl group is bonded to a silicon atom and a benzyl group is also bonded to a silicon atom, a polysilane in which a methyl group is bonded to a silicon atom and a phenyl group is bonded to a silicon atom, or a polysilane in which a methyl group alone is bonded to a silicon atom is preferably used.

The mass average molecular weight of the polysilane is preferably 300 to 100000, more preferably 500 to 70000, further preferably 800 to 30000. Two or more polysilanes having different mass average molecular weights may be mixed together.

The content of the (A) silicon-containing resin in the silicon-containing resin composition is not particularly limited and may be determined depending on the desired film thickness. From the viewpoint of film-forming properties, the content of the (A) silicon-containing resin in the silicon-containing resin composition is preferably 1 to 50% by mass, more preferably 5 to 40% by mass, particularly preferably 10 to 35% by mass.

[(B) Curing Agent]

The silicon-containing resin composition may comprise the (B) curing agent. When the silicon-containing resin composition comprises the (B) curing agent, it is easy to form a silica-based coating film that has a low dielectric constant, is not readily subjected to dissolution, swelling, or deformation by the action of an organic solvent such as N-methyl-2-pyrrolidone, and has an excellent organic solvent resistance.

Examples of a suitable (B) curing agent include Brønsted acids such as hydrochloric acid, sulfuric acid, nitric acid, benzenesulfonic acid, and p-toluenesulfonic acid; imidazoles such as 2-methylimidazole and 2-ethyl-4-methylimidazole; organic amines such as 2,4,6-tris(dimethylaminomethyl)phenol, benzylmethylamine, DBU (1,8-diazabicyclo [5.4.0]-7-undecene), and DCMU (3-(3,4-dichlorophenyl)-1,1-dimethylurea); organophosphorus compounds such as tributylphosphine, triphenylphosphine, tris(p-tolyl)phosphine, tris(m-tolyl)phosphine, tris(o-tolyl)phosphine, diphenylcyclohexylphosphine, tricyclohexylphosphine, tris(dimethoxyphenyl)phosphine, ethyltriphenylphosphonium bromide, benzyltriphenylphosphonium chloride, and 1,4-bisdiphenylphosphinobutane; organophosphorus compound complexes such as triphenylphosphine triphenylborane, tetraphenylphosphonium tetra-p-tolyl borate, tetraphenylphosphonium tetraphenyl borate, tetraphenylphosphonium thiocyanate, tetraphenylphosphonium dicyanamide, and n-butyltriphenylphosphonium dicyanamide; complexes of a Lewis acid (such as boron trifluoride) and an organic amine (the organic amine is piperidine, for example); and amidines such as azabicycloundecene, diazabicycloundecene toluenesulfonic acid salt, and diazabicycloundecene octylic acid salt.

When the polysilane is used as the (A) component, it is preferable to use, in addition to the curing agent or alone, a curing agent that generates a base component by the action of light or heat.

(Curing Agent that Generates Base Component by Action of Heat)

The curing agent that generates a base component by the action of heat is not particularly limited as far as it is a compound conventionally used as a heat-responsive base generator. As the curing agent that generates a base component by the action of heat, 2-benzyl-2-dimethylamino-1-(4-morpholinophenyl)-butan-1-one may be used, for example. 2-benzyl-2-dimethylamino-1-(4-morpholinophenyl)-butan-1-one also generates a base by the action of light.

A compound that generates an imidazole compound represented by the following formula (B1) by the action of heat (hereinafter, this compound is also called a heat-responsive imidazole generator) is also preferably used as the curing agent.

[Chem. 17]

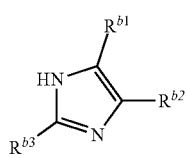

(In the formula (B1), $R^{b1}$, $R^{b2}$, and $R^{b3}$ each independently represent a hydrogen atom, a halogen atom, a hydroxy group, a mercapto group, a sulfide group, a silyl group, a silanol group, a nitro group, a nitroso group, a phosphino group, a sulfonato group, a phosphinyl group, a phosphonato group, or an organic group.)

As the organic group in $R^{b1}$, $R^{b2}$, and $R^{b3}$, an alkyl group, an alkenyl group, a cycloalkyl group, a cycloalkenyl group, an aryl group, an aralkyl group, and the like can be exemplified. The organic group can include a bond other than a hydrocarbon group such as a hetero atom, or a substituent. In addition, the organic group can be either a straight chain, a branched chain, or cyclic. The organic group is generally monovalent; however, it can also be an organic group of divalent or more in a case of forming a cyclic structure or the like.

$R^{b1}$ and $R^{b2}$ can bind to form a cyclic structure, and can further include a hetero atom bond. As the cyclic structure, a heterocycloalkyl group, a heteroaryl group and the like can be exemplified, and the cyclic structure can also be a condensed ring.

A bond included in the organic group of $R^{b1}$, $R^{b2}$, and $R^{b3}$ is not particularly limited as long as the effect of the present invention is not impaired. The organic group can include a bond including a hetero atom such as an oxygen atom, a nitrogen atom, a silicon atom and the like. Specific examples of the bond including a hetero atom include an ether bond, a thioether bond, a carbonyl bond, a thiocarbonyl bond, an ester bond, an amide bond, a urethane bond, an imino bond (—N=C(—R)—, —C(=NR)—: R representing a hydrogen atom or an organic group), a carbonate bond, a sulfonyl bond, a sulfinyl bond, an azo bond and the like.

As the bond including a hetero atom which can be included in the organic group of $R^{b1}$, $R^{b2}$, and $R^{b3}$, an ether bond, a thioether bond, a carbonyl bond, a thiocarbonyl bond, an ester bond, an amide bond, a urethane bond, an imino bond (—N=C(—R)—, —C(=NR)—: R representing a hydrogen atom or a monovalent organic group), a carbonate bond, a sulfonyl bond, and a sulfinyl bond are preferable from the viewpoint of thermal resistance of the imidazole compound.

In a case in which the organic group of $R^{b1}$, $R^{b2}$, and $R^{b3}$ is a substituent other than a hydrocarbon group, $R^{b1}$, $R^{b2}$, and $R^{b3}$ are not particularly limited as long as the effect of the present invention is not impaired. Specific examples of $R^{b1}$, $R^{b2}$, and $R^{b3}$ include a halogen atom, a hydroxyl group, a mercapto group, a sulfide group, a cyano group, an isocyano group, a cyanato group, an isocyanato group, a thiocyanato group, an isothiocyanato group, a silyl group, a silanol group, an alkoxy group, an alkoxycarbonyl group, a carbamoyl group, a thiocarbamoyl group, a nitro group, a nitroso group, a carboxylate group, an acyl group, an acyloxy group, a sulfino group, a sulfonato group, a phosphino group, a phosphinyl group, a phosphonato group, an alkyl ether group, an alkenylether group, an alkylthioether group, an alkenylthioether group, an arylether group, an arylthioether group and the like. The hydrogen atom included in the substituent can be substituted by a hydrocarbon group. The hydrocarbon group included in the abovementioned substituent can be either a straight chain, a branched chain, or cyclic.

As $R^{b1}$, $R^{b2}$, and $R^{b3}$, a hydrogen atom, an alkyl group having 1 to 12 carbon atoms, an aryl group having 1 to 12 carbon atoms, an alkoxy group having 1 to 12 carbon atoms, and a halogen atom are preferable, and a hydrogen atom is more preferable.

The heat-responsive imidazole generator is not particularly limited, as long as an imidazole compound represented by the formula (B1) is generated by the action of heat. Compounds which are used as a heat-responsive imidazole generator are obtained by replacing the skeleton originating from amines which are generated upon heating from the compounds (heat-responsive base generator) which are conventionally contained in various compositions and generate amines by the action of heat, with the skeleton originating from the imidazole compounds represented by the formula (B1).

Examples of the preferred heat-responsive imidazole generator include the compounds represented by the following formula (B2):

[Chem. 18]

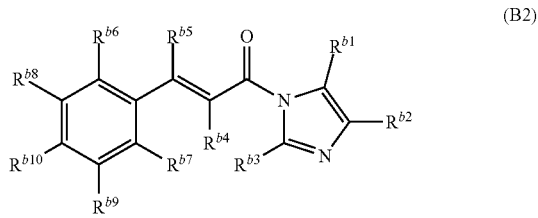

(B2)

wherein, in the formula (B2), $R^{b1}$, $R^{b2}$, and $R^{b3}$ each independently represent a hydrogen atom, a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group;

$R^{b4}$ and $R^{b5}$ each independently represent a hydrogen atom, a halogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, or an organic group;

$R^{b6}$, $R^{b7}$, $R^{b8}$, $R^{b9}$, and $R^{b10}$ each independently represent a hydrogen atom, a halogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group;

and two or more of $R^{b6}$, $R^{b7}$, $R^{b8}$, $R^{b9}$, and $R^{b10}$ may join together to form a cyclic structure, or may include a bond of a hetero atom.

In the formula (B2), $R^{b1}$, $R^{b2}$, and $R^{b3}$ are the same as those explained regarding the formula (B1).

In the formula (B2), $R^{b4}$ and $R^{b5}$ each represent independently a hydrogen atom, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group or an organic group.

As the organic group in $R^{b4}$ and $R^{b5}$, those listed for $R^{b1}$, $R^{b2}$, and $R^{b3}$ can be exemplified. The organic group can include a hetero atom, as in the case of $R^{b1}$, $R^{b2}$, and $R^{b3}$. The organic group can be either a straight chain, a branched chain, or cyclic.

Among the above, $R^{b4}$ and $R^{b5}$ are preferably, respectively independently a hydrogen atom, an alkyl group having 1 to 10 carbon atoms, a cycloalkyl group having 4 to 13 carbon atoms, a cycloalkenyl group having 4 to 13 carbon atoms, an aryloxy alkyl group having 7 to 16 carbon atoms, an aralkyl group having 7 to 20 carbon atoms, an alkyl group having 2 to 11 carbon atoms substituted with a cyano group, an alkyl group having 1 to 10 carbon atoms substituted with a hydroxyl group, an alkoxy group having 1 to 10 carbon atoms, an amido group having 2 to 11 carbon atoms, an alkylthio group having 1 to 10 carbon atoms, an acyl group having 1 to 10 carbon atoms, an ester group (—COOR, —OCOR: R representing a hydrocarbon group) having 2 to 11 carbon atoms, an aryl group having 6 to 20 carbon atoms, an aryl group having 6 to 20 carbon atoms in which an electron donating group and/or an electron withdrawing group are substituted, a benzyl group in which an electron-donating group and/or an electron withdrawing group are substituted, a cyano group, and a methylthio group. More preferably, $R^{b4}$ and $R^{b5}$ are both hydrogen atoms; or $R^{b4}$ is a methyl group and $R^{b5}$ is a hydrogen atom.

In the formula (B2), $R^{b6}$, $R^{b7}$, $R^{b8}$, $R^{b9}$, and $R^{b10}$ each independently represent a hydrogen atom, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group.

As the organic group in $R^{b6}$, $R^{b7}$, $R^{b8}$, $R^{b9}$, and $R^{b10}$, those listed for $R^{b1}$, $R^{b2}$, and $R^{b3}$ can be exemplified. As in the case of $R^{b1}$ and $R^{b2}$, the organic group can include a bond other than a hydrocarbon group such as a hetero atom, or a substituent. The organic group can be either a straight chain, a branched chain, or cyclic.

At least two of $R^{b6}$, $R^{b7}$, $R^{b8}$, $R^{b9}$, and $R^{b10}$ can bind to form a cyclic structure, and these can further include a bond of hetero atoms. As the cyclic structure, a heterocycloalkyl group, a heteroaryl group and the like can be exemplified, and the cyclic structure can also be a condensed ring. For example, $R^{b6}$, $R^{b7}$, $R^{b8}$, $R^{b9}$, and $R^{b10}$ can form a condensed ring such as naphthalene, anthracene, phenanthrene, indene and the like, through bonding of at least two of these and sharing of an atom of a benzene ring to which $R^{b6}$, $R^{b7}$, $R^{b8}$, $R^{b9}$, and $R^{b10}$ are bound.

Among the above, $R^{b6}$, $R^{b7}$, $R^{b8}$, $R^{b9}$, and $R^{b10}$ are each preferably independently a hydrogen atom, an alkyl group having 1 to 10 carbon atoms, a cycloalkyl group having 4 to 13 carbon atoms, a cycloalkenyl group having 4 to 13 carbon atoms, an aryloxy alkyl group having 7 to 16 carbon atoms, an aralkyl group having 7 to 20 carbon atoms, an alkyl group having 2 to 11 carbon atoms substituted with a cyano group, an alkyl group having 1 to 10 carbon atoms substituted with a hydroxyl group, an alkoxy group having 1 to 10 carbon atoms, an amido group having 2 to 11 carbon atoms, an alkylthio group having 1 to 10 carbon atoms, an acyl group having 1 to 10 carbon atoms, an ester group having 2 to 11 carbon atoms, an aryl group having 6 to 20 carbon atoms, an aryl group having 6 to 20 carbon atoms in which an electron donating group and/or an electron withdrawing group are substituted, a benzyl group in which an electron-donating group and/or an electron withdrawing group are substituted, a cyano group, a methylthio group and a nitro group.

A case where two or more of $R^{b6}$, $R^{b7}$, $R^{b8}$, $R^{b9}$, and $R^{b10}$ join together to form a condensed ring such as naphthalene, anthracene, phenanthrene and indene by sharing the atoms of the benzene ring to which $R^{b6}$, $R^{b7}$, $R^{b8}$, $R^{b9}$, and $R^{b10}$ are attached is preferred.

Among the compounds represented by the formula (B2), compounds represented by the following formula (B3);

[Chem. 19]

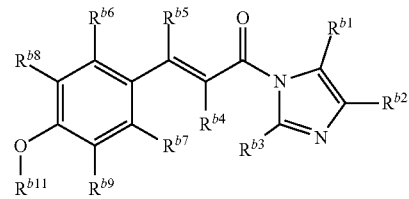

(B3)

wherein, in the formula (B3), $R^{b1}$, $R^{b2}$, and $R^{b3}$ are used synonymously with those in the formulas (B1) and (B2); $R^{b4}$ to $R^{b9}$ are used synonymously with those in the formula (B2);

$R^{b11}$ represents a hydrogen atom or an organic group;

$R^{c6}$ and $R^{b7}$ shall not be a hydroxyl group;

and two or more of $R^{b6}$, $R^{b7}$, $R^{b8}$, and $R^{b9}$ may join together to form a cyclic structure, or may include a bond of a hetero atom, are preferred.

The compounds represented by the formula (B3) have good solubility in organic solvents because they have a substituent —O—$R^{b11}$.

In the formula (B3), $R^{b11}$ is a hydrogen atom or an organic group. In a case where $R^{b11}$ is an organic group, those exemplified with regard to $R^{b1}$, $R^{b2}$, and $R^{b3}$ may be referred to as the organic group. This organic group may include a hetero atom in the organic group. This organic group may be either a straight chain, a branched chain, or cyclic. For $R^{b11}$, a hydrogen atom or an alkyl or alkoxyalkyl group having 1 to 12 carbon atoms is preferred, and a methyl group, an ethyl group, an n-propyl group, an i-propyl group, an n-butyl group, an i-butyl group, a t-butyl group, a methoxymethyl group, an ethoxymethyl group, a methoxyethyl group, an ethoxyethyl group, a propoxymethyl group, or a butoxymethyl group is more preferred.

Specific examples of the compounds particularly suitable for the heat-responsive imidazole generator are shown below.

[Chem. 20]

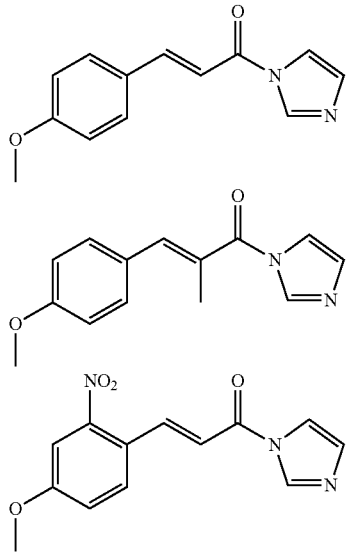

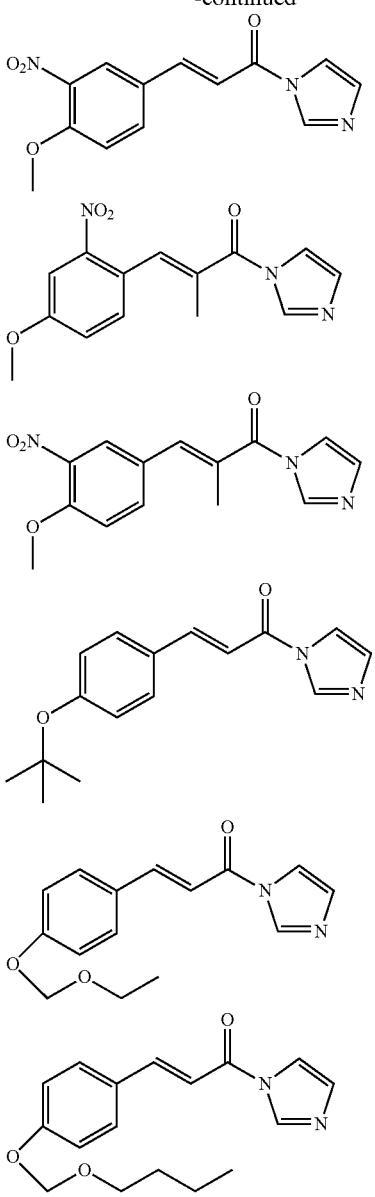

(Oxime Ester Compound)

An oxime ester compound degrades by the action of light and generates a base. Examples of a suitable oxime ester compound include a compound represented by the following formula (B4).

[Chem. 21]

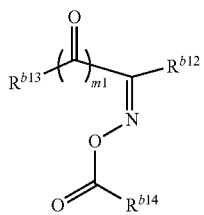

(B4)

In the formula (B4), $R^{b12}$ represents an alkyl group having 1 to 10 carbon atoms, an optionally substituted phenyl group, or an optionally substituted carbazolyl group;
m1 is 0 or 1;
$R^{b13}$ represents an optionally substituted alkyl group having 1 to 10 carbon atoms, an optionally substituted phenyl group, or an optionally substituted carbazolyl group;
and $R^{b14}$ represents a hydrogen atom, an alkyl group having 1 to 6 carbon atoms, or an optionally substituted phenyl group.

When $R^{b12}$ is an alkyl group having 1 to 10 carbon atoms, the alkyl group may be a straight chain or a branched chain. In this case, the number of carbon atoms in the alkyl group is preferably 1 to 8, more preferably 1 to 5.

When $R^{b12}$ is an optionally substituted phenyl group, the type of the substituent is not particularly limited as far as objects of the present invention are not inhibited. Examples of a suitable substituent that the phenyl group may have include an alkyl group, an alkoxy group, an cycloalkyl group, an cycloalkoxy group, a saturated aliphatic acyl group, an alkoxycarbonyl group, a saturated aliphatic acyloxy group, an optionally substituted phenyl group, an optionally substituted phenoxy group, an optionally substituted benzoyl group, an optionally substituted phenoxycarbonyl group, an optionally substituted benzoyloxy group, an optionally substituted phenylalkyl group, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group, an optionally substituted heterocyclyl group, an amino group, an amino group substituted with one or two organic groups, a morpholin-1-yl group, a piperazin-1-yl group, a halogen, a nitro group, a cyano group, and the like. When $R^{b12}$ is an optionally substituted phenyl group and the phenyl group has multiple substituents, the multiple substituents may be the same or different from each other.

When a substituent of the phenyl group is an alkyl group, the number of carbon atoms of the alkyl group is preferably 1 to 20, more preferably 1 to 10, further preferably 1 to 6, particularly preferably 1 to 3, most preferably 1. The alkyl group may be a straight chain or a branched chain. When a substituent of the phenyl group is an alkyl group, specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group, and the like. The alkyl group may have an ether bond (—O—) in the carbon chain. In this case, examples of a substituent of the phenyl group include an alkoxyalkyl group and an alkoxyalkoxyalkyl group. When a substituent of the phenyl group is an alkoxyalkyl group, a group represented by —$R^{b15}$—O—$R^{b16}$ is preferable. $R^{b15}$ represents a straight chain or branched chain alkylene group having 1 to 10 carbon atoms. $R^{b16}$ represents a straight chain or branched chain alkyl group having 1 to 10 carbon atoms. The number of carbon atoms of $R^{b15}$ is preferably 1 to 8, more preferably 1 to 5, particularly preferably 1 to 3. The number of carbon atoms of $R^{b16}$ is preferably 1 to 8, more preferably 1 to 5, particularly preferably 1 to 3, most preferably 1. Examples of the alkyl group having an ether bond in the carbon chain include a methoxyethyl group, an ethoxyethyl group, a methoxyethoxyethyl group, an ethoxyethoxyethyl group, a propyloxyethoxyethyl group, a methoxypropyl group, and the like.

When a substituent of the phenyl group is an alkoxy group, the number of carbon atoms of the alkoxy group is preferably 1 to 20, more preferably 1 to 6. The alkoxy group may be a straight chain or a branched chain. When a substituent of the phenyl group is an alkoxy group, specific examples include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, an isodecyloxy group, and the like. The alkoxy group may include an ether bond (—O—) in the carbon chain. Examples of the alkoxy group having an ether bond in the carbon chain include a methoxyethoxy group, an ethoxyethoxy group, a 2-methoxy-1-methylethoxy group, a methoxyethoxyethoxy group, an ethoxyethoxyethoxy group, a propyloxyethoxyethoxy group, a methoxypropyloxy group, and the like.

When a substituent of the phenyl group is a cycloalkyl group or a cycloalkoxy group, the number of carbon atoms of the cycloalkyl group or the cycloalkoxy group is preferably 3 to 10, more preferably 3 to 6. When a substituent of the phenyl group is a cycloalkyl group, specific examples include a cyclopropyl group, a cyclobutyl group, a cyclopentyl group, a cyclohexyl group, a cycloheptyl group, a cyclooctyl group, and the like. When a substituent of the phenyl group is a cycloalkoxy group, specific examples include a cyclopropyloxy group, a cyclobutyloxy group, a cyclopentyloxy group, a cyclohexyloxy group, a cycloheptyloxy group, a cyclooctyloxy group, and the like.

When a substituent of the phenyl group is a saturated aliphatic acyl group or a saturated aliphatic acyloxy group, the number of carbon atoms of the saturated aliphatic acyl group or the saturated aliphatic acyloxy group is preferably 2 to 20, more preferably 2 to 7. When a substituent of the phenyl group is a saturated aliphatic acyl group, specific examples include an acetyl group, a propanoyl group, an n-butanoyl group, a 2-methylpropanoyl group, an n-pentanoyl group, a 2,2-dimethylpropanoyl group, an n-hexanoyl group, an n-heptanoyl group, an n-octanoyl group, an n-nonanoyl group, an n-decanoyl group, an n-undecanoyl group, an n-dodecanoyl group, an n-tridecanoyl group, an n-tetradecanoyl group, an n-pentadecanoyl group, an n-hexadecanoyl group, and the like. When a substituent of the phenyl group is a saturated aliphatic acyloxy group, specific examples include an acetyloxy group, a propanoyloxy group, an n-butanoyloxy group, a 2-methylpropanoyloxy group, an n-pentanoyloxy group, a 2,2-dimethylpropanoyloxy group, an n-hexanoyloxy group, an n-heptanoyloxy group, an n-octanoyloxy group, an n-nonanoyloxy group, an n-decanoyloxy group, an n-undecanoyloxy group, an n-dodecanoyloxy group, an n-tridecanoyloxy group, an n-tetradecanoyloxy group, an n-pentadecanoyloxy group, an n-hexadecanoyloxy group, and the like.

When a substituent of the phenyl group is an alkoxycarbonyl group, the number of carbon atoms of the alkoxycarbonyl group is preferably 2 to 20, more preferably 2 to 7. When a substituent of the phenyl group is an alkoxycarbonyl group, specific examples include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an isopentyloxycarbonyl group, a sec-pentyloxycarbonyl group, a tert-pentyloxycarbonyl group, an n-hexyloxycarbonyl group, an n-heptyloxycarbonyl group, an n-octyloxycarbonyl group, an isooctyloxycarbonyl group, a sec-octyloxycarbonyl group, a tert-octyloxycarbonyl group, an n-nonyloxycarbonyl group, an isononyloxycarbonyl group, an n-decyloxycarbonyl group, an isodecyloxycarbonyl group, and the like.

When a substituent of the phenyl group is a phenylalkyl group, the number of carbon atoms of the phenylalkyl group is preferably 7 to 20, more preferably 7 to 10. When a substituent of the phenyl group is a naphthylalkyl group, the number of carbon atoms of the naphthylalkyl group is preferably 11 to 20, more preferably 11 to 14. When a substituent of the phenyl group is a phenylalkyl group, specific examples include a benzyl group, a 2-phenylethyl group, a 3-phenylpropyl group, and a 4-phenylbutyl group. When a substituent of the phenyl group is a naphthylalkyl group, specific examples include an α-naphthylmethyl group, a β-naphthylmethyl group, a 2-(α-naphthyl)ethyl group, and a 2-(β-naphthyl)ethyl group. When a substituent of the phenyl group is a phenylalkyl group or a naphthylalkyl group, the substituent may further have a substituent on a phenyl group or a naphthyl group.

When a substituent of the phenyl group is a heterocyclyl group, the heterocyclyl group is a 5- or 6-membered single ring containing one or more N, S, and O, or a heterocyclyl group in which single rings are condensed with each other, or a single ring is condensed with a benzene ring. When the heterocyclyl group is a condensed ring, the number of rings is 3 or less. Examples of the heterocycle constituting the heterocyclyl group include furan, thiophene, pyrrole, oxazole, isoxazole, triazole, thiadiazole, isothiazole, imidazole, pyrazole, triazole, pyridine, pyrazine, pyrimidine, pyridazine, benzofuran, benzothiophene, indole, isoindole, indolizine, benzoimidazole, benzotriazole, benzoxazole, benzothiazole, carbazole, purine, quinoline, isoquinoline, quinazoline, phthalazine, cinnoline, quinoxaline, and the like. When a substituent of the phenyl group is a heterocyclyl group, the heterocyclyl group may further have a substituent.

When a substituent of the phenyl group is an amino group substituted with one or two organic groups, suitable examples of the organic group include an alkyl group having 1 to 20 carbon atoms, a cycloalkyl group having 3 to 10 carbon atoms, a saturated aliphatic acyl group having 2 to 20 carbon atoms, a saturated aliphatic acyloxy group having 2 to 20 carbon atoms, an optionally substituted phenyl group, an optionally substituted benzoyl group, an optionally substituted phenylalkyl group having 7 to 20 carbon atoms, an optionally substituted naphthyl group, an optionally substituted naphthoyl group, an optionally substituted naphthylalkyl group having 11 to 20 carbon atoms, a heterocyclyl group, and the like. Specific examples of suitable organic groups are the same as the examples of the substituent of the phenyl group described above. Specific examples of the amino group substituted with one or two organic groups include a methylamino group, an ethylamino group, a diethylamino group, an n-propylamino group, a di-n-propylamino group, an isopropylamino group, an n-butylamino group, a di-n-butylamino group, an n-pentylamino group, an n-hexylamino group, an n-heptylamino group, an n-octylamino group, an n-nonylamino group, an n-decylamino group, a phenylamino group, a naphthylamino group, an acetylamino group, an propanoylamino group, an n-butanoylamino group, an n-pentanoylamino group, an n-hexanoylamino group, an n-heptanoylamino group, an n-octanoylamino group, an n-decanoylamino group, a benzoylamino group, an α-naphthoylamino group, a β-naphthoylamino group, an N-acetyl-N-acetyloxyamino group, and the like.

When an phenyl group, an naphthyl group, and a heterocyclyl group included in a substituent of the phenyl group further have a substituent, examples of the substituent include an alkyl group having 1 to 6 carbon atoms, an alkoxy group having 1 to 6 carbon atoms, a saturated aliphatic acyl group having 2 to 7 carbon atoms, an alkoxycarbonyl group having 2 to 7 carbon atoms, a saturated aliphatic acyloxy group having 2 to 7 carbon atoms, a monoalkylamino group which has an alkyl group having 1 to 6 carbon atoms, a dialkylamino group which has an alkyl group having 1 to 6 carbon atoms, a morpholin-1-yl group, an piperazin-1-yl group, halogen, a nitro group, a cyano group, and the like. When a phenyl group, a naphthyl group, and a heterocyclyl group included in a substituent of the phenyl group further have a substituent, the number of substituents is not particularly limited as long as the object of the present invention is not inhibited, and is preferably 1 to 4. When a phenyl group, a naphthyl group, and a heterocyclyl group included in a substituent of the phenyl group have multiple substituents, the multiple substituents may be the same as or different each other.

Substituents for the case in which $R^{b12}$ is an optionally substituted phenyl group are described above. Among those substituents, an alkyl group or an alkoxyalkyl group is preferable.

When $R^{b12}$ is an optionally substituted phenyl group, neither the number of substituents nor the position to which a substituent is bonded is particularly limited as far as objects of the present invention are not inhibited. When $R^{b12}$ is an optionally substituted phenyl group, the optionally substituted phenyl group is preferably an optionally substituted o-tolyl group for excellent efficiency of base generation.

When $R^{b12}$ is an optionally substituted carbazolyl group, the type of the substituent is not particularly limited as far as objects of the present invention are not inhibited. Examples of a suitable substituent that the carbazolyl group may have on a carbon atom include an alkyl group having 1 to 20 carbon atoms, an alkoxy group having 1 to 20 carbon atoms, a cycloalkyl group having 3 to 10 carbon atoms, a cycloalkoxy group having 3 to 10 carbon atoms, a saturated aliphatic acyl group having 2 to 20 carbon atoms, an alkoxycarbonyl group having 2 to 20 carbon atoms, a saturated aliphatic acyloxy group having 2 to 20 carbon atoms, an optionally substituted phenyl group, an optionally substituted phenoxy group, an optionally substituted phenylthio group, an optionally substituted phenyl carbonyl group, an optionally substituted benzoyl group, an optionally substituted phenoxycarbonyl group, an optionally substituted benzoyloxy group, an optionally substituted phenylalkyl group having 7 to 20 carbon atoms, an optionally substituted naphthyl group, an optionally substituted naphthoxy group, an optionally substituted naphthylcarbonyl group, an optionally substituted naphthoyl group, an optionally substituted naphthoxycarbonyl group, an optionally substituted naphthoyloxy group, an optionally substituted naphthylalkyl group having 11 to 20 carbon atoms, an optionally substituted heterocyclyl group, an optionally substituted heterocyclylcarbonyl group, an amino group, an amino group substituted with one or two organic groups, a morpholin-1-yl group, a piperazin-1-yl group, a halogen, a nitro group, and a cyano group.

When $R^{b12}$ is an optionally substituted carbazolyl group, examples of a suitable substituent that the carbazolyl group may have on a nitrogen atom include an alkyl group having 1 to 20 carbon atoms, a cycloalkyl group having 3 to 10 carbon atoms, a saturated aliphatic acyl group having 2 to 20 carbon atoms, an alkoxycarbonyl group having 2 to 20 carbon atoms, an optionally substituted phenyl group, an optionally substituted benzoyl group, an optionally substituted phenoxycarbonyl group, an optionally substituted phenylalkyl group having 7 to 20 carbon atoms, an optionally substituted naphthyl group, an optionally substituted naphthoyl group, an optionally substituted naphthoxycarbonyl group, an optionally substituted naphthylalkyl group having 11 to 20 carbon atoms, an optionally substituted heterocyclyl group, and an optionally substituted heterocyclylcarbonyl group. Among these substituents, an alkyl group having 1 to 20 carbon atoms is preferable, an alkyl group having 1 to 6 carbon atoms is more preferable, and an ethyl group is particularly preferable.

For an alkyl group, an alkoxy group, a cycloalkyl group, a cycloalkoxy group, a saturated aliphatic acyl group, an alkoxycarbonyl group, a saturated aliphatic acyloxy group, an optionally substituted phenylalkyl group, an optionally substituted naphthylalkyl group, an optionally substituted heterocyclyl group, and an amino group substituted with one or two organic groups, specific examples of a substituent that the carbazolyl group may have are the same as the examples of a substituent of the phenyl group when $R^{b12}$ is an optionally substituted phenyl group.

For $R^{b12}$, when a phenyl group, a naphthyl group, and a heterocyclyl group in a substituent of the carbazolyl group further have a substituent, examples of the substituent include an alkyl group having 1 to 6 carbon atoms; an alkoxy group having 1 to 6 carbon atoms; a saturated aliphatic acyl group having 2 to 7 carbon atoms; an alkoxycarbonyl group having 2 to 7 carbon atoms; a saturated aliphatic acyloxy group having 2 to 7 carbon atoms; a phenyl group; a naphthyl group; a benzoyl group; a naphthoyl group; a benzoyl group substituted with a group selected from the group consisting of an alkyl group having 1 to 6 carbon atoms, a morpholin-1-yl group, a piperazin-1-yl group, and a phenyl group; a monoalkylamino group having an alkyl group having 1 to 6 carbon atoms; a dialkylamino group having an alkyl group having 1 to 6 carbon atoms; a morpholin-1-yl group; a piperazin-1-yl group; a halogen; a nitro group; and a cyano group. When a phenyl group, a naphthyl group, and a heterocyclyl group in a substituent of the carbazolyl group further have a substituent, the number of substituents is not limited as far as objects of the present invention are not inhibited, and is preferably 1 to 4. When the phenyl group, the naphthyl group, and the heterocyclyl group have a plurality of substituents, the plurality of substituents may be the same or different from each other.

$R^{b13}$ represents an optionally substituted alkyl group having 1 to 10 carbon atoms, an optionally substituted phenyl group, or an optionally substituted carbazolyl group.

When $R^{b13}$ is an optionally substituted alkyl group having 1 to 10 carbon atoms, the alkyl group may be a straight chain or a branched chain. In this case, the number of carbon atoms of the alkyl group is preferably 1 to 8, more preferably 1 to 5.

For $R^{b13}$, there is no particular limitation for substituents on the alkyl group, the phenyl group, or the carbazolyl group as long as the object of the present invention is not inhibited. Examples of suitable substituents which the alkyl group may have on the carbon atom include an alkoxy group having 1 to 20 carbon atoms, a cycloalkyl group having 3 to 10 carbon atoms, a cycloalkoxy group having 3 to 10 carbon atoms, a saturated aliphatic acyl group having 2 to 20 carbon atoms, an alkoxycarbonyl group having 2 to 20 carbon atoms, a saturated aliphatic acyloxy group having 2 to 20 carbon atoms, an optionally substituted phenyl group, an optionally substituted phenoxy group, an optionally substituted phenylthio group, an optionally substituted benzoyl group, an optionally substituted phenoxycarbonyl group, an optionally substituted benzoyloxy group, an optionally substituted phenylalkyl group having 7 to 20 carbon atoms, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group having 11 to 20 carbon atoms, an optionally substituted heterocyclyl group, an optionally substituted heterocyclylcarbonyl group, an amino group, an amino group substituted with one or two organic groups, a morpholine-1-yl group, a piperazine-1-yl group, halogen, a nitro group, a cyano group and the like. Examples of a suitable substituent that the phenyl group and the carbazolyl group may have on a carbon atom include the above examples of groups as a suitable substituent that the alkyl group may have on a carbon atom and an alkyl group having 1 to 20 carbon atoms.

For an alkyl group, an alkoxy group, a cycloalkyl group, a cycloalkoxy group, a saturated aliphatic acyl group, an alkoxycarbonyl group, a saturated aliphatic acyloxy group, an optionally substituted phenylalkyl group, an optionally substituted naphthylalkyl group, an optionally substituted heterocyclyl group and an amino group substituted with one or two organic groups, specific examples of optional substituents on the alkyl group, the phenyl group, or the carbazolyl group are the same as the examples of a substituent of the phenyl group when $R^{b12}$ is an optionally substituted phenyl group.

In a case where the phenyl group, the naphthyl group and the heterocyclyl group included in the substituent on the alkyl group, the phenyl group, or the carbazolyl group in $R^{b13}$ further have a substituent, examples of the substituent include an alkyl group having 1 to 6 carbon atoms; an alkoxy group having 1 to 6 carbon atoms; a saturated aliphatic acyl group having 2 to 7 carbon atoms; an alkoxycarbonyl group having 2 to 7 carbon atoms; a saturated aliphatic acyloxy group having 2 to 7 carbon atoms; a phenyl group; a naphthyl group; a benzoyl group; a naphthoyl group; a benzoyl group substituted with a group selected from the group consisting of an alkyl group having 1 to 6 carbon atoms, a morpholine-1-yl group, a piperazine-1-yl group and a phenyl group; a monoalkylamino group having an alkyl group having 1 to 6 carbon atoms; a dialkylamino group having an alkyl group having 1 to 6 carbon atoms; a morpholine-1-yl group; a piperazine-1-yl group; halogen; a nitro group; and a cyano group. In a case where the phenyl group, the naphthyl group and the heterocyclyl group included in the substituent on the alkyl group or the phenyl group further have a substituent, the number of substituents is not limited as far as objects of the present invention are not inhibited, and is preferably 1 to 4. In a case where the phenyl group, the naphthyl group and the heterocyclyl group have multiple substituents, the substituents may be different from or the same as each other.

From a viewpoint of efficiency of base generation of a compound represented by the formula (B4), as $R^{b13}$, a group represented by the following formula (B5):

[Chem. 22]

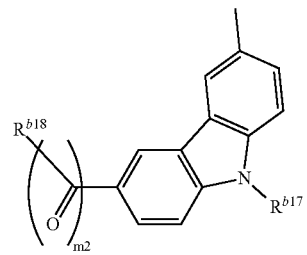

(B5)

and a group represented by the following formula (B6):

[Chem. 23]

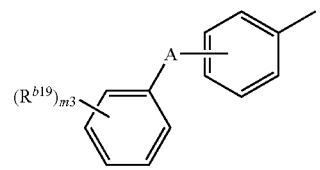

(B6)

are preferable.

In the formula (B5), $R^{b17}$ and $R^{b18}$ each represent a monovalent organic group and m2 is 0 or 1. In the formula (B6), $R^{b19}$ represents a group selected from the group consisting of a monovalent organic group, an amino group, a halogen, a nitro group, and a cyano group, A represents S or O, and m3 is an integer of 0 to 4.

$R^{b17}$ in the formula (B5) may be selected from various organic groups as far as objects of the present invention are not inhibited. Examples of suitable $R^{b17}$ include an alkyl group having 1 to 20 carbon atoms, a cycloalkyl group having 3 to 10 carbon atoms, a saturated aliphatic acyl group having 2 to 20 carbon atoms, an alkoxycarbonyl group having 2 to 20 carbon atoms, an optionally substituted phenyl group, an optionally substituted benzoyl group, an optionally substituted phenoxycarbonyl group, an optionally substituted phenylalkyl group having 7 to 20 carbon atoms, an optionally substituted naphthyl group, an optionally substituted naphthoyl group, an optionally substituted naphthoxycarbonyl group, an optionally substituted naphthylalkyl group having 11 to 20 carbon atoms, an optionally substituted heterocyclyl group, and an optionally substituted heterocyclylcarbonyl group.

Among the above groups as $R^{b17}$, an alkyl group having 1 to 20 carbon atoms is preferable, an alkyl group having 1 to 6 carbon atoms is more preferable, and an ethyl group is particularly preferable.

$R^{b18}$ in the formula (B5) is not particularly limited as far as objects of the present invention are not inhibited, and may be selected from various organic groups. Specific examples of a suitable group as $R^{b18}$ include an alkyl group having 1 to 20 carbon atoms, an optionally substituted phenyl group, an optionally substituted naphthyl group, and an optionally substituted heterocyclyl group. Among these groups, $R^{b18}$ is more preferably an optionally substituted phenyl group and an optionally substituted naphthyl group, particularly preferably a 2-methylphenyl group and a naphthyl group.

When a phenyl group, a naphthyl group, and a heterocyclyl group in $R^{b17}$ or $R^{b18}$ further have a substituent, examples of the substituent include an alkyl group having 1 to 6 carbon atoms, an alkoxy group having 1 to 6 carbon atoms, a saturated aliphatic acyl group having 2 to 7 carbon atoms, an alkoxycarbonyl group having 2 to 7 carbon atoms, a saturated aliphatic acyloxy group having 2 to 7 carbon atoms, a monoalkylamino group having an alkyl group having 1 to 6 carbon atoms, a dialkylamino group having an alkyl group having 1 to 6 carbon atoms, a morpholin-1-yl group, a piperazin-1-yl group, a halogen, a nitro group, and a cyano group. When a phenyl group, a naphthyl group, and a heterocyclyl group in $R^{b17}$ or $R^{b18}$ further have a substituent, the number of substituents is not limited as far as objects of the present invention are not inhibited, and is preferably 1 to 4. When a phenyl group, a naphthyl group, and a heterocyclyl group in $R^{b17}$ or $R^{b18}$ has a plurality of substituents, the plurality of substituents may be the same or different from each other.

When $R^{b19}$ in the formula (B6) is an organic group, $R^{b19}$ can be selected from various kinds of organic groups as far as objects of the present invention are not inhibited. Preferred examples when $R^{b19}$ is an organic group in the formula (B6) include alkyl groups having 1 to 6 carbon atoms; alkoxy groups having 1 to 6 carbon atoms; saturated aliphatic acyl groups having 2 to 7 carbon atoms; alkoxycarbonyl groups having 2 to 7 carbon atoms; saturated aliphatic acyloxy groups having 2 to 7 carbon atoms; a phenyl group; a naphthyl group; a benzoyl group; a naphthoyl group; benzoyl groups substituted with a group selected from the group consisting of an alkyl group having 1 to 6 carbon atoms, a morpholine-1-yl group, a piperazine-1-yl group and a phenyl group; monoalkylamino groups having an alkyl group having 1 to 6 carbon atoms; dialkylamino groups having alkyl groups having 1 to 6 carbon atoms; a morpholine-1-yl group; a piperazine-1-yl group; halogen; a nitro group; a cyano group; a 2-methylphenyl carbonyl group; a 4-(piperazin-1-yl)phenyl carbonyl group; and a 4-(phenyl)phenyl carbonyl group.

Among $R^{b19}$, a benzoyl group; a naphthoyl group; a benzoyl groups substituted with a group selected from the group consisting of an alkyl group having 1 to 6 carbon atoms, a morpholine-1-yl group, a piperazine-1-yl group, and a phenyl group; and a nitro group are preferred, and a benzoyl group; a naphthoyl group; a 2-methylphenyl carbonyl group; a 4-(piperazine-1-yl) phenyl carbonyl group; and a 4-(phenyl) phenyl carbonyl group are more preferred.

In the formula (B6), m3 is preferably an integer of 0 to 3, more preferably an integer of 0 to 2, and particularly preferably 0 or 1. When m3 is 1, the position at which $R^{b19}$ bonds is preferably the para-position to the bonding through which the phenyl group (to which $R^{b19}$ bonds) bonds to a sulfur atom.

$R^{b14}$ represents a hydrogen atom, an alkyl group having 1 to 6 carbon atoms, or an optionally substituted phenyl group. When an optionally substituted phenyl group is represented, the substituent that the phenyl group may have is the same as the substituent for the case in which $R^{b12}$ is an optionally substituted phenyl group. $R^{b14}$ is preferably a methyl group, an ethyl group, or a phenyl group, more preferably a methyl group or a phenyl group.

An oxime ester compound represented by the formula (B4) in which m1 is 0 may be synthesized by the following method, for example. First, a ketone compound represented by $R^{b13}$—CO—$R^{b12}$ is converted into an oxime by using hydroxylamine, and thus an oxime compound represented by $R^{b13}$—(C=N—OH)—$R^{b12}$ is obtained. Then, the resulting oxime compound is acylated by using an acid halide represented by $R^{b14}$—CO-Hal (Hal represents halogen) or an acid anhydride represented by $(R^{b14}CO)_2O$, and thus an oxime ester compound represented by the formula (B4) in which m1 is 0 is obtained.

An oxime ester compound represented by the formula (B4) in which m1 is 1 may be synthesized by the following method, for example. First, a ketone compound represented by $R^{b13}$—CO—$CH_2$—$R^{b12}$ is subjected to reaction with nitrous ester in the presence of hydrochloric acid, and thus an oxime compound represented by $R^{b13}$—CO—(C=N—OH)—$R^{b12}$ is obtained. Then, the resulting oxime compound is acylated by using an acid halide represented by $R^{b14}$—CO-Hal (Hal represents halogen) or an acid anhydride represented by $(R^{b14}CO)_2O$, and thus an oxime ester compound represented by the formula (B4) in which m1 is 1 is obtained.

Examples of a compound represented by the formula (B4) include a compound represented by the following formula (B7).

[Chem. 24]

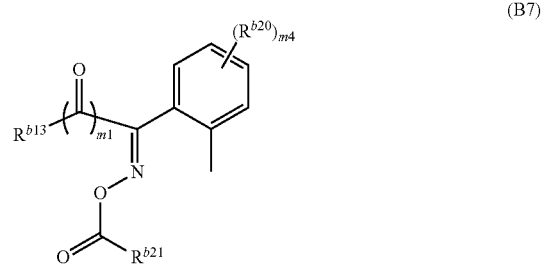

(B7)

In the formula (B7), m1 and $R^{b13}$ are as described above. $R^{b20}$ represents a group selected from the group consisting of a monovalent organic group, an amino group, a halogen, a nitro group, and a cyano group, m4 is an integer of 0 to 4, and $R^{b21}$ represents a hydrogen atom or an alkyl group having 1 to 6 carbon atoms.

In the formula (B7), $R^{b20}$ is not particularly limited as far as objects of the present invention are not inhibited, and when it is an organic group, it is appropriately selected from various organic groups. Suitable examples of $R^{b20}$ include an alkyl group, an alkoxy group, a cycloalkyl group, a cycloalkoxy group, a saturated aliphatic acyl group, an alkoxycarbonyl group, a saturated aliphatic acyloxy group, an optionally substituted phenyl group, an optionally substituted phenoxy group, an optionally substituted benzoyl group, an optionally substituted phenoxycarbonyl group, an optionally substituted benzoyloxy group, an optionally substituted phenylalkyl group, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group, an optionally substituted heterocyclyl group, an amino group, an amino group substituted with one or two organic groups, a morpholin-1-yl group, a piperazin-1-yl group, a halogen, a nitro group, and a cyano group. When m4 is an integer of 2 to 4, $R^{b20}$ may be the same or different from each other. The number of carbon atoms of the substituent does not include the number of carbon atoms of any further substituents of the substituent.

When $R^{b20}$ is an alkyl group, the number of carbon atoms is preferably 1 to 20, and more preferably 1 to 6. When $R^{b20}$ is an alkyl group, the alkyl group may be a straight chain or branched chain alkyl group. When $R^{b20}$ is an alkyl group, specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group, and the like. When $R^{b20}$ is an alkyl group, the alkyl group may contain an ether bond (—O—) in the carbon chain. Examples of the alkyl group having an ether bond in the carbon chain include a methoxyethyl group, an ethoxyethyl group, a methoxyethoxyethyl group, an ethoxyethoxyethyl group, a propyloxyethoxyethyl group, a methoxypropyl group, and the like.

When $R^{b20}$ is an alkoxy group, the number of carbon atoms is preferably 1 to 20, and more preferably 1 to 6. When $R^{b20}$ is an alkoxy group, the alkoxy group may be a straight chain or branched chain group. When $R^{b20}$ is an alkoxy group, specific examples thereof include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, and an isodecyloxy group. When $R^{b20}$ is an alkoxy group, the alkoxy group may contain an ether bond (—O—) in the carbon chain. Examples of the alkoxy group having an ether bond in the carbon chain include a methoxyethoxy group, an ethoxyethoxy group, a methoxyethoxyethoxy group, an ethoxyethoxyethoxy group, a propyloxyethoxyethoxy group, and a methoxypropyloxy group.

When $R^{b20}$ is a cycloalkyl group or a cycloalkoxy group, the number of carbon atoms is preferably 3 to 10, and more preferably 3 to 6. When $R^{b20}$ is a cycloalkyl group, specific examples thereof include a cyclopropyl group, a cyclobutyl group, a cyclopentyl group, a cyclohexyl group, a cycloheptyl group, and a cyclooctyl group. When $R^{b20}$ is a cycloalkoxy group, specific examples thereof include a cyclopropyloxy group, a cyclobutyloxy group, a cyclopentyloxy group, a cyclohexyloxy group, a cycloheptyloxy group, and a cyclooctyloxy group.

When $R^{b20}$ is a saturated aliphatic acyl group or a saturated aliphatic acyloxy group, the number of carbon atoms is preferably 2 to 20, and more preferably 2 to 7. When $R^{b20}$ is a saturated aliphatic acyl group, specific examples thereof include an acetyl group, a propanoyl group, an n-butanoyl group, a 2-methylpropanoyl group, an n-pentanoyl group, a 2,2-dimethylpropanoyl group, an n-hexanoyl group, an n-heptanoyl group, an n-octanoyl group, an n-nonanoyl group, an n-decanoyl group, an n-undecanoyl group, an n-dodecanoyl group, an n-tridecanoyl group, an n-tetradecanoyl group, an n-pentadecanoyl group, and an n-hexadecanoyl group. When $R^{b20}$ is a saturated aliphatic acyloxy group, specific examples thereof include an acetyloxy group, a propanoyloxy group, an n-butanoyloxy group, a 2-methylpropanoyloxy group, an n-pentanoyloxy group, a 2,2-dimethylpropanoyloxy group, an n-hexanoyloxy group, an n-heptanoyloxy group, an n-octanoyloxy group, an n-nonanoyloxy group, an n-decanoyloxy group, an n-undecanoyloxy group, an n-dodecanoyloxy group, an n-tridecanoyloxy group, an n-tetradecanoyloxy group, an n-pentadecanoyloxy group, and an n-hexadecanoyloxy group.

When $R^{b20}$ is an alkoxycarbonyl group, the number of carbon atoms is preferably 2 to 20, and preferably 2 to 7. When $R^{b20}$ is an alkoxycarbonyl group, specific examples thereof include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an isopentyloxycarbonyl group, a sec-pentyloxycarbonyl group, a tert-pentyloxycarbonyl group, an n-hexyloxycarbonyl group, an n-heptyloxycarbonyl group, an n-octyloxycarbonyl group, an isooctyloxycarbonyl group, a sec-octyloxycarbonyl group, a tert-octyloxycarbonyl group, an n-nonyloxycarbonyl group, an isononyloxycarbonyl group, an n-decyloxycarbonyl group, and an isodecyloxycarbonyl group.

When $R^{b20}$ is a phenylalkyl group, the number of carbon atoms is preferably 7 to 20, and more preferably 7 to 10. When $R^{b20}$ is a naphthylalkyl group, the number of carbon atoms is preferably 11 to 20, and more preferably 11 to 14. When $R^{b20}$ is a phenylalkyl group, specific examples thereof include a benzyl group, a 2-phenylethyl group, a 3-phenylpropyl group, and a 4-phenylbutyl group. When $R^{b20}$ is a naphthylalkyl group, specific examples thereof include an α-naphthylmethyl group, a β-naphthylmethyl group, a 2-(α-naphthyl)ethyl group, and a 2-(β-naphthyl)ethyl group. When $R^{b20}$ is a phenylalkyl group or a naphthylalkyl group, $R^{b20}$ may further have a substituent on a phenyl group or a naphthyl group.

When $R^{b20}$ is a heterocyclyl group, the heterocyclyl group is a 5- or 6-membered single ring containing one or more N, S, and O, or a heterocyclyl group in which single rings are condensed with each other, or a single ring is condensed with a benzene ring. When the heterocyclyl group is a condensed ring, the number of rings is 3 or less. Examples of the heterocycle constituting the heterocyclyl group include furan, thiophene, pyrrole, oxazole, isoxazole, triazole, thiadiazole, isothiazole, imidazole, pyrazole, triazole, pyridine, pyrazine, pyrimidine, pyridazine, benzofuran, benzothiophene, indole, isoindole, indolizine, benzoimidazole, benzotriazole, benzoxazole, benzothiazole, carbazole, purine, quinoline, isoquinoline, quinazoline, phthalazine, cinnoline, quinoxaline, and the like. When $R^{b20}$ is a heterocyclyl group, the heterocyclyl group may have a further substituent.

When $R^{b20}$ is an amino group substituted with one or two organic groups, suitable examples of the organic group include an alkyl group having 1 to 20 carbon atoms, a cycloalkyl group having 3 to 10 carbon atoms, a saturated aliphatic acyl group having 2 to 20 carbon atoms, an optionally substituted phenyl group, an optionally substituted benzoyl group, an optionally substituted phenylalkyl group having 7 to 20 carbon atoms, an optionally substituted naphthyl group, an optionally substituted naphthoyl group, an optionally substituted naphthylalkyl group having 11 to 20 carbon atoms, a heterocyclyl group, and the like. Specific examples of suitable organic group are the same as those in $R^{b20}$. Specific examples of the amino group substituted with one or two organic groups include a methylamino group, an ethylamino group, a diethylamino group, an n-propylamino group, a di-n-propylamino group, an isopropylamino group, an n-butylamino group, a di-n-butylamino group, an n-pentylamino group, an n-hexylamino group, an n-heptylamino group, an n-octylamino group, an n-nonylamino group, an n-decylamino group, a phenylamino group, a naphthylamino group, an acetylamino group, an propanoylamino group, an n-butanoylamino group, an n-pentanoylamino group, an n-hexanoylamino group, an n-heptanoylamino group, an n-octanoylamino group, an n-decanoylamino group, a benzoylamino group, an α-naphthoylamino group, a β-naphthoylamino group, and the like.

When an phenyl group, an naphthyl group, and a heterocyclyl group included in $R^{b20}$ further have a substituent, examples of the substituent include an alkyl group having 1 to 6 carbon atoms, an alkoxy group having 1 to 6 carbon atoms, a saturated aliphatic acyl group having 2 to 7 carbon atoms, an alkoxycarbonyl group having 2 to 7 carbon atoms, a saturated aliphatic acyloxy group having 2 to 7 carbon atoms, a monoalkylamino group which has an alkyl group having 1 to 6 carbon atoms, a dialkylamino group which has an alkyl group having 1 to 6 carbon atoms, a morpholin-1-yl group, an piperazin-1-yl group, halogen, a nitro group, a cyano group, and the like. When a phenyl group, a naphthyl group, and a heterocyclyl group included in $R^{b20}$ further have a substituent, the number of substituents is not particularly limited as long as the object of the present invention is not inhibited, and is preferably 1 to 4. When a phenyl group, a naphthyl group, and a heterocyclyl group included in $R^{b20}$ have multiple substituents, the multiple substituents may be the same as or different each other.

Among $R^{b20}$s, a group selected from the group consisting of an alkyl group having 1 to 6 carbon atoms, an alkoxy group having 1 to 6 carbon atoms, and a saturated aliphatic acyl group having 2 to 7 carbon atoms is preferable, an alkyl having 1 to 6 carbon atoms is more preferable, and a methyl group is particularly preferable, since these are chemically stable and facilitate the synthesis of an oxime ester compound due to little steric hindrance.

When the position of a bond of a phenyl group and a main skeleton of an oxime ester compound is regarded as the 1-position and the position of a methyl group is regarded as the 2-position with respect to the phenyl group to which $R^{b20}$ is bonded, the position at which $R^{b20}$ is bonded to a phenyl group is preferably the 4-position or the 5-position, more preferably the 5-position. m4 is preferably an integer of 0 to 3, more preferably an integer of 0 to 2, particularly preferably 0 or 1.

$R^{b21}$ in the formula (B7) is a hydrogen atom, or an alkyl group having 1 to 6 carbon atoms. $R^{b21}$ is preferably a methyl group or an ethyl group, and more preferably a methyl group.

Specific examples of a particularly suitable compound as an oxime ester compound represented by the formula (B4) are as follows.

[Chem. 25]

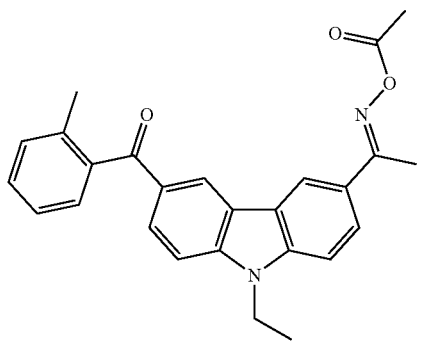

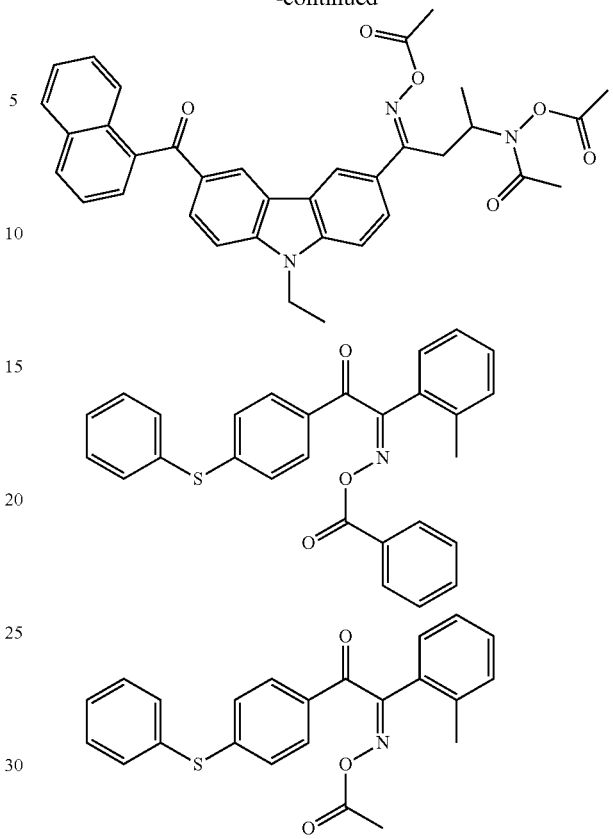

A compound represented by the following formula (B8) is also suitably used as an oxime ester compound.

[Chem. 26]

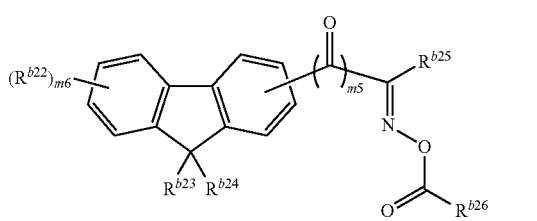

(B8)

($R^{b22}$ is a hydrogen atom, a nitro group, or a monovalent organic group, $R^{b23}$ and $R^{b24}$ each represent an optionally substituted chain alkyl group, an optionally substituted cyclic organic group, or a hydrogen atom, $R^{b23}$ and $R^{b24}$ may be bonded to one another to form a ring, $R^{b25}$ is a monovalent organic group, $R^{b26}$ is a hydrogen atom, an optionally substituted alkyl group having 1 to 11 carbon atoms, or an optionally substituted aryl group, m6 is an integer of 0 to 4, and m5 is 0 or 1.)

In the formula (B8), $R^{b22}$ is a hydrogen atom, a nitro group, or a monovalent organic group. $R^{b22}$ is bonded to a 6-membered aromatic ring which is different from the 6-membered aromatic ring bonded to a group represented as —(CO)$_{m5}$— on a fluorene ring in the formula (B8). In the formula (B8), the bond position of $R^{b22}$ to a fluorene ring is not particularly limited. When a compound represented by the formula (B8) has one or more $R^{b22}$s, one of the one or more $R^{b22}$s is preferably bonded at the 2-position in the fluorene ring since synthesis of the compound represented by the formula (B8) becomes easy. When multiple $R^{b22}$s exist, the multiple $R^{b22}$s may be the same or different.

When $R^{b22}$ is an organic group, $R^{b22}$ is not particularly limited as long as the object of the present invention is not inhibited, and is appropriately selected from various organic groups. When $R^{b22}$ is an organic group, suitable examples include an alkyl group, an alkoxy group, a cycloalkyl group, a cycloalkoxy group, a saturated aliphatic acyl group, an alkoxycarbonyl group, a saturated aliphatic acyloxy group, an optionally substituted phenyl group, an optionally substituted phenoxy group, an optionally substituted benzoyl group, an optionally substituted phenoxycarbonyl group, an optionally substituted benzoyloxy group, an optionally substituted phenylalkyl group, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group, an optionally substituted heterocyclyl group, an optionally substituted heterocyclylcarbonyl group, an amino group substituted with one or two organic groups, a morpholin-1-yl group, and a piperazin-1-yl group.

When $R^{b22}$ is an alkyl group, the number of carbon atoms of the alkyl group is preferably 1 to 20, and more preferably 1 to 6. When $R^{b22}$ is an alkyl group, the alkyl group may be a straight chain or branched chain alkyl group. When $R^{b22}$ is an alkyl group, specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group, and the like. When $R^{b22}$ is an alkyl group, the alkyl group may contain an ether bond (—O—) in the carbon chain. Examples of the alkyl group having an ether bond in the carbon chain include a methoxyethyl group, an ethoxyethyl group, a methoxyethoxyethyl group, an ethoxyethoxyethyl group, a propyloxyethoxyethyl group, a methoxypropyl group, and the like.

When $R^{b22}$ is an alkoxy group, the number of carbon atoms of the alkoxy group is preferably 1 to 20, and more preferably 1 to 6. When $R^{b22}$ is an alkoxy group, the alkoxy group may be a straight chain or branched chain group. When $R^{b22}$ is an alkoxy group, specific examples thereof include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, and an isodecyloxy group. When $R^{b22}$ is an alkoxy group, the alkoxy group may contain an ether bond (—O—) in the carbon chain. Examples of the alkoxy group having an ether bond in the carbon chain include a methoxyethoxy group, an ethoxyethoxy group, a methoxyethoxyethoxy group, an ethoxyethoxyethoxy group, a propyloxyethoxyethoxy group, and a methoxypropyloxy group.

When $R^{b22}$ is a cycloalkyl group or a cycloalkoxy group, the number of carbon atoms of the cycloalkyl group or cycloalkoxy group is preferably 3 to 10, and more preferably 3 to 6. When $R^{b22}$ is a cycloalkyl group, specific examples thereof include a cyclopropyl group, a cyclobutyl group, a cyclopentyl group, a cyclohexyl group, a cycloheptyl group, and a cyclooctyl group. When $R^{b22}$ is a cycloalkoxy group, specific examples thereof include a cyclopropyloxy group, a cyclobutyloxy group, a cyclopentyloxy group, a cyclohexyloxy group, a cycloheptyloxy group, and a cyclooctyloxy group.

When $R^{b22}$ is a saturated aliphatic acyl group or a saturated aliphatic acyloxy group, the number of carbon atoms of the saturated aliphatic acyl group or saturated aliphatic acyloxy group is preferably 2 to 21, and more preferably 2 to 7. When $R^{b22}$ is a saturated aliphatic acyl group, specific examples thereof include an acetyl group, a propanoyl group, an n-butanoyl group, a 2-methylpropanoyl group, an n-pentanoyl group, a 2,2-dimethylpropanoyl group, an n-hexanoyl group, an n-heptanoyl group, an n-octanoyl group, an n-nonanoyl group, an n-decanoyl group, an n-undecanoyl group, an n-dodecanoyl group, an n-tridecanoyl group, an n-tetradecanoyl group, an n-pentadecanoyl group, and an n-hexadecanoyl group. When $R^{b22}$ is a saturated aliphatic acyloxy group, specific examples thereof include an acetyloxy group, a propanoyloxy group, an n-butanoyloxy group, a 2-methylpropanoyloxy group, an n-pentanoyloxy group, a 2,2-dimethylpropanoyloxy group, an n-hexanoyloxy group, an n-heptanoyloxy group, an n-octanoyloxy group, an n-nonanoyloxy group, an n-decanoyloxy group, an n-undecanoyloxy group, an n-dodecanoyloxy group, an n-tridecanoyloxy group, an n-tetradecanoyloxy group, an n-pentadecanoyloxy group, and an n-hexadecanoyloxy group.

When $R^{b22}$ is an alkoxycarbonyl group, the number of carbon atoms of the alkoxycarbonyl group is preferably 2 to 20, and more preferably 2 to 7. When $R^{b22}$ is an alkoxycarbonyl group, specific examples thereof include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an isopentyloxycarbonyl group, a sec-pentyloxycarbonyl group, a tert-pentyloxycarbonyl group, an n-hexyloxycarbonyl group, an n-heptyloxycarbonyl group, an n-octyloxycarbonyl group, an isooctyloxycarbonyl group, a sec-octyloxycarbonyl group, a tert-octyloxycarbonyl group, an n-nonyloxycarbonyl group, an isononyloxycarbonyl group, an n-decyloxycarbonyl group, and an isodecyloxycarbonyl group.

When $R^{b22}$ is a phenylalkyl group, the number of carbon atoms of the phenylalkyl group is preferably 7 to 20, and more preferably 7 to 10. When $R^{b22}$ is a naphthylalkyl group, the number of carbon atoms of the naphthylalkyl group is preferably 11 to 20, and more preferably 11 to 14. When $R^{b22}$ is a phenylalkyl group, specific examples thereof include a benzyl group, a 2-phenylethyl group, a 3-phenylpropyl group, and a 4-phenylbutyl group. When $R^{b22}$ is a naphthylalkyl group, specific examples thereof include an α-naphthylmethyl group, a β-naphthylmethyl group, a 2-(α-naphthyl)ethyl group, and a 2-(β-naphthyl)ethyl group. When $R^{b22}$ is a phenylalkyl group or a naphthylalkyl group, $R^{b22}$ may further have a substituent on a phenyl group or a naphthyl group.

When $R^{b22}$ is a heterocyclyl group, the heterocyclyl group is a 5- or 6-membered single ring containing one or more N, S, and O, or a heterocyclyl group in which single rings are condensed with each other, or a single ring is condensed with a benzene ring. When the heterocyclyl group is a condensed ring, the number of rings is 3 or less. The heterocyclyl group may be an aromatic group (heteroaryl group) or a non-aromatic group. Examples of the heterocycle constituting the heterocyclyl group include furan, thiophene, pyrrole, oxazole, isoxazole, triazole, thiadiazole, isothiazole, imidazole, pyrazole, triazole, pyridine, pyrazine, pyrimidine, pyridazine, benzofuran, benzothiophene, indole, isoindole, indolizine, benzoimidazole, benzotriazole, benzoxazole, benzothiazole, carbazole, purine, quinoline, isoquinoline, quinazoline, phthalazine, cinnoline, quinoxaline, piperidine, piperazine, morpholine, piperidine, tetrahydropyran, and tetrahydrofuran. When $R^{b22}$ is a heterocyclyl group, the heterocyclyl group may further have a substituent.

When $R^{b22}$ is a heterocyclylcarbonyl group, a heterocyclyl group included in the heterocyclylcarbonyl group is the same as that in the case where $R^{b22}$ is a heterocyclyl group.

When $R^{b22}$ is an amino group substituted with one or two organic groups, suitable examples of the organic groups include an alkyl group having 1 to 20 carbon atoms, a cycloalkyl group having 3 to 10 carbon atoms, a saturated aliphatic acyl group having 2 to 21 carbon atoms, an optionally substituted phenyl group, an optionally substituted benzoyl group, an optionally substituted phenylalkyl group having 7 to 20 carbon atoms, an optionally substituted naphthyl group, an optionally substituted naphthoyl group, an optionally substituted naphthylalkyl group having 11 to 20 carbon atoms, and a heterocyclyl group. The specific examples of these suitable organic groups are the same as those of $R^{b22}$. Specific examples of the amino group substituted with one or two organic groups include a methylamino group, an ethylamino group, a diethylamino group, an n-propylamino group, a di-n-propylamino group, an isopropylamino group, an n-butylamino group, a di-n-butylamino group, an n-pentylamino group, an n-hexylamino group, an n-heptylamino group, an n-octylamino group, an n-nonylamino group, an n-decylamino group, a phenylamino group, a naphthylamino group, an acetylamino group, a propanoylamino group, an n-butanoylamino group, an n-pentanoylamino group, an n-hexanoylamino group, an n-heptanoylamino group, an n-octanoylamino group, an n-decanoylamino group, an benzoylamino group, an α-naphthoylamino group, and a β-naphthoylamino group.

When the phenyl group, the naphthyl group, and the heterocyclyl group included in $R^{b22}$ further have a substituent, examples thereof include an alkyl group having 1 to 6 carbon atoms, an alkoxy group having 1 to 6 carbon atoms, a saturated aliphatic acyl group having 2 to 7 carbon atoms, an alkoxycarbonyl group having 2 to 7 carbon atoms, a saturated aliphatic acyloxy group having 2 to 7 carbon atoms, a monoalkylamino group having an alkyl group which has 1 to 6 carbon atoms, a dialkylamino group having an alkyl group which has 1 to 6 carbon atoms, a morpholin-1-yl group, a piperazin-1-yl group, halogen, a nitro group, and a cyano group. When a phenyl group, a naphthyl group, and a heterocyclyl group included in $R^{b22}$ further have substituents, the number of substituents is not particularly limited as long as the object of the present invention is not inhibited, and is preferably 1 to 4. When a phenyl group, a naphthyl group, and a heterocyclyl group included in $R^{b22}$ have multiple substituents, the multiple substituents may be the same or different.

Among the above-described groups, $R^{b22}$ is preferably a nitro group or a group represented as $R^{b27}$—CO— since the sensitivity tends to be improved. $R^{b27}$ is not particularly limited as long as the object of the present invention is not inhibited, and can be selected from various organic groups. Examples of the group suitable as $R^{b27}$ include an alkyl group having 1 to 20 carbon atoms, an optionally substituted phenyl group, an optionally substituted naphthyl group, and an optionally substituted heterocyclyl group. Among these groups, $R^{b27}$ is particularly preferably a 2-methylphenyl group, a thiophen-2-yl group, and an α-naphthyl group. $R^{b22}$ is also preferably a hydrogen atom. When $R^{b22}$ is a hydrogen atom, $R^{b25}$ is preferably a group represented by the following formula (B10).

In the formula (B8), $R^{b23}$ and $R^{b24}$ each represent an optionally substituted chain alkyl group, an optionally substituted cyclic organic group, or a hydrogen atom. $R^{b23}$ and $R^{b24}$ may be bonded to one another to form a ring. Among these groups, preferably, $R^{b23}$ and $R^{b24}$ are optionally substituted chain alkyl groups. When $R^{b23}$ and $R^{b24}$ are optionally substituted chain alkyl groups, a chain alkyl group may be a straight chain alkyl group or a branched chain alkyl group.

When $R^{b23}$ and $R^{b24}$ are chain alkyl groups having no substituents, the number of carbon atoms of the chain alkyl group is preferably 1 to 20, more preferably 1 to 10, and particularly preferably 1 to 6. When $R^{b23}$ and $R^{b24}$ are chain alkyl groups, specific examples thereof include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, and an isodecyl group. When $R^{b23}$ and $R^{b24}$ are alkyl groups, the alkyl group may have an ether bond (—O—) in a carbon chain. Examples of the alkyl group having an ether bond in a carbon chain include a methoxyethyl group, an ethoxyethyl group, a methoxyethoxyethyl group, an ethoxyethoxyethyl group, a propyloxyethoxyethyl group, and a methoxypropyl group.

When $R^{b23}$ and $R^{b24}$ are chain alkyl groups having a substituent, the number of carbon atoms of the chain alkyl group is preferably 1 to 20, more preferably 1 to 10, and particularly preferably 1 to 6. In this case, the number of carbon atoms of the substituent is not included in the number of carbon atoms of the chain alkyl group. The chain alkyl group having a substituent is preferably a straight chain group. The substituent, with which the alkyl group is optionally substituted, is not particularly limited as long as the object of the present invention is not inhibited. Suitable examples of the substituent include a cyano group, a halogen atom, a cyclic organic group, and an alkoxycarbonyl group. Examples of the halogen atom include a fluorine atom, a chlorine atom, a bromine atom, and an iodine atom. Among these, a fluorine atom, a chlorine atom, and a bromine atom are preferable. Examples of the cyclic organic group include a cycloalkyl group, an aromatic hydrocarbon group, and a heterocyclyl group. Specific examples of the cycloalkyl group are the same as suitable examples in the case where $R^{b22}$ is a cycloalkyl group. Specific examples of the aromatic hydrocarbon group include a phenyl group, a naphthyl group, a biphenylyl group, an anthryl group, and a phenanthryl group. Specific examples of the heterocyclyl group are the same as suitable examples in the case where $R^{b22}$ is a heterocyclyl group. When $R^{b22}$ is an alkoxycarbonyl group, an alkoxy group included in the alkoxycarbonyl group may be a straight chain or branched chain group, preferably a straight chain group. The number of carbon atoms of an alkoxy group included in the alkoxycarbonyl group is preferably 1 to 10, and more preferably 1 to 6.

When the chain alkyl group has a substituent, the number of substituents is not particularly limited. The number of substituents preferably varies depending on the number of carbon atoms of the chain alkyl group. The number of substituents is typically 1 to 20, preferably 1 to 10, and more preferably 1 to 6.

When $R^{b23}$ and $R^{b224}$ are cyclic organic groups, the cyclic organic groups may be an alicyclic group or an aromatic group. Examples of the cyclic organic group include an aliphatic cyclic hydrocarbon group, an aromatic hydrocarbon group, and a heterocyclyl group. When $R^{b223}$ and $R^{b224}$ are cyclic organic groups, the substituent, with which the cyclic organic group is optionally substituted, is the same as in the case where $R^{b23}$ and $R^{b24}$ are chain alkyl groups.

When $R^{b23}$ and $R^{b24}$ are aromatic hydrocarbon groups, the aromatic hydrocarbon group is preferably a phenyl group, or a group formed by bonding multiple benzene rings through a carbon-carbon bond, or a group formed by condensing multiple benzene rings. When the aromatic hydrocarbon group is a phenyl group, or a group formed by bonding or condensing multiple benzene rings, the number of rings of a benzene ring included in the aromatic hydrocarbon group is not particularly limited, and is preferably 3 or less, more preferably 2 or less, and particularly preferably 1. Preferred specific examples of the aromatic hydrocarbon group include a phenyl group, a naphthyl group, a biphenylyl group, an anthryl group, and a phenanthryl group.

When $R^{b23}$ and $R^{b24}$ are aliphatic cyclic hydrocarbon groups, the aliphatic cyclic hydrocarbon group may be a monocyclic or polycyclic group. The number of carbon atoms of the aliphatic cyclic hydrocarbon group is not particularly limited, and is preferably 3 to 20, and more preferably 3 to 10. Examples of the monocyclic cyclic hydrocarbon group include cyclopropyl group, a cyclobutyl group, a cyclopentyl group, a cyclohexyl group, a cycloheptyl group, a cyclooctyl group, a norbornyl group, a isobornyl group, a tricyclononyl group, a tricyclodecyl group, a tetracyclododecyl group, and an adamantyl group.

When $R^{b23}$ and $R^{b24}$ are heterocyclyl groups, the heterocyclyl group is a 5- or 6-membered monocycle containing one or more N, S, and O, or a heterocyclyl group in which these monocycles are condensed, or the monocycle and a benzene ring are condensed. When the heterocyclyl group is a condensed ring, the number of rings is 3 or less. The heterocyclyl group may be an aromatic group (heteroaryl group) or a non-aromatic group. Examples of the heterocycle constituting the heterocyclyl group include furan, thiophene, pyrrole, oxazole, isoxazole, triazole, thiadiazole, isothiazole, imidazole, pyrazole, triazole, pyridine, pyrazine, pyrimidine, pyridazine, benzofuran, benzothiophene, indole, isoindole, indolizine, benzoimidazole, benzotriazole, benzoxazole, benzothiazole, carbazole, purine, quinoline, isoquinoline, quinazoline, phthalazine, cinnoline, quinoxaline, piperidine, piperazine, morpholine, piperidine, tetrahydropyran, and tetrahydrofuran.

$R^{b23}$ and $R^{b24}$ may be bonded to one another to form a ring. The group composed of the ring formed by $R^{b23}$ and $R^{b24}$ is preferably a cycloalkylidene group. When $R^{b23}$ and $R^{b24}$ are bonded to form a cycloalkylidene group, the ring constituting the cycloalkylidene group is preferably a 5- to 6-membered ring, and more preferably a 5-membered ring.

When the group formed by bonding $R^{b23}$ and $R^{b24}$ is a cycloalkylidene group, the cycloalkylidene group may be condensed with one or more other rings. Examples of the ring which may be condensed with the cycloalkylidene group include a benzene ring, a naphthalene ring, a cyclobutane ring, a cyclopentane ring, a cyclohexane ring, a cycloheptane ring, a cyclooctane ring, a furan ring, a thiophene ring, a pyrrole ring, a pyridine ring, a pyrazine ring, a pyrimidine ring, and the like.

Examples of a suitable group among $R^{b23}$ and $R^{b24}$ described above include a group represented by the formula: -$A^{b1}$-$A^{b2}$. In the formula, $A^{b1}$ is a straight chain alkylene group, and $A^{b2}$ is an alkoxy group, a cyano group, a halogen atom, a halogenated alkyl group, a cyclic organic group, or an alkoxycarbonyl group.

The number of carbon atoms of the straight chain alkylene group for $A^{b1}$ is preferably 1 to 10, and more preferably 1 to 6. When $A^{b2}$ is an alkoxy group, the alkoxy group may be a straight chain or branched chain alkoxy group, preferably a straight chain alkoxy group. The number of carbon atoms of the alkoxy group is preferably 1 to 10, and more preferably 1 to 6. When $A^{b2}$ is a halogen atom, a fluorine atom, a chlorine atom, a bromine atom, or an iodine atom is preferable, and a fluorine atom, a chlorine atom, or a bromine atom is more preferable. When $A^{b2}$ is a halogenated alkyl group, a halogen atom included in the halogenated alykyl group is preferably a fluorine atom, a chlorine atom, a bromine atom, or an iodine atom, and more preferably is a fluorine atom, a chlorine atom, or a bromine atom. The halogenated alkyl group may be a straight chain or branched chain halogenated alkyl group, preferably a straight chain halogenated alkyl group. When $A^{b2}$ is a cyclic organic group, examples of the cyclic organic group are the same as the cyclic organic group possessed by $R^{b23}$ and $R^{b24}$ as a substituent. When $A^{b2}$ is an alkoxycarbonyl group, examples of the alkoxycarbonyl group are the same as the alkoxycarbonyl group possessed by $R^{b23}$ and $R^{b24}$ as a substituent.

Suitable specific examples of $R^{b23}$ and $R^{b24}$ include alkyl groups such as an ethyl group, an n-propyl group, an n-butyl group, an n-hexyl group, an n-heptyl group, and an n-octyl group; alkoxyalkyl groups such as a 2-methoxyethyl group, a 3-methoxy-n-propyl group, a 4-methoxy-n-butyl group, a 5-methoxy-n-pentyl group, a 6-methoxy-n-hexyl group, a 7-methoxy-n-heptyl group, a 8-methoxy-n-octyl group, a 2-ethoxyethyl group, a 3-ethoxy-n-propyl group, a 4-ethoxy-n-butyl group, a 5-ethoxy-n-pentyl group, a 6-ethoxy-n-hexyl group, a 7-ethoxy-n-heptyl group, and a 8-ethoxy-n-octyl group; cyanoalkyl groups such as a 2-cyanoethyl group, a 3-cyano-n-propyl group, a 4-cyano-n-butyl group, a 5-cyano-n-pentyl group, a 6-cyano-n-hexyl group, a 7-cyano-n-heptyl group, and a 8-cyano-n-octyl group; phenylalkyl groups such as a 2-phenylethyl group, a 3-phenyl-n-propyl group, a 4-phenyl-n-butyl group, a 5-phenyl-n-pentyl group, a 6-phenyl-n-hexyl group, a 7-phenyl-n-heptyl group, and a 8-phenyl-n-octyl group; cycloalkylalkyl groups such as a 2-cyclohexylethyl group, a 3-cyclohexyl-n-propyl group, a 4-cyclohexyl-n-butyl group, a 5-cyclohexyl-n-pentyl group, a 6-cyclohexyl-n-hexyl group, a 7-cyclohexyl-n-heptyl group, a 8-cyclohexyl-n-octyl group, a 2-cyclopentylethyl group, a 3-cyclopentyl-n-propyl group, a 4-cyclopentyl-n-butyl group, a 5-cyclopentyl-n-pentyl group, a 6-cyclopentyl-n-hexyl group, a 7-cyclopentyl-n-heptyl group, and a 8-cyclopentyl-n-octyl group; alkoxycarbonylalkyl groups such as a 2-methoxycarbonylethyl group, a 3-methoxycarbonyl-n-propyl group, a 4-methoxycarbonyl-n-butyl group, a 5-methoxycarbonyl-n-pentyl group, a 6-methoxycarbonyl-n-hexyl group, a 7-methoxycarbonyl-n-heptyl group, a 8-methoxycarbonyl-n-octyl group, a 2-ethoxycarbonylethyl group, a 3-ethoxycarbonyl-n-propyl group, a 4-ethoxycarbonyl-n-butyl group, a 5-ethoxycarbonyl-n-pentyl group, a 6-ethoxycarbonyl-n-hexyl group, a 7-ethoxycarbonyl-n-heptyl group, and a 8-ethoxycarbonyl-n-octyl group; and halogenated alkyl groups such as a 2-chloroethyl group, a 3-chloro-n-propyl group, a 4-chloro-n-butyl group, a 5-chloro-n-pentyl group, a 6-chloro-n-hexyl group, a 7-chloro-n-heptyl group, a 8-chloro-n-octyl group, a 2-bromoethyl group, a 3-bromo-n-propyl group, a 4-bromo-n-butyl group, a 5-bromo-n-pentyl group, a 6-bromo-n-hexyl group, a 7-bromo-n-heptyl group, a 8-bromo-n-octyl group, a 3,3,3-trifluoropropyl group, and a 3,3,4,4,5,5,5-heptafluoro-n-pentyl group.

Among groups mentioned above, groups suitable as $R^{b23}$ and $R^{b24}$ are an ethyl group, an n-propyl group, an n-butyl group, an n-pentyl group, a 2-methoxyethyl group, a 2-cyanoethyl group, a 2-phenylethyl group, a 2-cyclohexylethyl group, a 2-methoxycarbonylethyl group, a 2-chloroethyl group, a 2-bromoethyl group, a 3,3,3-trifluoropropyl group, and a 3,3,4,4,5,5,5-heptafluoro-n-pentyl group.

In the same manner as $R^{b22}$, examples of a suitable organic group for $R^{b25}$ include an alkyl group, an alkoxy group, a cycloalkyl group, a cycloalkoxy group, a saturated aliphatic acyl group, an alkoxycarbonyl group, a saturated aliphatic acyloxy group, an optionally substituted phenyl group, an optionally substituted phenoxy group, an optionally substituted benzoyl group, an optionally substituted phenoxycarbonyl group, an optionally substituted benzoyloxy group, an optionally substituted phenylalkyl group, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group, an optionally substituted heterocyclyl group, an optionally substituted heterocyclylcarbonyl group, an amino group substituted with one or two organic groups, a morpholin-1-yl group, a piperazin-1-yl group, and the like. Specific examples of these groups are the same as those described for $R^{b22}$. $R^{b25}$ is also preferably a cycloalkylalkyl group, a phenoxyalkyl group which may have a substituent on an aromatic ring, and a phenylthioalkyl group which may have a substituent on an aromatic ring. The substituent which may be possessed by a phenoxyalkyl group and phenylthioalkyl group is the same as the substituent which may be possessed by a phenyl group included in $R^{b22}$.

Among organic groups, $R^{b25}$ is preferably an alkyl group, a cycloalkyl group, an optionally substituted phenyl group or cycloalkylalkyl group, or a phenylthioalkyl group which may have a substituent on an aromatic ring. The alkyl group is preferably an alkyl group having 1 to 20 carbon atoms, more preferably an alkyl group having 1 to 8 carbon atoms, particularly preferably an alkyl group having 1 to 4 carbon atoms, and most preferably a methyl group. Among an optionally substituted phenyl groups, a methylphenyl group is preferable, and a 2-methylphenyl group is more preferable. The number of carbon atoms of the cycloalkyl group included in the cycloalkylalkyl group is preferably 5 to 10, more preferably 5 to 8, and particularly preferably 5 or 6. The number of carbon atoms of the alkylene group included in the cycloalkylalkyl group is preferably 1 to 8, more preferably 1 to 4, and particularly preferably 2. Among cycloalkylalkyl groups, a cyclopentylethyl group is preferable. The number of carbon atoms of the alkylene group included in the phenylthioalkyl group which may have a substituent on an aromatic ring is preferably 1 to 8, more preferably 1 to 4, and particularly preferably 2. Among the phenylthioalkyl groups which may have a substituent on an aromatic ring, a 2-(4-chlorophenylthio)ethyl group is preferable.

$R^{b25}$ is also preferably a group represented by -$A^{b3}$-CO—O-$A^{b4}$. $A^{b3}$ is a divalent organic group, preferably a divalent hydrocarbon group, and more preferably an alkylene group. $A^{b4}$ is a monovalent organic group, and preferably a monovalent hydrocarbon group.

When $A^{b3}$ is an alkylene group, the alkylene group may be a straight chain or branched chain alkylene group, preferably a straight chain alkylene group. When $A^{b3}$ is an alkylene group, the number of carbon atoms of the alkylene group is preferably 1 to 10, more preferably 1 to 6, and particularly preferably 1 to 4.

Suitable examples of $A^{b4}$ include an alkyl group having 1 to 10 carbon atoms, an aralkyl group having 7 to 20 carbon atoms, and an aromatic hydrocarbon group having 6 to 20 carbon atoms. Suitable specific examples of $A^{b4}$ include a methyl group, an ethyl group, an n-propyl group, an isopropyl group, an n-butyl group, an isobutyl group, a sec-butyl group, an tert-butyl group, an n-pentyl group, an n-hexyl group, a phenyl group, a naphthyl group, a benzyl group, a phenethyl group, an α-naphthylmethyl group, a β-naphthylmethyl group, and the like.

Suitable specific examples of the group represented by -$A^{b3}$-CO—O-$A^{b4}$ include a 2-methoxycarbonylethyl group, a 2-ethoxycarbonylethyl group, a 2-n-propyloxycarbonylethyl group, a 2-n-butyloxycarbonylethyl group, a 2-n-pentyloxycarbonylethyl group, a 2-n-hexyloxycarbonylethyl group, a 2-benzyloxycarbonylethyl group, a 2-phenoxycarbonylethyl group, a 3-methoxycarbonyl-n-propyl group, a 3-ethoxycarbonyl-n-propyl group, a 3-n-propyloxycarbonyl-n-propyl group, a 3-n-butyloxycarbonyl-n-propyl group, a 3-n-pentyloxycarbonyl-n-propyl group, a 3-n-hexyloxycarbonyl-n-propyl group, a 3-benzyloxycarbonyl-n-propyl group, a 3-phenoxycarbonyl-n-propyl group, and the like.

While $R^{b25}$ has been described above, $R^{b25}$ is preferably a group represented by the following formula (B9) or (B10):

[Chem. 27]

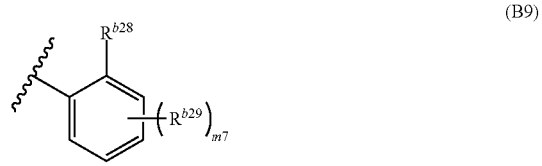

(B9)

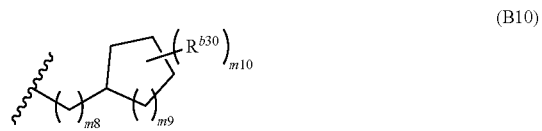

(B10)

in which, in the formulas (B9) and (B10), $R^{b28}$ and $R^{b29}$ each are an organic group; m7 is an integer of 0 to 4; when $R^{b28}$ and $R^{b29}$ are adjacent to each other on the benzene ring, $R^{b28}$ and $R^{b29}$ may be bonded to each other to form a ring; m8 is an integer of 1 to 8; m9 is an integer of 1 to 5; m10 is an integer of 0 to (m9+3); and $R^{b30}$ represents an organic group.

Examples of the organic group for $R^{b28}$ and $R^{b29}$ in the formula (B9) are the same as those in $R^{b22}$. $R^{b28}$ is preferably an alkyl group or a phenyl group. When $R^{b28}$ is an alkyl group, the number of carbon atoms thereof is preferably 1 to 10, more preferably 1 to 5, particularly preferably 1 to 3, and most preferably 1. Namely, $R^{b28}$ is most preferably a methyl group. When $R^{b28}$ and $R^{b29}$ are bonded to form a ring, the ring may be an aromatic ring or an aliphatic ring. Suitable examples of the group represented by the formula (B9) in which $R^{b28}$ and $R^{b29}$ form a ring include a naphthalen-1-yl group, a 1,2,3,4-tetrahydronaphthalen-5-yl group, and the like. In the above formula (B9), m7 is an integer of 0 to 4, preferably 0 or 1, and more preferably 0.

In the above formula (B10), $R^{b30}$ is an organic group. Examples of the organic group include the same groups as the organic groups described for $R^{b22}$. Among the organic groups, an alkyl group is preferable. The alkyl group may be a straight chain or branched chain alkyl group. The number of carbon atoms of the alkyl group is preferably 1 to 10, more preferably 1 to 5, and particularly preferably 1 to 3. Preferable examples of $R^{b30}$ include a methyl group, an ethyl group, an isopropyl group, a butyl group and the like. Among these, a methyl group is more preferable.

In the formula (B10), m9 is an integer of 1 to 5, preferably an integer of 1 to 3, more preferably 1 or 2. In the formula (B10), m10 is 0 to (m9+3), preferably an integer of 0 to 3, more preferably an integer of 0 to 2, particularly preferably 0. In the formula (B10), m8 is an integer of 1 to 8, preferably an integer of 1 to 5, more preferably an integer of 1 to 3, particularly preferably 1 or 2.

In the formula (B8), $R^{b26}$ is a hydrogen atom, an optionally substituted alkyl group having 1 to 11 carbon atoms, or an optionally substituted aryl group. When $R^{b26}$ is an alkyl group, preferable examples of the substituent which may be possessed include a phenyl group, a naphthyl group, or the like. When $R^{b22}$ is an aryl group, preferable examples of the substituent which may be possessed include an alkyl group having 1 to 5 carbon atoms, an alkoxy group, a halogen atom, or the like.

In the formula (B8), preferable examples of $R^{b26}$ include a hydrogen atom, a methyl group, an ethyl group, an n-propyl group, an isopropyl group, an n-butyl group, a phenyl group, a benzyl group, a methylphenyl group, a naphthyl group, and the like. Among these, a methyl group or a phenyl group is more preferable.

The method of producing a compound represented by the formula (B8) is not particularly limited. A compound represented by the formula (B8) is preferably produced by a method comprising a step of converting an oxime group (=N—OH) in a compound represented by the following formula (B11) into an oxime ester group represented by =N—O—COR$^{b26}$. $R^{b26}$ is the same as $R^{b26}$ in the formula (B8).

[Chem. 28]

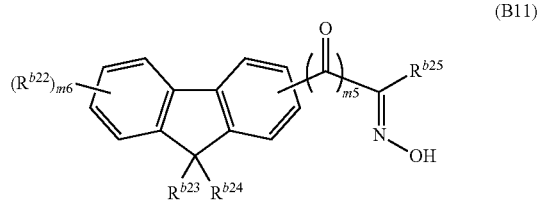

(B11)

($R^{b22}$, $R^{b23}$, $R^{b24}$, $R^{b25}$, m5, and m6 are the same as those in the formula (B8),
m6 is an integer of 0 to 4, and m5 is 0 or 1.)

Therefore, a compound represented by the formula (B11) is useful as an intermediate for synthesis of a compound represented by the formula (B8).

The method for converting an oxime group (=N—OH) into an oxime ester group represented by =N—O—COR$^{b26}$ is not particularly limited. Typical examples of the method include subjecting a hydroxy group in the oxime group to reaction with an acylating agent capable of yielding an acyl group represented by —COR$^{b26}$. Examples of the acylating agent include an acid anhydride represented by ($R^{b26}$CO)$_2$O and an acid halide represented by $R^{b26}$COHal (Hal represents a halogen atom).

A compound represented by the general formula (B8) in which m5 is 0 may be synthesized by the following scheme 1, for example. In scheme 1, a fluorene derivative represented by the following formula (b1-1) is used as a raw material. When $R^{b22}$ is a nitro group or a monovalent organic group, a fluorene derivative represented by the formula (b1-1) may be obtained by introducing, by a well-known method, a substituent $R^{b22}$ into a fluorene derivative substituted with $R^{b23}$ and $R^{b24}$ on the C9. The fluorene derivative substituted with $R^{b23}$ and $R^{b24}$ on the C9 in which $R^{b23}$ and $R^{b24}$ are alkyl groups, for example, may be obtained by reaction between fluorene and an alkylating agent in the presence of an alkali metal hydroxide in an aprotic polar organic solvent as described in Japanese Unexamined Patent Application, Publication No. H06-234668. A 9,9-alkyl-substituted fluorene may be obtained by adding an alkylating agent such as an alkyl halide, an aqueous solution of an alkali metal hydroxide, and a phase-transfer catalyst such as tetrabutylammonium iodide or potassium tert-butoxide to an organic solvent solution of fluorene and carrying out an alkylation reaction.

A fluorene derivative represented by a formula (b1-3) is obtained by introducing an acyl group represented by —CO—$R^{b25}$ into a fluorene derivative represented by the formula (b1-1) by Friedel-Crafts acylation reaction. An acylating agent used for introduction of an acyl group represented by —CO—$R^{b25}$ may be a halocarbonyl compound or an acid anhydride. A preferable acylating agent is a halocarbonyl compound represented by a formula (b1-2). In the formula (b1-2), Hal represents a halogen atom. The position in the fluorene ring to which an acyl group is introduced may be selected by appropriately changing the conditions for Friedel-Crafts reaction or by protecting and deprotecting positions other than the position that is to receive acylation.

Then, by converting a group represented by —CO—$R^{b25}$ in the resulting fluorene derivative represented by the formula (b1-3) into a group represented by —C(=N—OH)—$R^{b25}$, an oxime compound represented by a formula (b1-4) is obtained. The method for converting a group represented by —CO—$R^{b25}$ into a group represented by —C(=N—OH)—$R^{b25}$ is not particularly limited but is preferably oximation with the use of hydroxylamine. By reaction of an oxime compound represented by the formula (b1-4) and an acid anhydride represented by the following formula (b1-5) (($R^{b26}$CO)$_2$O), or an acid halide represented by the following general formula (b1-6) ($R^{b26}$COHal, Hal represents a halogen atom), a compound represented by the following formula (b1-7) may be obtained.

$R^{b22}$, $R^{b23}$, $R^{b24}$, $R^{b25}$, and $R^{b26}$ in the formulas (b1-1), (b1-2), (b1-3), (b1-4), (b1-5), (b1-6), and (b1-7) are the same as those in the formula (B8).

In scheme 1, $R^{b25}$ in each of the formula (b1-2), the formula (b1-3), and the formula (b1-4) may be the same or different from each other. In other words, $R^{b25}$ in the formula (b1-2), the formula (b1-3), and the formula (b1-4) may receive chemical modification during synthesis shown as the scheme 1. Examples of the chemical modification include esterification, etherification, acylation, amidation, halogenation, and substitution of a hydrogen atom in an amino group with an organic group. The chemical modification that $R^{b25}$ may receive is not limited to these chemical modifications.

<Scheme 1>

[Chem. 29]

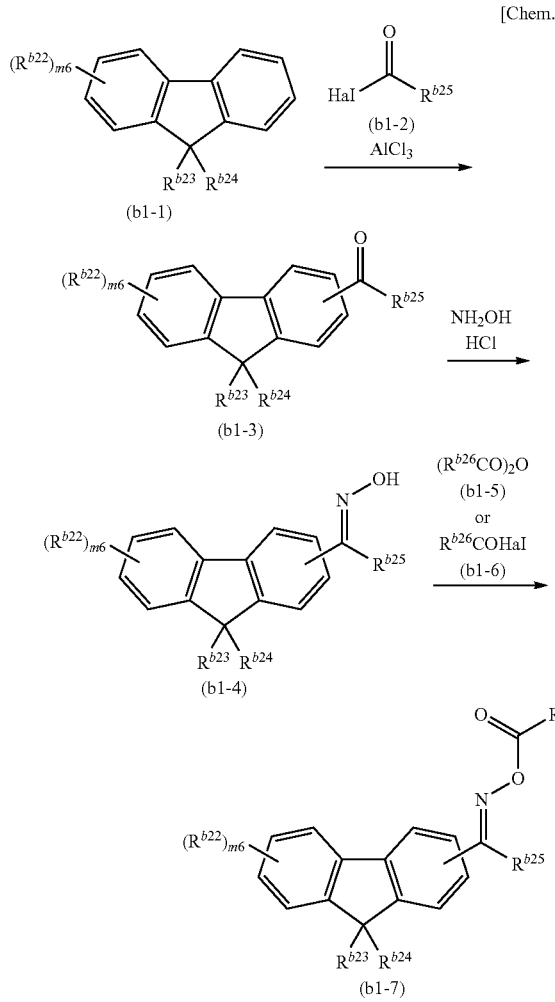

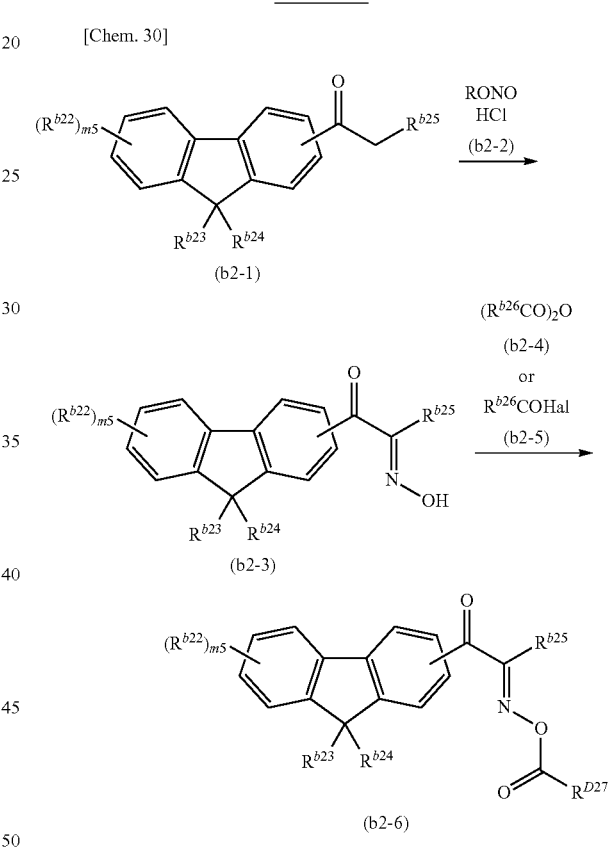

$R^{b26}$ in the following formulas (b2-1), (b2-3), (b2-4), (b2-5), and (b2-6) are the same as those in the general formula (B8). When m5 is 1, there is a tendency that the generation of foreign matter in a pattern formed by using the silicon-containing resin composition comprising a compound represented by the formula (B8) may be reduced.

In scheme 2, $R^{b25}$ in each of the formula (b1-8), the formula (b2-1), and the formula (b2-3) may be the same or different from each other. In other words, $R^{b25}$ in the formula (b1-8), the formula (b2-1), and the formula (b2-3) may receive chemical modification during the synthesis process shown as scheme 2. Examples of the chemical modification include esterification, etherification, acylation, amidation, halogenation, and substitution of a hydrogen atom in an amino group with an organic group. The chemical modification that $R^{b25}$ may receive is not limited to these chemical modifications.

<Scheme 2>

[Chem. 30]

A compound represented by the formula (B8) in which m5 is 1 may be synthesized by the following scheme 2, for example. In scheme 2, a fluorene derivative represented by the following formula (b1-7) is used as a raw material. As in the same method as scheme 1, a fluorene derivative represented by a formula (b2-1) is obtained by introducing an acyl group represented by —CO—CH$_2$—R$^{b25}$ into a compound represented by the formula (b1-1) by Friedel-Crafts reaction. A preferable acylating agent is a carboxylic acid halide represented by the formula (b1-8) (Hal-CO—CH$_2$—R$^{b25}$). Then, by oximation of a methylene group that is present between R$^{b25}$ and the carbonyl group in a compound represented by the formula (b1-7), a ketoxime compound represented by the following formula (b2-3) is obtained. The method of oximation of a methylene group is not particularly limited, but a preferable method is to subject a nitrous ester represented by the following general formula (b2-2) (RONO, R represents an alkyl group having 1 to 6 carbon atoms) to reaction in the presence of hydrochloric acid. Then, by subjecting a ketoxime compound represented by the following formula (b2-3) to reaction with an acid anhydride represented by the following formula (b2-4) ((R$^{b26}$CO)$_2$O) or an acid halide represented by the following general formula (b2-5) (R$^{b26}$COHal, Hal represents a halogen atom), a compound represented by the following formula (b2-6) may be obtained. R$^{b22}$, R$^{b23}$, R$^{b24}$, R$^{b25}$, and Specific examples of a suitable compound represented by the formula (B8) include the following compounds 1 to 41.

Compound 1

[Chem. 31]

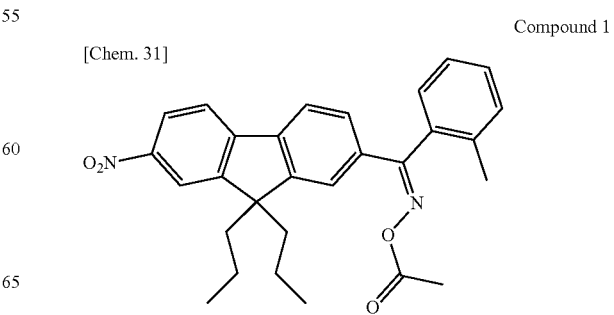

Compound 2
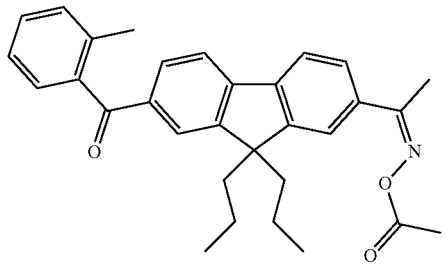
Compound 3
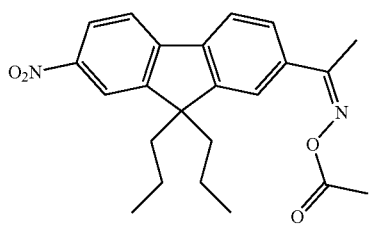
Compound 4
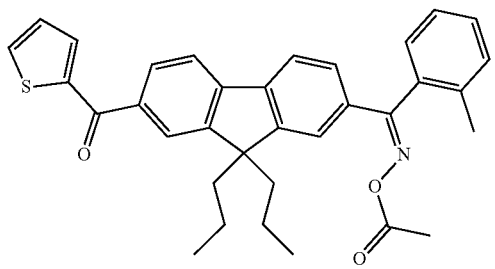
Compound 5
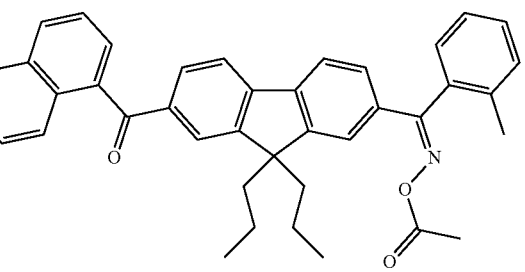
Compound 6
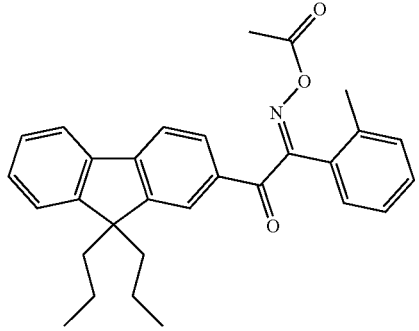
Compound 7
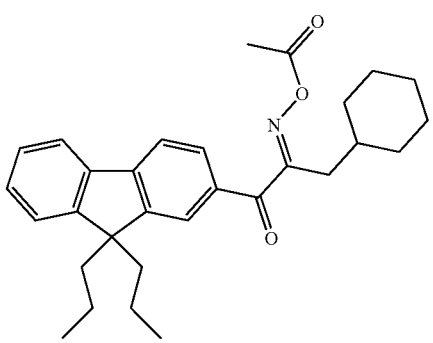
Compound 8
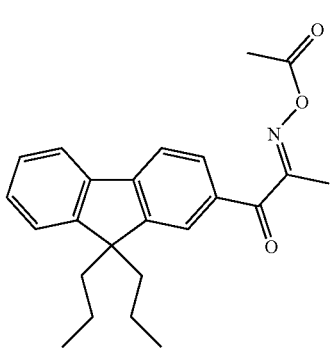
Compound 9
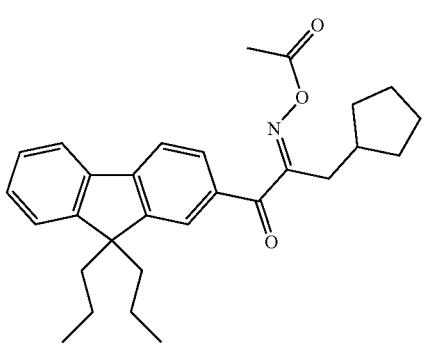
Compound 10
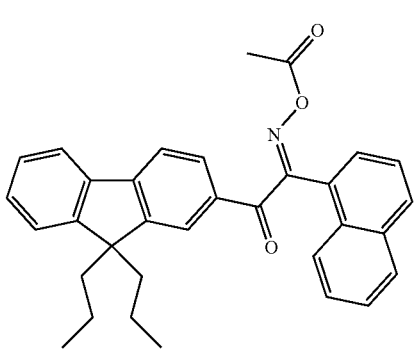

Compound 11
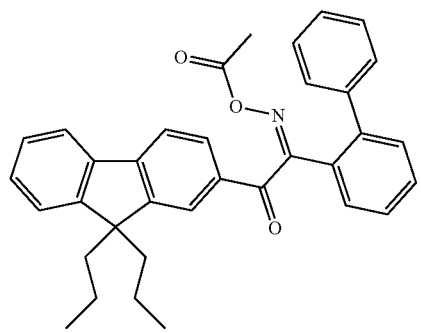
Compound 12
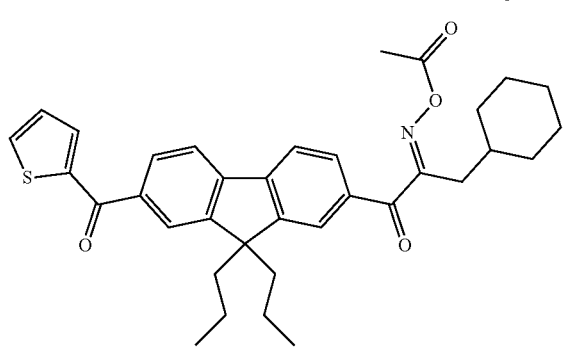
Compound 13
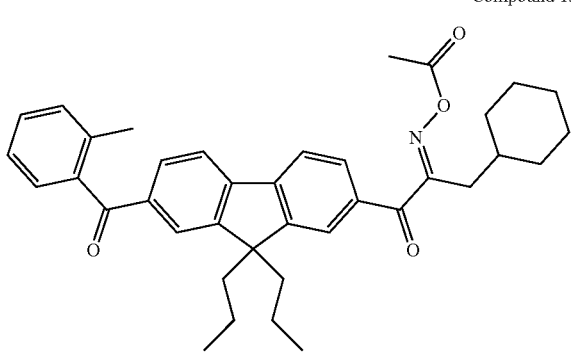
Compound 14
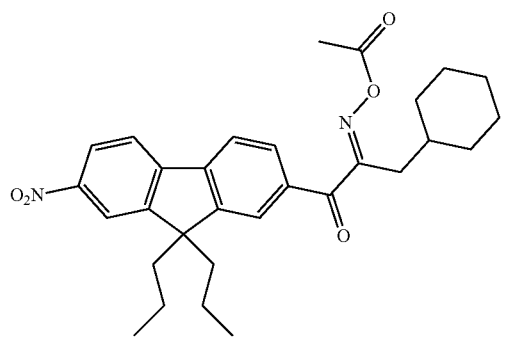
Compound 15
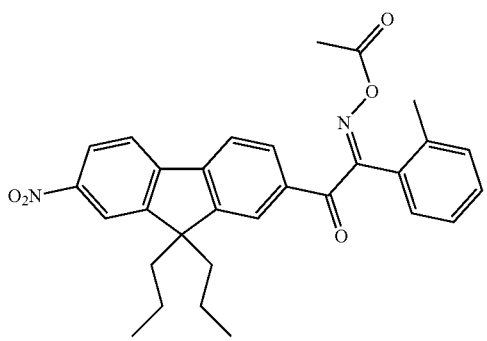
Compound 16
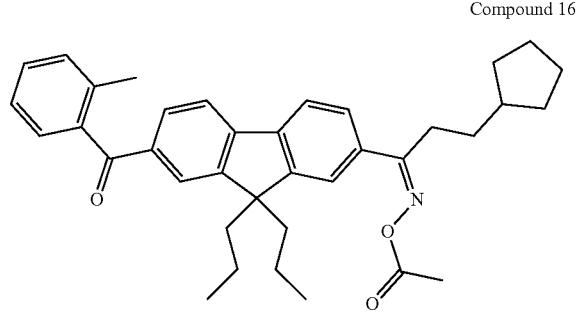
Compound 17
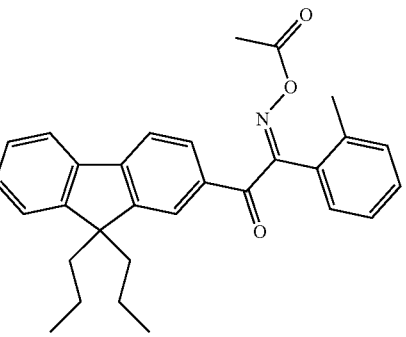
Compound 18
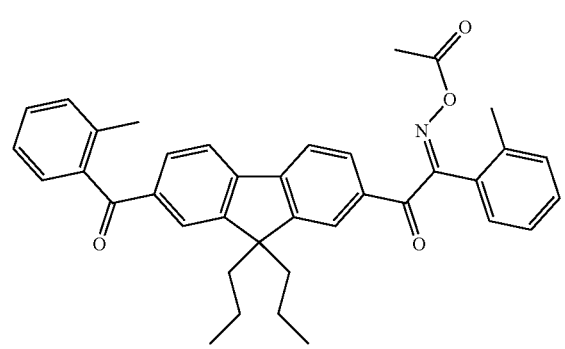

Compound 19
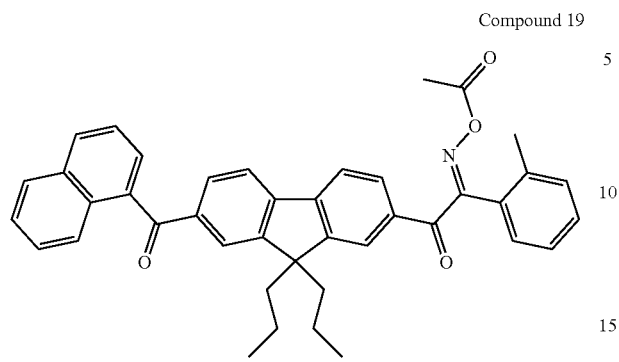
Compound 20
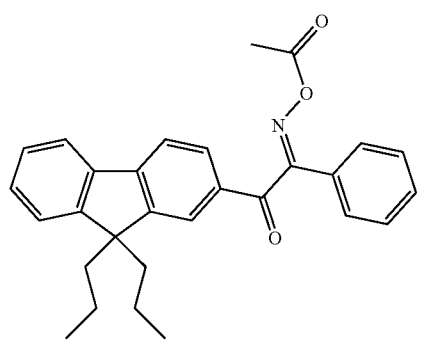
Compound 21
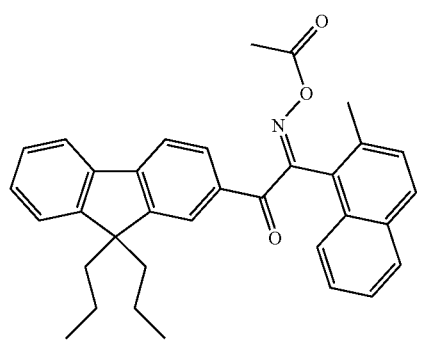
Compound 22
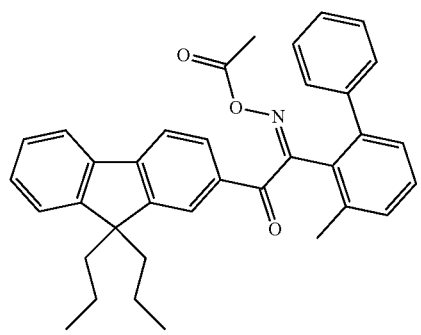
[Chem. 32]
Compound 23
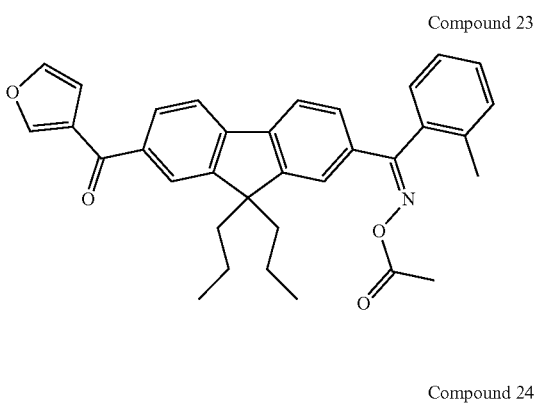
Compound 24
Compound 25
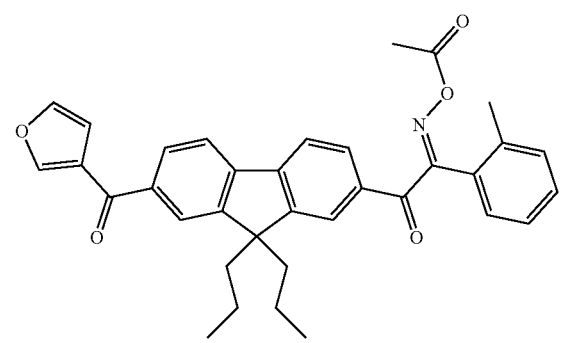
Compound 26
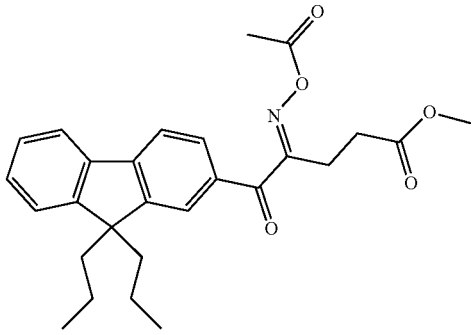

Compound 27
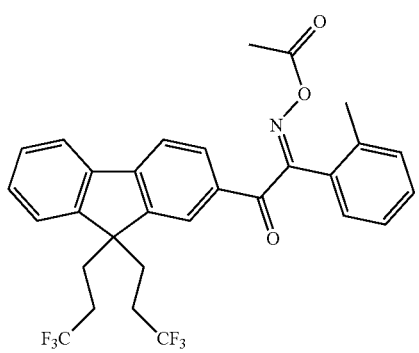
Compound 28
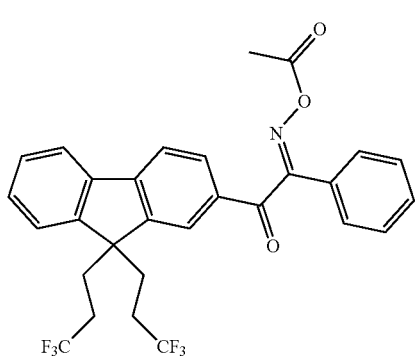
Compound 29
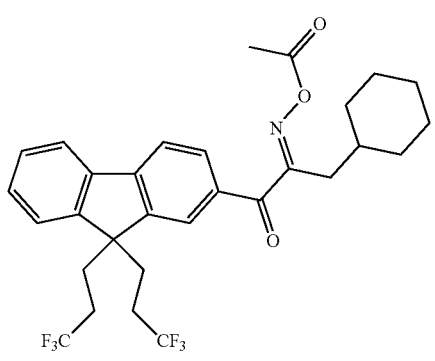
Compound 30
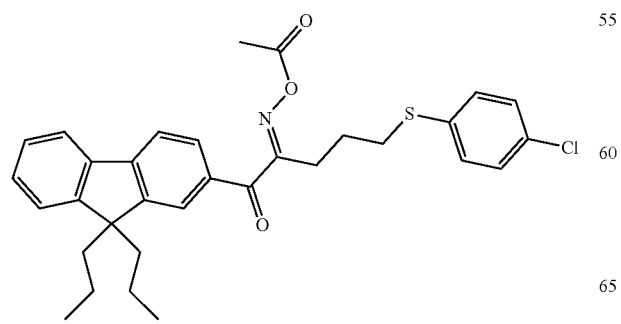
Compound 31
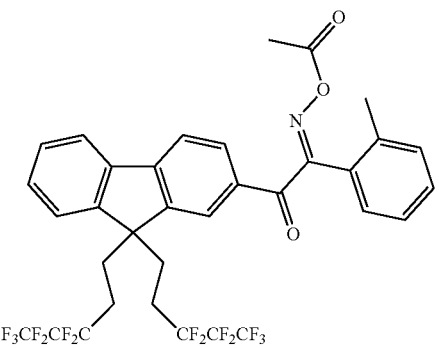
Compound 32
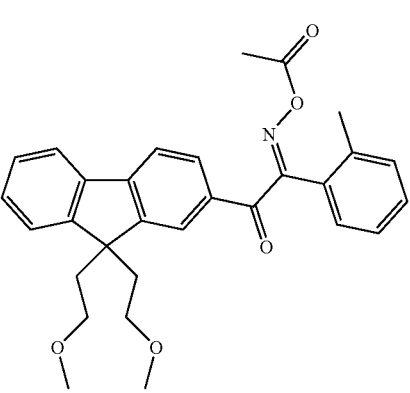
Compound 33
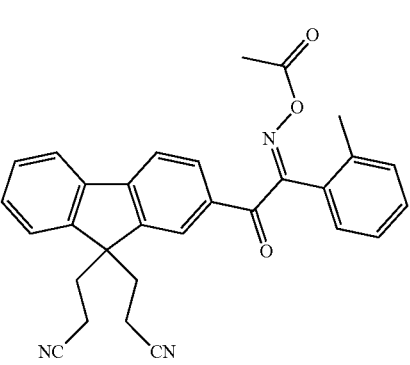
Compound 34
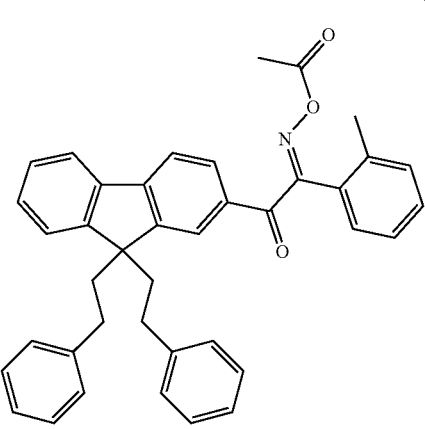

Compound 35

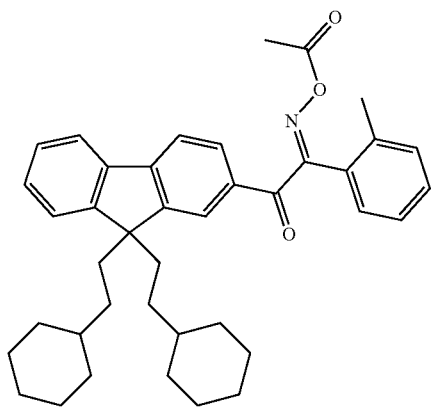

Compound 36

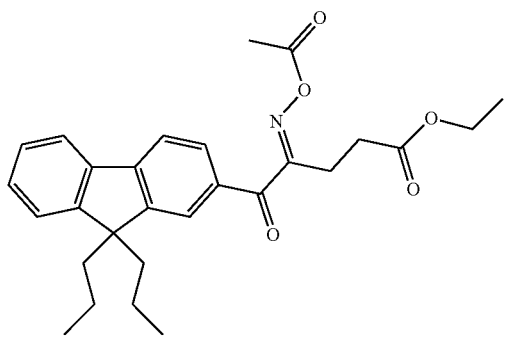

Compound 37

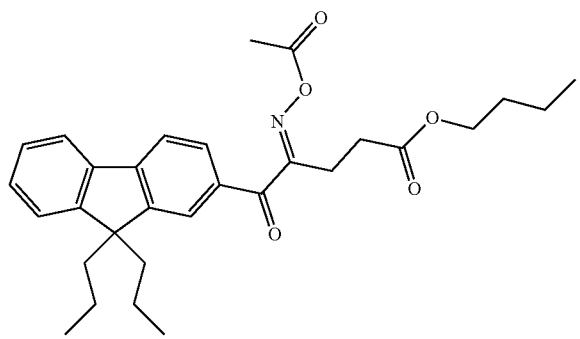

Compound 38

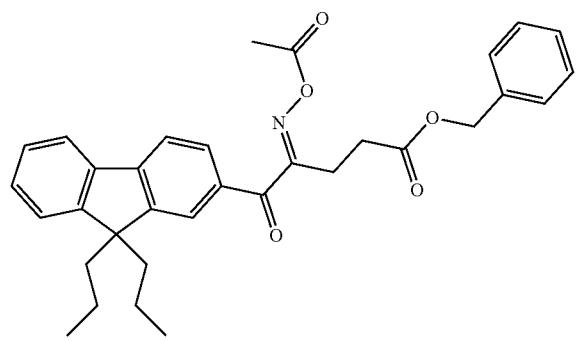

Compound 39

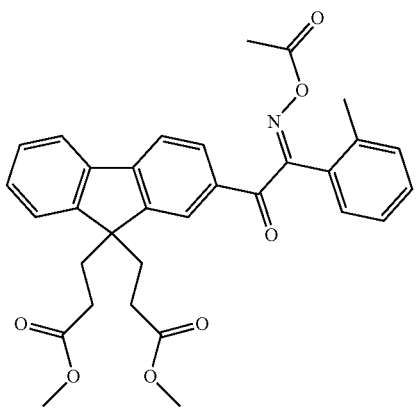

Compound 40

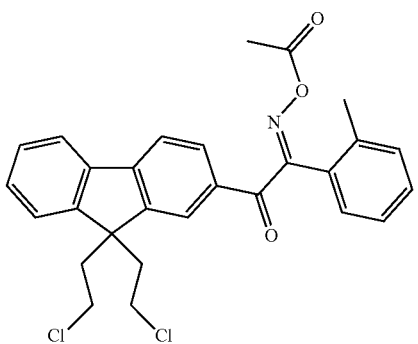

Compound 41

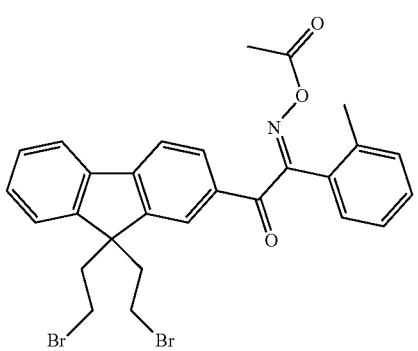

The (B) curing agent in the silicon-containing resin composition may contain two or more curing agents in different categories or of different types. A typical content of the (B) curing agent in the silicon-containing resin composition is preferably 0.01 to 40% by mass, more preferably 0.1 to 20% by mass, particularly preferably 1 to 10% by mass relative to the total mass of the composition.

[(C) Nitroxy Compound]

The silicon-containing resin composition may comprise (C) a nitroxy compound. It is preferable that the silicon-containing resin composition comprise the (C) nitroxy compound because in this case, it is possible to form a silica-based coating film with a low dielectric constant. It is preferable that the silicon-containing resin composition comprise the (C) nitroxy compound, because in this case, the amount of a residue remaining in the resulting silica-based coating film (this residue is an impurity derived from the silica-based coating film) may be reduced even when the temperature for baking for formation of the silica-based coating film is low, for example, at 250° C. or less (for example, within the range from 200° C. or more to 250° C. or less). In the case in which the amount of a residue remaining in the silica-based coating film is low, the generation of gas derived from the residue of the silica-based coating film or from a degradation product of the residue in the film is reduced even when the silica-based coating film is in a high-temperature atmosphere or in a reduced-pressure atmosphere.

The (C) nitroxy compound is not particularly limited as far as it is stable as a nitroxide radical. Examples of a suitable (C) nitroxy compound include a compound having a structure represented by the following formula (c1).

[Chem. 33]

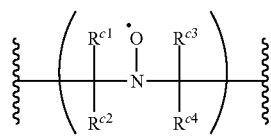

(c1)

In the formula (c1), $R^{c1}$, $R^{c2}$, $R^{c3}$, and $R^{c4}$ each independently represent a hydrogen atom or an organic group having 1 to 10 carbon atoms. $R^{c1}$ and $R^{c2}$ may be bonded to each other to form a ring. $R^{c3}$ and $R^{c4}$ may be bonded to each other to form a ring. When the silicon-containing resin composition comprises a compound having a structure represented by the formula (c1) as the (C) nitroxy compound, a silica-based coating film with a lower dielectric constant tends to be obtained. In the formula (c1), it is preferable that $R^{c1}$, $R^{c2}$, $R^{c3}$, and $R^{c4}$ each independently represent an alkyl group or an alkyl group substituted with a heteroatom. The alkyl group is preferably a methyl group, an ethyl group, an n-propyl group, or an isopropyl group. Examples of a suitable heteroatom include a halogen atom, an oxygen atom, a sulfur atom, and a nitrogen atom.

Specific examples of a suitable, preferable (C) nitroxy compound include di-tert-butyl nitroxide, di-1,1-dimethylpropyl nitroxide, di-1,2-dimethylpropyl nitroxide, di-2,2-dimethylpropyl nitroxide, and a compound represented by the following formula (c2), (c3), or (c4). Among these, for easily attaining a lower dielectric constant of the resulting silica-based coating film, a compound represented by the following formula (c2), (c3), or (c4) is more preferable.

[Chem. 34]

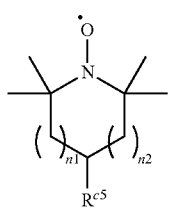

(c2)

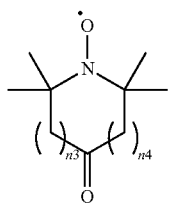

(c3)

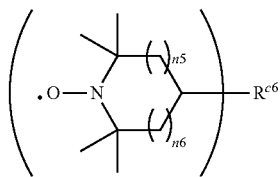

(c4)

In the formulas (c2), (c3), and (c4), $R^{c5}$ represents a hydrogen atom, an alkyl group having 1 to 12 carbon atoms, a hydroxy group, an amino group, a carboxy group, a cyano group, an alkyl group substituted with a heteroatom, or a monovalent organic group bonded via an ether bond, an ester bond, an amide bond, or a urethane bond. $R^{c6}$ represents a divalent or trivalent organic group. Each of n1 and n2 is an integer that satisfies $1 \leq n1+n2 \leq 2$. Each of n3 and n4 is an integer that satisfies $1 \leq n3+n4 \leq 2$. Each of n5 and n6 is an integer that satisfies $1 \leq n5+n6 \leq 2$.

n7 is 2 or 3.

Specific examples of a suitable compound represented by the formula (c2) include the following compounds. In the following formulas, $R^{c7}$s each independently represent an optionally substituted alkyl group having 1 to 20 carbon atoms, an optionally substituted aromatic group, or an optionally substituted alicyclic group.

[Chem. 35]

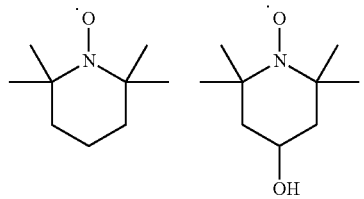

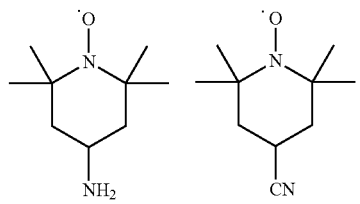

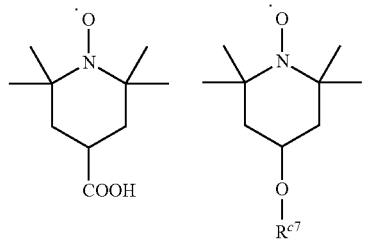

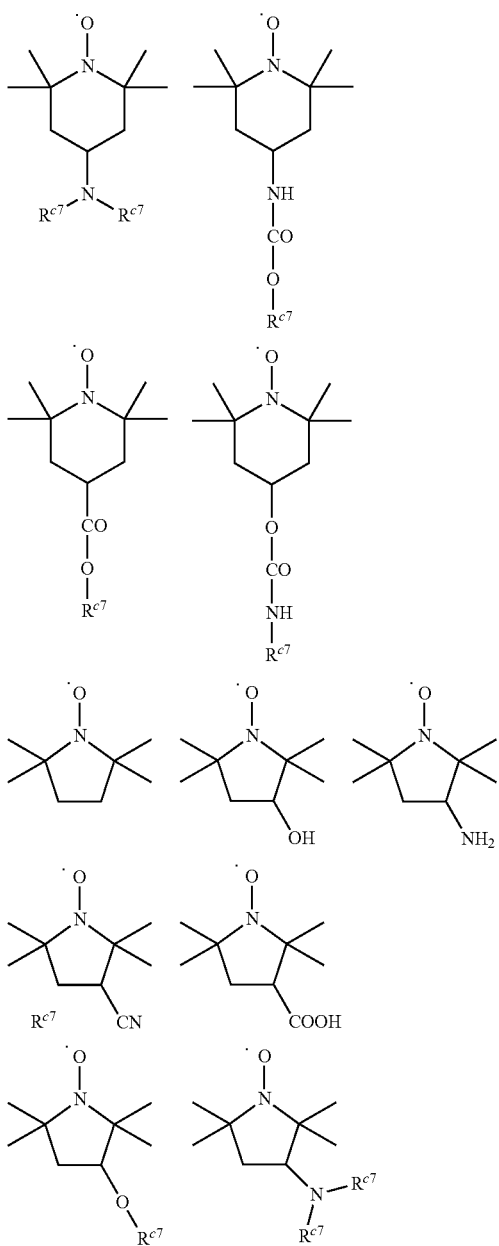
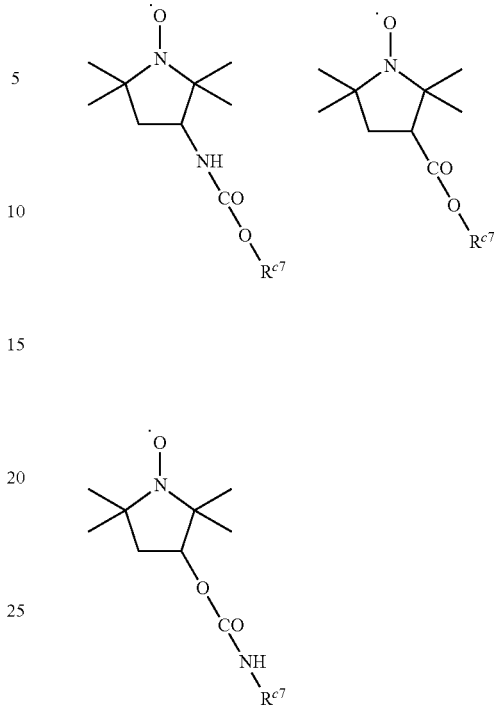
Specific examples of a suitable compound represented by the formula (c3) include the following compounds.
[Chem. 36]
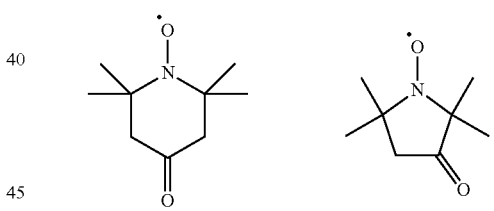
Specific examples of a suitable compound represented by the formula (c4) include the following compounds.
[Chem. 37]
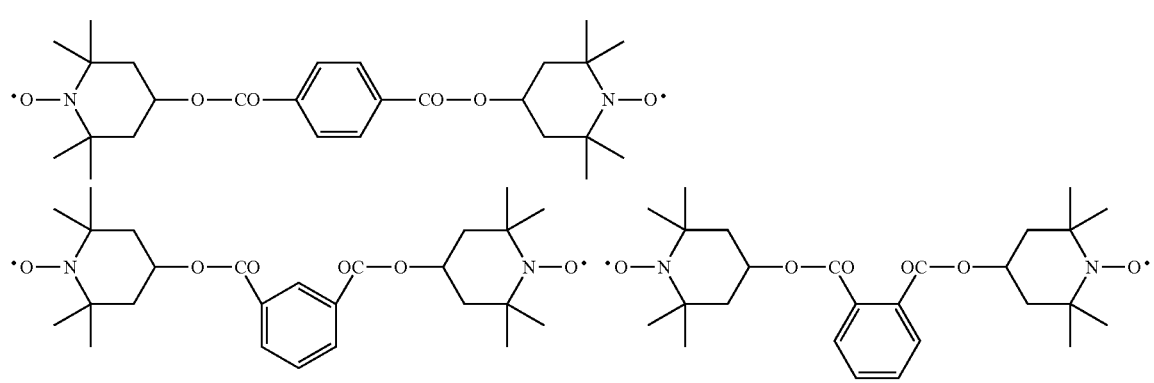

-continued

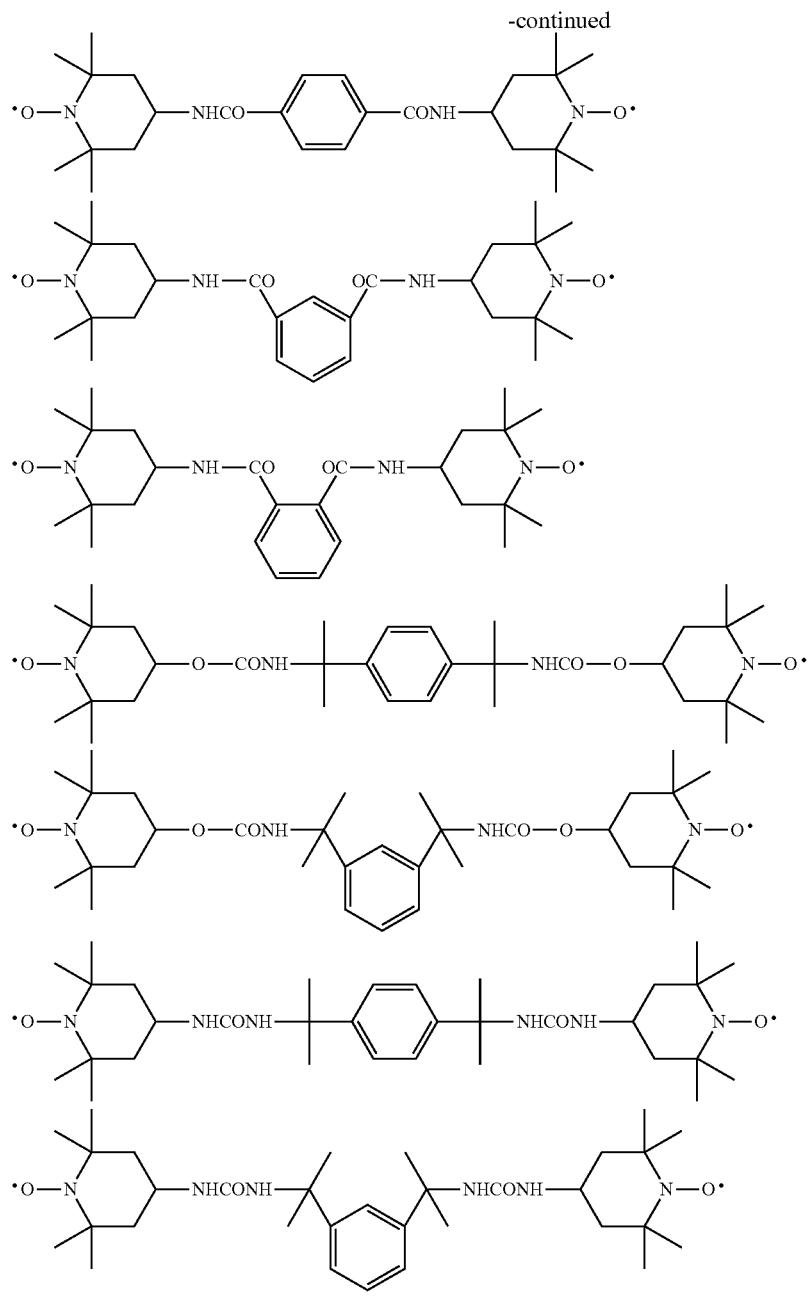

For easily attaining a lower dielectric constant of the resulting silica-based coating film, examples of further preferable compounds as the (C) nitroxy compound include 2,2,6,6-tetramethylpiperidine 1-oxyl free radical, 4-hydroxy-2,2,6,6-tetramethylpiperidine 1-oxyl free radical, 4-amino-2,2,6,6-tetramethylpiperidine 1-oxyl free radical, 4-carboxy-2,2,6,6-tetramethylpiperidine 1-oxyl free radical, 4-cyano-2,2,6,6-tetramethylpiperidine 1-oxyl free radical, 4-(methacrylic acid)-2,2,6,6-tetramethylpiperidine 1-oxyl free radical, 4-(acrylic acid)-2,2,6,6-tetramethylpiperidine 1-oxyl free radical, 4-oxo-2,2,6,6-tetramethylpiperidine 1-oxyl free radical, 3-carboxy-2,2,5,5-tetramethylpyrrolidine 1-oxyl free radical, 4-acetamide-2,2,6,6-tetramethylpiperidine 1-oxyl free radical, 4-(2-chloroacetamide)-2,2,6,6-tetramethylpiperidine 1-oxyl free radical, 4-hydroxy-2,2,6,6-tetramethylpiperidine 1-oxylbenzoate free radical, 4-isothiocyanato-2,2,6,6-tetramethylpiperidine 1-oxyl free radical, 4-(2-iodoacetamide)-2,2,6,6-tetramethylpiperidine 1-oxyl free radical, and 4-methoxy-2,2,6,6-tetramethylpiperidine 1-oxyl free radical. The (C) nitroxy compound may be used alone or as a combination of two or more of these.

The content of the (C) nitroxy compound in the silicon-containing resin composition may be very small. For easily attaining a lower dielectric constant of the resulting silica-based coating film, the content of the (C) nitroxy compound in the silicon-containing resin composition is preferably 0.005% by mass or more, more preferably 0.009% by mass or more relative to the total mass of all the components of the silicon-containing resin composition except for the (S) solvent. The content of the (C) nitroxy compound in the silicon-containing resin composition is preferably 2% by mass or less, more preferably 1% by mass or less relative to the total mass of all the components of the silicon-containing resin composition except for the (S) solvent.

[(S) Solvent]

The silicon-containing resin composition comprises the (S) solvent. The (S) solvent contains a cycloalkyl acetate represented by the following formula (S1). When the silicon-containing resin composition comprises the (S) solvent containing a cycloalkyl acetate represented by the following formula (S1) in addition to the (A) silicon-containing resin, crack formation in the resulting silica-based coating film formed by using the silicon-containing resin composition tends to be inhibited.

[Chem. 38]

(S1)

(In the formula (S1), $R^{s1}$ represents an alkyl group having 1 to 3 carbon atoms; p is an integer of 1 to 6; and q is an integer of 0 to (p+1).)

Specific examples of a cycloalkyl acetate represented by the formula (S1) include cyclopropyl acetate, cyclobutyl acetate, cyclopentyl acetate, cyclohexyl acetate, cycloheptyl acetate, and cyclooctyl acetate. Among these, cyclooctyl acetate is preferable because it is readily available and tends to inhibit crack formation. The (S) solvent may contain two or more cycloalkyl acetates represented by the formula (S1) in combination.

The content of a cycloalkyl acetate represented by the formula (S1) in the (S) solvent is not particularly limited as far as objects of the present invention are not inhibited. The content of a cycloalkyl acetate represented by the formula (S1) in the (S) solvent is typically 30% by mass or more, for example, preferably 50% by mass or more, more preferably 70% by mass or more, particularly preferably 90% by mass or more, and may be 100% by mass.

When the (S) solvent contains a solvent other than a cycloalkyl acetate represented by the formula (S1), the type of the solvent other than a cycloalkyl acetate represented by the formula (S1) is not particularly limited as far as objects of the present invention are not inhibited.

Examples of the solvent other than a cycloalkyl acetate represented by the formula (S1) that the (S) solvent may contain include
alcohols such as methanol, ethanol, propanol, and n-butanol;
polyhydric alcohols such as ethylene glycol, diethylene glycol, propylene glycol, and dipropylene glycol;
ketones such as acetone, methyl ethyl ketone, cyclohexanone, methyl-n-amyl ketone, methyl isoamyl ketone, and 2-heptanone; lactone-ring-containing organic solvents such as γ-butyrolactone;
polyhydric alcohol derivatives, including ester-bond-containing compounds such as ethylene glycol monoacetate, diethylene glycol monoacetate, propylene glycol monoacetate, and dipropylene glycol monoacetate and ether-bond-containing compounds such as monoalkyl ethers (for example, monomethyl ether, monoethyl ether, monopropyl ether, and monobutyl ether) or monophenyl ethers of the above polyhydric alcohols and the above ester-bond-containing compounds;
cyclic ethers such as dioxane and esters such as methyl lactate, ethyl lactate, methyl acetate, ethyl acetate, butyl acetate, methyl pyruvate, ethyl pyruvate, methyl methoxypropionate, and ethyl ethoxypropionate;
aromatic organic solvents such as anisole, ethyl benzyl ether, cresyl methyl ether, diphenyl ether, dibenzyl ether, phenetole, butyl phenyl ether, ethylbenzene, diethylbenzene, amylbenzene, isopropylbenzene, toluene, xylene, cymene, and mesitylene; and
nitrogen-containing organic solvents such as N,N,N',N'-tetramethylurea, N,N,2-trimethylpropionamide, N,N-dimethylacetamide, N,N-dimethylformamide, N,N-diethylacetamide, N,N-diethylformamide, 1,3-dimethyl-2-imidazolidinone, N-methylpyrrolidone, and N-ethylpyrrolidone. Two or more of these solvents may be used in combination. The proportion of the solvent other than a cycloalkyl acetate represented by the formula (S1) in the entire (S) solvent may be appropriately determined to be 70% by mass or less, for example, preferably 0.01 to 55% by mass, more preferably 1 to 50% by mass.

Among the solvents other than a cycloalkyl acetate represented by the formula (S1), propylene glycol monomethyl ether acetate (PGMEA), propylene glycol monomethyl ether (PGME), N,N,N',N'-tetramethylurea, and butanol are preferable.

When the silicon-containing resin composition comprises a polysilane as the (A) silicon-containing resin, for inhibiting cracks or easily attaining a low dielectric constant of the resulting silica-based coating film, the moisture content of the silicon-containing resin composition is preferably 0.5% by mass or less, more preferably 0.3% by mass or less, particularly preferably less than 0.3% by mass. Moisture of the silicon-containing resin composition is derived from the (S) solvent in most cases. Therefore, the (S) solvent is preferably dehydrated so that the moisture content of the silicon-containing resin composition falls within the above range.

The amount of the (S) solvent to be used is not particularly limited as far as objects of the present invention are not inhibited. From the viewpoint of film-forming properties, the amount of the (S) solvent to be used is determined so that the solid content concentration of the silicon-containing resin composition is preferably 1 to 50% by mass, more preferably 10 to 40% by mass.

[Other Components]

The silicon-containing resin composition may contain, in addition to the (A) silicon-containing resin and the (S) solvent, various components that are conventionally added to a silicon-containing resin composition used in various applications. Examples of those other components include a photopolymerization initiator, an acid generator, a base generator, a catalyst, a silane coupling agent, an adhesion promoter, a dispersant, a surfactant, an ultraviolet absorber, an antioxidant, a defoaming agent, a viscosity modifier, and a colorant. These components are blended, each in a typical amount, to the silicon-containing resin composition.

<Method of Producing Silicon-Containing Resin Composition>

The method of producing the silicon-containing resin composition is not particularly limited. A typical method is to uniformly mix the components described above each in a predetermined amount and make the solid matter dissolved in the (S) solvent to obtain the silicon-containing resin composition. For removal of very small insoluble matter, the silicon-containing resin composition may be filtered through a filter with a desired pore size.

<Method for Film Formation>

Examples of the method for forming a silica-based coating film using the silicon-containing resin composition include a method comprising:
a step of applying the silicon-containing resin composition to a substrate to form a coating film; and
a step of baking the resulting coating film.

When the silicon-containing resin composition comprises a curing agent that degrades and generates a base by the action of light, it is preferable that the above method further comprise an exposure step. The exposure step may be carried out instead of the baking step or in combination of the baking step. In the exposure step, the formed coating film may be selectively subjected to exposure, for example. When the selective exposure step is carried out, a development step may further be carried out. The formed coating film may be subjected to imprint lithography, for example. When imprint lithography is carried out, examples of the method of imprint lithography include a method comprising;
a step of applying the silicon-containing resin composition to a substrate to form a coating film;
a step of pressing a mold to the resulting coating film, the mold having a predetermined raised-and-recessed pattern; and an exposure step. The exposure step is carried out while the mold is being pressed to the coating film, and exposure is carried out to the coating film consisting of the silicon-containing resin composition. By removing the mold after exposure and curing, a silica-based coating film having a pattern formed by the shape of the mold may be obtained.

The method of forming the coating film is not particularly limited. For example, the silicon-containing resin composition is applied by a method such as a spraying method, a spin coating method, a roll coating method, a dipping method, or a drip method, and thus a coating film is formed on a substrate. The film thickness of the coating film is not particularly limited. Typically, the thickness of the coating film is determined in such a way that the resulting silica-based coating film has a film thickness of preferably 0.01 to 20 μm, more preferably 2.0 to 20 μm, and 5.0 to 10 μm.

The material of the substrate is not particularly limited as far as it can withstand baking. Examples of a suitable material of the substrate include inorganic materials such as metal, silicon, and glass and heat resistant materials such as polyimide resin and polyamide-imide resin. The thickness of the substrate is not particularly limited, and the substrate may be a film or a sheet.

The substrate may have a raised portion and/or a recessed portion. The raised portion consists of, for example, various devices such as LED devices and organic EL devices. The recessed portion is formed by, for example, etching the surface of the substrate. When the silicon-containing resin composition according to the present invention is used, a flat coating film tends to be formed even when the substrate has a raised-and-recessed surface.

Then, the substrate having the coating film is baked. The method of baking is not particularly limited, and a typical baking method adopts use of an electric furnace or the like. A typical baking temperature is preferably 300° C. or more, more preferably 350° C. or more. The upper limit to the baking temperature is not particularly limited and it is, for example, 1000° C. or less. In the case in which the silicon-containing resin composition comprises the (B) curing agent and/or the (C) nitroxy compound, a silica-based coating film with a lower dielectric constant may be obtained and the amount of a residue remaining in the resulting silica-based coating film (this residue is an impurity derived from the silica-based coating film) may be reduced even when the lower limit of the baking temperature is lowered to 200° C. The atmosphere for the baking is not particularly limited, and the baking may be carried out in an inert gas atmosphere such as a nitrogen atmosphere or an argon atmosphere, in a vacuum, or under reduced pressure. The baking may be carried out in the atmosphere or with appropriate control of the oxygen concentration.

The silica-based coating film formed in this way has no cracks and a low dielectric constant. More specifically, the silica-based coating film may have a film thickness of 2.0 to 20 μm and a relative dielectric constant of lower than 3.5, for example. Therefore, a silica-based coating film formed using the silicon-containing resin composition according to the present invention is suitable for use in applications such as interlayer insulation material. The amount of a residue remaining in the silica-based coating film (this residue is an impurity derived from the silica-based coating film) may be reduced. Therefore, for example, it is considered that excellent inhibition of gas generation from the silica-based coating film is achieved when light-emitting devices such as LEDs or organic ELs, semiconductor devices, solar cell devices, electronic devices such as solid-state image sensors, or light-emitting layers, semiconductor layers, or thin-film solar cells constituting such devices are formed on an insulating layer containing the silica-based coating film according to the present invention in cases where the silica-based coating film is placed under a high-temperature atmosphere or under vacuum. The silica-based coating film is particularly suitable for use as an insulating film in flexible display applications and foldable display applications. Examples of suitable foldable displays include a display device described in Japanese Unexamined Patent Application, Publication No. 2015-026055.

EXAMPLES

The present invention will be specifically described below by way of Examples, but the present invention is not limited to these Examples.

Example 1, Example 3, and Comparative Examples 1 to 4

In Example 1, Example 3, and Comparative Examples 1 to 4, a silicon-containing resin A1 (a polyphenylsiloxane resin having the following structural unit (a-1-1) (mass average molecular weight, 1000)) was dissolved in a solvent of the type specified in Table 1 in such a way that the solid content of 30% by mass was attained. Thus, a silicon-containing resin composition was obtained. The moisture content of each of the silicon-containing resin compositions of Example 1, Example 3, and Comparative Examples 1 to 4 was lower than 0.3% by mass.

[Chem. 39]

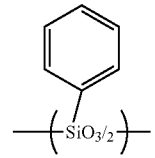

(a-1-1)

The solvents used were the following S1 to S6. S1: Cyclohexyl acetate
S2: Mixture of cyclohexyl acetate and propylene glycol monomethyl ether acetate (mass ratio, 1:1)
S3: Propylene glycol monomethyl ether acetate
S4: 3-Methoxybutyl acetate
S5: Isopropanol
S6: Ethyl diglycol acetate Examples 2 and 4

In Examples 2 and 4, a silicon-containing resin A2 (a chain polysilane containing a silanol group bonded to a silicon atom, a benzyl group, and a methyl group (mass average molecular weight, 1500)) was dissolved in a solvent of the type specified in Table 1 in such a way that the solid content of 30% by mass was attained. Thus, a silicon-containing resin composition was obtained. The moisture content of each of the silicon-containing resin compositions of Examples 2 and 4 was lower than 0.3% by mass.

Each of the resulting silicon-containing resin compositions of the examples and the comparative examples was used to form a silica-based coating film with a film thickness of 5.0 μm by the following method. The resulting silica-based coating film was evaluated for the presence or absence of cracks and the dielectric constant by the following method. When the silica-based coating film had no cracks, the transmittance was also evaluated.

<Formation of Silica-Based Coating Film>
The silicon-containing resin composition was applied to a sample substrate with a spin coater. Thus, a coating film was formed that had a film thickness appropriate for forming a silica-based coating film with a film thickness of 5.0 μm. The resulting coating film was subjected to pre-baking at 100° C. for 2 minutes, followed by baking in a vertical furnace (TS8000 MB manufactured by Tokyo Ohka Kogyo Co., Ltd.) at 350° C. for 30 minutes. Thus, a silica-based coating film having a film thickness of 5.0 μm was obtained.

<Crack Evaluation>
The surface of the resulting silica-based coating film was observed with an optical microscope to confirm the presence or absence of cracks. The presence or absence of cracks is shown in Table 1.

<Evaluation of Dielectric Constant>
The relative dielectric constant of the resulting silica-based coating film was measured with a mercury-probe-type CV measuring system (SSM495 (trade name) manufactured by Semilab Japan KK). Cases where a relative dielectric constant was not measurable due to continuity were evaluated as x, and cases where the relative dielectric constant was measurable with a dielectric constant meter were evaluated as ○. The results of dielectric constant evaluation are shown in Table 1. The relative dielectric constant of the silica-based coating film of both Example 2 or Example 4 formed using the silicon-containing resin composition was lower than 3.5.

<Evaluation of Transmittance>
The transmittance of the silica-based coating films of Example 2 and Example 4 in terms of light with a wavelength of 400 nm was measured. In both cases, the transmittance measured was 98% or more.

TABLE 1

| | (A) Silicon-containing resin | (S) Solvent | Cracks | Dielectric constant |
|---|---|---|---|---|
| Example1 | A1 | S1 | Absent | ○ |
| Example2 | A2 | S1 | Absent | ○ |

TABLE 1-continued

| | (A) Silicon-containing resin | (S) Solvent | Cracks | Dielectric constant |
|---|---|---|---|---|
| Example3 | A1 | S2 | Absent | ○ |
| Example4 | A2 | S2 | Absent | ○ |
| Comparative Example1 | A1 | S3 | Present | x |
| Comparative Example2 | A1 | S4 | Present | x |
| Comparative Example3 | A1 | S5 | Present | x |
| Comparative Example4 | A1 | S6 | Present | x |

Examples 1 to 4 have proven that the silicon-containing resin composition comprising cyclohexyl acetate (a cycloalkyl acetate) as the (S) solvent is capable of forming a silica-based coating film having a film thickness of 5.0 μm, no cracks, a low dielectric constant, and as for Examples 2 and 4, an excellent transmittance. Comparative Examples 1 to 4 have proven that the silicon-containing resin composition comprising no cycloalkyl acetate as the (S) solvent gives a silica-based coating film having a film thickness of 5.0 μm, cracks, and a high dielectric constant. It was also found that, in Comparative Examples 1 to 4, cracks were formed even when the film thickness was reduced to 2.0 μm.

Examples 5 to 12, Comparative Examples 5 to 8

In Examples 5 to 12, (A) a silicon-containing resin of the type specified in Table 2 and (B) a curing agent of the type specified in Table 2 were dissolved in a solvent of the type specified in Table 1 in such a way that the concentration of the (A) silicon-containing resin was 30% by mass and the concentration of the (B) curing agent was 1.5% by mass. Thus, a silicon-containing resin composition was obtained. The moisture content of each of the silicon-containing resin compositions of the Examples and Comparative Examples was lower than 0.3% by mass.

The silicon-containing resins used were the following A3 to A4. A3: Methylphenylpolysilane (a chain polysilane having a methyl group bonded to a silicon atom and also having a phenyl group (mass average molecular weight, 1500))
A4: Methylphenylpolysilane (a chain polysilane having a methyl group bonded to a silicon atom and also having a phenyl group (mass average molecular weight, 13000))
The curing agents used were the following B1 to B5. B1: Hydrochloric Acid
B2: DBU (1,8-diazabicyclo[5.4.0]-7-undecene)
B3: The following compound (a curing agent that generates a base component (imidazole) by the action of light or heat)

[Chem. 40]

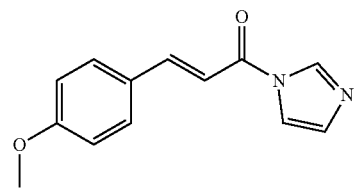

B4: Triphenylphosphine triphenylborane
B5: Boron trifluoride-piperidine complex

The silica-based coating film formed by using the resulting silicon-containing resin composition was evaluated for cracks and the dielectric constant in the same manner as in Examples 1 to 4 and Comparative Examples 1 to 4. In Comparative Examples 5 to 8, cracks were formed even when the film thickness of the silica-based coating film was 2 μm. The resulting silica-based coating film was also evaluated for NMP resistance by the following method. For reference purposes, the results of evaluation of the silica-based coating film formed by using each of the silicon-containing resin compositions of Comparative Examples 1 to 4 are also shown in Table 2.

<Evaluation of NMP Resistance>

Each of the silica-based coating films of Examples 5 to 12, which had excellent crack resistance, was immersed in an NMP solvent at 70° C. for 10 minutes. The percentage change in the film thickness before and after immersion was measured. The smaller the percentage change is, the more excellent the resulting silica-based coating film is with no swelling. The results are shown in Table 2 as well.

TABLE 2

| | (A) Silicon-containing resin | (B) Curing agent | (S) Solvent | Crack resistance | Dielectric constant | NMP resistance |
|---|---|---|---|---|---|---|
| Example5 | A3 | — | S1 | o | 3.1 | 10% |
| Example6 | A3 | — | S2 | o | 3.1 | 10% |
| Example7 | A4 | — | S1 | o | 3.1 | 16% |
| Comparative Example5 | A3 | — | S3 | x | — | — |
| Comparative Example6 | A3 | — | S4 | x | — | — |
| Comparative Example7 | A3 | — | S5 | x | — | — |
| Comparative Example8 | A3 | — | S6 | x | — | — |
| Example8 | A3 | B1 | S1 | o | 2.8 | 11% |
| Example9 | A3 | B2 | S1 | o | 2.8 | 10% |
| Example10 | A3 | B3 | S1 | o | 2.5 | 1% |
| Example11 | A3 | B4 | S1 | o | 2.8 | 6% |
| Example12 | A3 | B5 | S1 | o | 2.8 | 6% |

Examples 5 to 12 have proven that the silicon-containing resin composition comprising cyclohexyl acetate (a cycloalkyl acetate) as the (S) solvent is capable of forming a silica-based coating film having a film thickness of 5.0 μm, no cracks, and a low dielectric constant. It was also proven that the silicon-containing resin composition comprising the (B) curing agent tends to be capable of forming a silica-based coating film having an even lower dielectric constant. It was also proven that particularly when the (B) curing agent was a curing agent that generates a base component by the action of light or heat, not only a low dielectric constant was obtained but also NMP resistance was improved.

<Formation of Silica-Based Coating Film at Low Temperature>

Example 13

The silicon-containing resin composition of Example 10 was applied to a sample substrate with a spin coater. Thus, a coating film was formed that had a film thickness appropriate for forming a silica-based coating film with a film thickness of 5.0 μm. The resulting coating film was subjected to pre-baking at 100° C. for 2 minutes, followed by baking in a vertical furnace (TS8000 MB manufactured by Tokyo Ohka Kogyo Co., Ltd.) at 230° C. for 30 minutes. Thus, a silica-based coating film having a film thickness of 5.0 μm was obtained. Evaluation of cracks, the dielectric constant, and the NMP resistance was carried out in the same manner as in Example 10. Comparable results were obtained for cracks and the dielectric constant, and the NMP resistance was 3%, which was also excellent.

Example 14 to Example 17

(A) a silicon-containing resin of the type and in the amount specified in Table 3 and 0.1 parts by mass of 2,2,6,6-tetramethylpiperidine 1-oxyl free radical (TEMPO) as (C) a nitroxy compound were dissolved in cyclohexyl acetate (S1) in such a way that the concentration of the (A) silicon-containing resin was 30% by mass. Thus, a silicon-containing resin composition was obtained. The resulting silicon-containing resin composition was used to form a silica-based coating film having a film thickness of 5.0 μm in the same manner as in Example 13. The resulting silica-based coating film was evaluated for cracks and the dielectric constant in the same manner as in Examples 1 to 4 and Comparative Examples 1 to 4. The results of evaluation are shown in Table 3.

Examples 18 and 19

(A) a silicon-containing resin of the type and in the amount specified in Table 3, (B) a curing agent of the type and in the amount specified in Table 3, and 0.1 parts by mass of 2,2,6,6-tetramethylpiperidine 1-oxyl free radical (TEMPO) as (C) a nitroxy compound were dissolved in cyclohexyl acetate (S1) in such a way that the concentration of the (A) silicon-containing resin was 30% by mass. Thus, a silicon-containing resin composition was obtained. The resulting silicon-containing resin composition was used to form a silica-based coating film having a film thickness of 5.0 μm in the same manner as in Example 13. The resulting silica-based coating film was evaluated for cracks and the dielectric constant in the same manner as in Examples 1 to 4 and Comparative Examples 1 to 4. The results of evaluation are shown in Table 3.

TABLE 3

| | (A) Silicon-containing resin Type/Parts by mass | (B) Curing agent Type/Parts by mass | (C) Nitroxy compound Type/Parts by mass | (S) Solvent | Crack resistance | Dielectric constant |
|---|---|---|---|---|---|---|
| Example14 | A4/100 | — | C1/0 | S1 | o | 3.1 |
| Example15 | A4/100 | — | C1/0.1 | S1 | o | 2.8 |
| Example16 | A3/100 | — | C1/0.1 | S1 | o | 2.8 |
| Example17 | A3/50 A4/50 | — | C1/0.1 | S1 | o | 2.8 |
| Example18 | A4/100 | B3/1 | C1/0.1 | S1 | o | 2.5 |
| Example19 | A4/100 | B4/1 | C1/0.1 | S11 | o | 2.5 |

Comparison between Example 14 and Examples 15 to 17 has proven that the silicon-containing resin composition comprising the (C) nitroxy compound is capable of forming a silica-based coating film having excellent crack resistance and a lower dielectric constant even when baking is carried out at a low temperature (230° C.). Examples 18 to 19 have proven that the silicon-containing resin composition comprising the (B) curing agent and the (C) nitroxy compound in combination is capable of forming a silica-based coating film having a particularly low dielectric constant even when baking is carried out at a low temperature (230° C.).

The invention claimed is:

1. A silicon-containing resin composition comprising a silicon-containing resin, a nitroxy compound, and a solvent, wherein the silicon-containing resin is one or more selected from the group consisting of a siloxane resin and a polysilane, and
the solvent contains a cycloalkyl acetate represented by the following formula (S1):

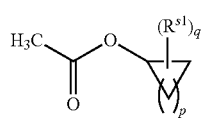

(S1)

wherein $R^{s1}$ represents an alkyl group having 1 to 3 carbon atoms; p is an integer of 1 to 6; and q is an integer of 0 to (p+1) and
a content of the cycloalkyl acetate represented by the above formula (S1) in the solvent is 30 to 100% by mass.

2. The silicon-containing resin composition according to claim 1, further comprising a curing agent.

3. The silicon-containing resin composition according to claim 2, wherein the curing agent comprises at least one curing agent selected from the group consisting of curing agents that generate a base component by the action of light or heat, Brønsted acids, imidazoles, organic amines, organophosphorus compounds, organophosphorus compound complexes, complexes of a Lewis acid and an organic amine, and amidines.

4. A method for forming a silica-based coating film, comprising:
applying the silicon-containing resin composition according to claim 1 to a substrate to form a coating film; and
baking the coating film.

5. The method for forming a silica-based coating film according to claim 4, wherein the silica-based coating film has a film thickness of 0.01 to 20 μm.

6. A method for forming a silica-based coating film, comprising:
applying the silicon-containing resin composition according to claim 2 to a substrate to form a coating film; and
baking the coating film.

7. The method for forming a silica-based coating film according to claim 6, wherein the silica-based coating film has a film thickness of 0.01 to 20 μm.

* * * * *